United States Patent
Danishefsky et al.

(10) Patent No.: US 7,160,856 B2
(45) Date of Patent: Jan. 9, 2007

(54) α-O-LINKED GLYCOCONJUGATES, METHODS OF PREPARATION AND USES THEREOF

(75) Inventors: Samuel J. Danishefsky, Englewood, NJ (US); Dalibor Sames, New York, NY (US); Samuel Hintermann, Basel (CH); Xiao Tao Chen, Newark, DE (US); Jacob B. Schwarz, Ann Arbor, MI (US); Peter Glunz, Wilmington, DE (US); Govindaswami Ragupathi, New York, NY (US); Philip O. Livingston, New York, NY (US); Scott Kuduk, Harleyville, PA (US); Lawrence Williams, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 561 days.

(21) Appl. No.: 10/205,021

(22) Filed: Jul. 25, 2002

(65) Prior Publication Data
US 2003/0083235 A1   May 1, 2003

Related U.S. Application Data

(62) Division of application No. 09/083,776, filed on Mar. 25, 1998, now Pat. No. 6,660,714.

(60) Provisional application No. 60/043,713, filed on Apr. 16, 1997.

(51) Int. Cl.
*A61K 38/14* (2006.01)
*A61K 39/385* (2006.01)
*C07K 9/00* (2006.01)

(52) U.S. Cl. .................. 514/8; 424/185.1; 424/194.1; 424/277.1; 530/322

(58) Field of Classification Search .................. None
See application file for complete search history.

(56) References Cited

U.S. PATENT DOCUMENTS

| | | | |
|---|---|---|---|
| 5,053,489 A | 10/1991 | Kufe | 530/350 |
| 5,212,298 A | 5/1993 | Rademacher et al. | 536/55.2 |
| 5,229,289 A | 7/1993 | Kjeldsen et al. | 435/240.27 |
| 5,280,113 A | 1/1994 | Rademacher et al. | 536/55.2 |
| 5,376,531 A | 12/1994 | Anderson et al. | 435/240.24 |
| 5,421,733 A | 6/1995 | Nudelman et al. | 435/105 |

(Continued)

FOREIGN PATENT DOCUMENTS

EP    341252    11/1997

(Continued)

OTHER PUBLICATIONS

U.S. Appl. No. 08/457,485, filed Jun. 1, 1995, Taylor-Papadimitriou, et al.

(Continued)

*Primary Examiner*—Jeffrey Edwin Russel
(74) *Attorney, Agent, or Firm*—Brenda Herschbach Jarrell; Nadège M. Lagneau; Choate, Hall & Stewart, LLP

(57) ABSTRACT

The present invention provides novel α-O-linked glycoconjugates such as α-O-linked glycopeptides, as well convergent methods for synthesis thereof. The general preparative approach is exemplified by the synthesis of the mucin motif commonly found on epithelial tumor cell surfaces. The present invention further provides compositions and methods of treating cancer using the α-O-linked glycoconjugates.

47 Claims, 48 Drawing Sheets

U.S. PATENT DOCUMENTS

| | | | |
|---|---|---|---|
| 5,491,088 A | 2/1996 | Hellstrom et al. | 435/240.24 |
| 5,625,030 A | 4/1997 | Williams et al. | 528/361 |
| 5,660,834 A | 8/1997 | Kjeldsen et al. | 424/277.1 |
| 5,679,769 A | 10/1997 | Danishefsky et al. | 530/322 |
| 5,683,674 A | 11/1997 | Taylor-Papadimitriou et al. | 424/1.49 |
| 5,747,048 A | 5/1998 | Kjeldsen et al. | 424/277.1 |
| 5,798,090 A | 8/1998 | Longenecker et al. | 424/279.1 |
| 5,807,559 A | 9/1998 | Jondal | 424/278.1 |
| 5,858,994 A | 1/1999 | Kretzschmar et al. | 514/62 |
| 5,871,990 A | 2/1999 | Clausen et al. | 435/193 |
| 6,013,779 A | 1/2000 | Wong et al. | 536/18.6 |
| 6,090,789 A | 7/2000 | Danishefsky et al. | 514/25 |
| 6,222,020 B1 | 4/2001 | Taylor-Papadimitriou et al. | 530/395 |
| 6,238,668 B1 | 5/2001 | Danishefsky et al. | 424/184.1 |
| RE38,046 E | 3/2003 | Longenecker et al. | 424/279.1 |
| 6,660,714 B1 * | 12/2003 | Danishefsky et al. | 514/2 |
| 2002/0006900 A1 | 1/2002 | Danishefsky et al. | 514/8 |
| 2002/0038017 A1 | 3/2002 | Danishefsky et al. | 536/53 |
| 2003/0153492 A1 | 8/2003 | Danishefsky et al. | |
| 2004/0102607 A1 | 5/2004 | Danishefsky et al. | |
| 2004/0208884 A1 | 10/2004 | Danishefsky et al. | |
| 2005/0222398 A1 | 10/2005 | Danishefsky et al. | |

FOREIGN PATENT DOCUMENTS

| | | |
|---|---|---|
| JP | 8-319300 | 12/1996 |
| WO | WO 93/21948 | 11/1993 |
| WO | WO 96/34005 | 10/1996 |
| WO | WO 96/40198 | 12/1996 |
| WO | WO 97/03995 | 2/1997 |
| WO | WO 98/30190 | 7/1998 |
| WO | WO 98/46246 | 10/1998 |
| WO | WO 99/15201 | 4/1999 |
| WO | WO 99/48515 | 9/1999 |
| WO | WO 01/14395 | 3/2001 |
| WO | WO 01/14395 A2 | 3/2001 |
| WO | WO 01/14395 A3 | 3/2001 |

OTHER PUBLICATIONS

* Allen, et al., "A Second Generation Synthesis of the MBr1 (Globo-H) Breast Tumor Antigen: New Application of the N-Pentenyl Glycoside Method for Achieving Complex Carbohydrate Protein Linkages", Chem. Eur. J., 6(8): 1366-1375, 2000.
* Balcom. B.J. and Petersen, N.O., "Synthesis and Surfactant Behavior of an Unusual Cyclic Triester Based on a cis, cis-1, 3, 5-Cyclohexanetriol Headgroup," Langmuir, 7:2425-2427, 1991.
* Bayle, et al., "O-(3-Butenyl) A Stable Blocking Group Removable by Ozonolysis", Carbohydrate Research, 232: 375-380, 1992.
* Bencomo et al.. "Synthesis of glycopeptides having clusters of O-glycosylic disaccharide chains . . . ," Carbohydrate Research, 116, C9-C12. 1983.
* Bilodeau M.T., "Total Synthesis of a Human Breast Tumor Associated Antigen", J. Am. Chem. Soc., 117:7840-7841. 1995.
* Boehm T. et al., "Development of a Novel Silyl Ether Linker for Solid-Phase Organic Synthesis" J. Org. Chem., 61:6498-6499, 1996.
* Boon. T.. "Toward a Genetic Analysis of Tumor Rejection Antigens," Adv. Can. Res., 58:177-211, 1992.
* Broddefalk, et al., "Preparation of a Glycopeptide Analogue of Type II Collagen—Use of Acid Labile Protective Groups for Carbohydrate Moieties in Solid Phase Synthesis of O-Linked Glycopeptides", Tetrahedron Letters, NL, Elsevier Science, 37(17): 3011-3014, 1996.
* Cabaret. et al., "Amphiphilic Liposaccharides. Synthesis and Reductive Cleavage of C-Allyl, O-Allyl, and O-Butenyl Glycosyl Derivatives". Carbohydrate Research. 189: 341-348, 1989.
* Chan et al., "Polymer-anchored Organosilyl Protecting Group in Organic Synthesis," J. Chem. Soc., Chem. Commun., 909-911, 1985.
* Collins and Ferrier Monosaccharides: Their Chemistry and Their Roles in Natural Products, Publ. by John Wiley & Sons, Ltd., p. 4, 1995.
* Commissions on Nomenclature of Organic Chemistry and Physical Organic Chemistry. IUPAC, Pure and Applied Chemistry, 67, 1325 and 1334, 1995.
* Danishefsky et al. "Glycals in Organic Synthesis: The Evolution of Comprehensive Strategies for the Assembly of Oligosaccharides and Glycoconjugates of Biological Consequence" Angew. Chem. Int. Ed. Engl., 35:1380-1419, 1996.
* Danishefsky et al. "From the Laboratory to the Clinic: A Retrospective on Fully Synthetic Carbohydrate-Based Anticancer Vaccines" Angew. Chem. Int. Ed. Engl., 39:836-863, 2000.
* Dermer. G.B., "Another Anniversary for the War on Cancer," Bio/Technology, 12, 320, 1994.
* Deshpande et al., "Strategy in Oligosaccharide Synthesis: An Application to a Concise Total Synthesis of the KH-1 (Adenocarcinoma) Antigen," J. Am. Chem. Soc., 120, 1600-1614, 1998.
* Elofsson and Kihlberg, "Synthesis of Tn and Sialyl Tn Building Blocks for Solid Phase Glycopeptide Synthesis," Tetrahedron Letters, 36, 7499-7502, 1995.
* Elofsson et al., "Preparation of Tn and Sialyl Tn Building Blocks . . . ," Tetrahedron. 53, 369-390. 1997.
* Ezzell, "Cancer "Vaccines": An Ideal Whose Time Has Come?" J. NIH Res, 7, 46-49, 1995.
* Finn et al., "MUC-1 Epithelial Tumor Mucin-based Immunity and Cancer Vaccines" Immunol. Rev., 145, 61-89, 1995.
* Freshney, R.I., Culture of Animal Cells, A Manual of Basic Techniques. Alan R. Liss, Inc., New York, p. 3-4, 1983.
* Fung et al., "Active Specific Immunotherapy of Murine Mammary . . . ," Cancer Research. 50, 4308-4314. 1990.
* Garg et al., "Developments in the Synthesis of Glycopeptides Containing Glycosyl L-Asparagine, L-Serine, and L-Threonine" Adv. Carb. Chem. Biochem., 50, 277-310, 1994.
* Gleiter et al., "Synthesis and Properties of Eight-and Ten-Membered Selenaradialenes," Tetrahedron Letters, 35, 8779-8782. 1994.
* Grice et al., "Tuning and Reactivity of Glycosides: Efficient One-pot Oligosaccharide Synthesis," Synlett, 781-784. 1995.
* Iijima, II. and Ogawa, T. "Synthesis of Mucin-type O-Glycosylated Amino Acid $\beta$-Gal-(1-3)-[$\alpha$-Neu5Ac-2→6)]-GalNAc-(1→3)-Ser" Carbohydr. Res., 186, 95-106, 1989.
* Kaizu et al., "Novel Fucolipids of Human Adenocarcinoma: Monoclonal Antibody Specific for Trifucosyl Le$^Y$ (III$^3$FucV$^3$FucVI$^2$FucnI.c$_6$) and a Possible Three-dimensional Epitope Structure," J. Biol. Chem. 261, 11254-11258. 1986.
* Kameyama et al., "Total Synthesis of Sialyl Lewis X*," Carbohydrate Research, 209, cl-c4, 1991.
* Kim et al., "Expression of Le$^Y$ and Extended Le$^Y$ Blood Group-related Antigens in Human Malignant, Premalignant, and Nonmalignant Colonic Tissues," Cancer Res., 46, 5985-5992, 1986.
* Koganty et al., "Glycopeptide- and Carbohydrate-based Synthetic Vaccines for the Immunotherapy of Cancer," Drug Discovery Today, 5, 190-198, 1996.
* Kondo et al., "In vitro Action of Human and Porcine $\alpha$-amylases . . ., " Carbohydrate Research, 204, 207-213, 1990.
* Kunz, H. and Birnbach, S., "Synthesis of O-Glycopeitides of the Tumor-Associated T$_N$ . . ." Angew. Chem. Int. Ed. Engl., 25. 360-362, 1986.
* Lassaletta, et al., "Glycosyl Imidates. Synthesis of the Hexasaccharide Moiety of Globo H (Human Breast Cancer) Antigen", Liebigs Ann. 9: 1417-1423, 1996.
* Lay L. et al., "Oligosaccharides Related to Tumor-Associated Antigens", Helv. Chim. Acta. 77:509-514, 1994.
* Liebe, B. and Kunz H., "Solid Phase Synthesis of a Tumor-Associated Sialyl-T$_N$ Antigen Glycopeptide- . . . ," Angew. Chem. Int. Ed. Engl. 33. 618-621. 1997.
* Lönn. H. "Synthesis of a Tri- and a Hepta-saccharide . . . ," Carbohydrate Research, 139. 105-113, 1985.
* Nicolaou et al., "Stereocontrolled Synthesis of Sialyl Le$^x$ . . . ," J. Chem. Soc., Chem. Commun., 870-872. 1991.
* Nudelman et al., Novel Fucolipids of Human Adenocarcinoma: Characterization of the Major Le$^y$ Antigen of Human Adenocarcinoma as Trifucosylnonaosyl Le$^y$ Lycolipid (III$^3$FucV$^3$FucVI$^2$FucnLc$_6$), *J. Biol. Chem.*, 261, 11247-11253, 1986.

* Park, et al., "Total Synthesis and Proof of Structure of a Human Breast Tumor (Globo-H) Antigen". *J. Am. Chem. Soc.*, 118(46): 11488-11500, 1996.
* Paulsen et al., "Glycosidierung mit Thioglycosiden von oligosacchariden zu Segmenten von O-Glycoproteinen" *Liebigs Ann. Chem.*, 75-86. 1988.
* Ragupathi et al., "Immunization of Mice with a Fully Synthetic Globo II Antigen Results in Antibodies Against Human Cancer Cells: A Combined Chemical Immunological Approach to the Fashioning of an Anticancer Vaccine" *Angew. Chem. Int. Ed. Engl.* 36, 125-128, 1997.
* Ragupathi, et al., "A Fully Synthetic Globo H Carbohydrate Vaccine Induces a Focused Humoral Response in Prostate Cancer Patients: A Proof of Principle", *Angew. Chem., Int. Ed.*, 38(4): 563-566. 1999.
* Ragupathi. G. "Carbohydrate Antigens as Targets for Active Specific Immunotherapy" *Cancer Immunol. Immunther.*, 43, 152-157, 1996.
* Randolph J.T. et al., "An Interactive Strategy for the Assembly of Complex, Branched Oligosaccharide Domains on a Solid Support: A Concise Synthesis of the Lewis$^b$ Domain in Bioconjugatable Form", *Angew. Chem. Int. Ed$_1$. Engl.*, 33(14):1470-1473, 1994.
* Randolph et al., "Major Simplifications in Oligosaccharide Syntheses Arising from a Solid-Phase Based Method: An Application to the Synthesis of the Lewis b Antigen," *J. Amer. Chem. Soc.*, 117. 5712-5719, 1995.
* Reid, et al., "N-Pentenyl Glycosides in Organic Chemistry: A Contemporary Example of Serendipity", *Synlett*, 927-942, 1992.
* Roberge et al., "A Strategy for a Convergent Synthesis of N-Linked Glycopeptides on a Solid Support," *Science* (Washington, D.C.), 269, 202-204, 1995.
* Schultheiss-Riemann. P. and Kunz, H., "O-Glycopeptide Synthesis . . . ," *Angew. Chem. Int. Ed. Engl.*, 22, 62-63, 1983.
* Seeberger et al., "Synthesis of Biologically Important Oligosaccharides and Other Glycoconjugates by the Glycal Assembly Method," *Aldrichimica Acta*, 30(3), 75-92, 1997.
* Slovin et al., "Carbohydrate Vaccines in Cancer: Immunogenicity of Fully Synthetic Globo H Hexasaccharide Conjugate in Man" *Proc. Natl. Acad. Sci. USA*.96, 5710-5715, 1999.
* Spitler. "Cancer Vaccines: The Interferon Analogy," *Cancer Biotherapy*, 10, 1-3, 1995.
* Tao, M. and Levy, R. "Idiotype/Granulocyte-macrophage Colony-simulating Factor Fusion Protein as a Vaccine for B-cell Lymphoma." *Nature*, 362, 755-758, 1993.
* Tokoyuni et al., "Synthetic Vaccines: I. Synthesis of Multivalent Tn Antigen Cluster-Lysyllysine Conjugates." *Tetrahedron Lett.*, 31, 2673-2676, 1990.
* Tokoyuni, T. and Singhal, A.K., "Synthetic Carbohydrate . . . ," *Chem. Soc. Rev.*, 24, 231-242, 1995.
* Toyokuni et al., "Synthetic Carbohydrate Vaccines: Synthesis and Immunogenicity of Tn Antigen Conjugates", *Bioorg. Med. Chem.*, 2, 1119-1132, 1994.
* Udodong, et al., "A Ready, Convergent Synthesis of the Heptasaccharide GPI Membrane Anchor of Rat Brain Thy-1 Glycoprotein" *J. Am. Chem. Soc.*, 115: 7886-7887, 1993.
* Waldmann et al. "New Enzymatic Protecting Group Techniques for the Construction of Peptides and Glycopeptides" *Biomed. Biochim. Acta.* 50 (10/11) S243-S248, 1991.
* Yura et al., "Preparation of oligosaccharide-linked polystyrene and method for immobilization of lectin and base materials for cells", abstract, Jpn. Kokai Tokkyo Koho (Japan), Dec. 3, 1996.
* Zhang et al., "Immune Sera and Monoclonal Antibodies Define Two Configurations for the Sialyl Tn Tumor Antigen", *Cancer Res.*, 55, 3364-3368, 1995.

Allen et al., "Pursuit of optimal carbohydrate-based anticancer vaccines: preparation of a multiantigenic unimolecular glycopeptide containing the Tn, MBrl, and Lewis$^y$ antigens", *J. Am. Chem. Soc.*, 123:1890-1897, 2001.

Allen et al., "A second generation synthesis of the MBrl (Globo-H) breast tumor antigen: new application of the n-pentenyl glycoside method for achieving complex carbohydrates protein linkages", *Chem. Eur. J.*, 6(8):1366-1375, 2000.

Biswas et al., "Construction of carbohydrate-based antitumor vaccines: synthesis of glycosyl amino acids by olefin cross-metathesis", *Tetrahedron Letters*, 43:6107-6110, 2002.

Blackwell et al., "New approaches to olefin cross-metathesis", *J. Am. Chem. Soc.*, 122:58-71, 2000.

Bosse et al., "Linear Synthesis of the tumor-associated carbohydrate antigens Globo-H, SSEA-3, and Gb3", *J. Org. Chem.*, 67:6659-6670, 2002.

Keding et al., "Hydroxynorleucine as a glycosyl acceptor is an efficient means for introducing amino acid functionality into complex carbohydrates", *Tetrahedron Letters*, 44:3413-3416, 2003.

Kim et al., "Effect of immunological adjuvant combinations on the antibody and T-cell response to vaccination with MUC1-KLH and GD3-KLH conjugates", *Vaccine*, 19:530-537, 2001.

Kudryashov et al., "Toward optimized carbohydrate-based anticancer vaccines: Epitope clustering, carrier structure, and adjuvant all influence antibody responses to lewis$^y$ conjugates in mice", *Proc. Natl. Acad. Sci. USA*, 98:3264-3269, 2001.

Nicolaou et al., "A practical and enantioselective synthesis of glycosphingolipids and related compounds. Total synthesis of Globotriasosylceramide (Gb$_3$)", *J. Am. Chem. Soc.*, 110:7910-7912, 1988.

Ragupathi et al., "A Fully synthetic Globo H carbohydrate vaccine induces a focused humoral response in prostate cancer patients: a proof of principle", *Angew. Chem. Int. Ed.*, 38(4):563-566, 1999.

Ragupathi et al., "On the power of chemical synthesis: Immunological evaluation of models for multiantigenic carbohydrate-based cancer vaccines", *Proc. Natl. Acad. Sci. USA*, 99(21):13699-13704, 2002.

Slovin et al., "Carbohydrate vaccines in cancer: Immunogenicity of a fully Globo H hexasaccharide conjugate in man", *Proc. Natl. Acad. Sci. USA*, 96:5710-5715, 1999.

Williams et al., "In pursuit of an anticancer vaccine: a monomolecular construct containing multiple carbohydrate antigens", *Tetrahedron Letters*, 41:9505-9508, 2000.

Database BIOSIS'Online! Biosciences Information Service, Philadelphia, PA, US: Mar. 22, 2002, Kovbasnjuk Olga et al., "Glycosphingolipid Gb3 as biomarker for invasive colon carcinoma cells", FASEB Journal, 16(5):A1200, 2002, Annual Meeting of Professional Research Scientist on Experimental Biology; New Orleans, LA, USA, Apr. 20-24, 2002.

International Search Report issued for PCT application PCT/US03/22657, dated Nov. 12, 2003.

Chen et al., "Exploration of Modalities in Building a α-O-Linked Systems Through Glycal Assembly: A Total Synthesis of the Mucin-Related Flα Antigen" *J. Am. Chem. Soc.*, 120, 7760-7769, 1998.

Kudryashov et al. "Immunogenicity of Synthetic Conjugates of Lewis$^y$ Oligosaccharide with Proteins in Mice: Towards the Design of Anticancer Vaccines," *Cancer Immunol Immunother*, 45, 281-286, 1998.

Kuduk et al. "Synthetic and Immunological Studies on Clustered Modes of Mucin-Related Tn and TF O-Linked Antigens: The Preparation of a Glycopeptide-Based Vaccine for Clinical Trials against Prostate Cancer," *J. Am. Chem. Soc.*, 120, 12474-12485, 1998.

Liu et al., "Structurally Defined Synthetic Cancer Vaccines: Analysis of Structure, Glycosylation and Recognition of cancer Associated Mucin, MUC-1 Derived Peptides," *Glycoconjugate Journal*, 12, 607-617 (1995).

Paulsen et al., "Synthesis of the Glycosyl Amino Acids . . . ," *Carbohydrate Research*, 268, 17-34, 1995.

Qiu et al., "Mucin Type Glycopeptides: Synthesis of Core 2, Core 6 and F1-α Building Blocks and Unexpected Reactions," *Tetrahedron Letters*, 38(1), 45-48, 1997.

Sames et al., "Convergent Total Synthesis of a Tumor-Associated Mucin Motif," *Nature*, 389, 587-591, 1997.

Toyokuni et al., "Synthetic Vaccines: Synthesis of a Dimeric Tn Antigen-Lipopeptide Conjugate that Elicits Immune Responses Against Tn-Expressing Glycoproteins," *J. Am. Chem. Soc.*, 116, 395-396, 1994.

Zhang, et al., "Selection of Tumor Agents as Targets for Immune Attack Using Immunohistochemistry: II. Blood Group Related Antigens," *Int. J. Cancer*, 73, 50-56, 1997.

U.S. Appl. No. 09/641,742, filed Aug. 18, 2000, Danishefsky, et al.

Yin et al., "Serological and immunochemical analysis of Lewis y (Le$^y$) blood group antigen expression in epithelial ovarian cancer" *Int. J. Cancer*, 65(4):406-12, 1996.

* cited by examiner

16, $R^1$ = Me; $R^2$ = Ac; $R^3$ = —CO—;
$R^4$ = Fmoc; $R^5$ = Bn

I, $R^1$, $R^2$, $R^3$, $R^5$ = H; $R^4$ = Ac h, i, j

Ac-Ala-Pro-Asn-Thr-Arg-Pro-Ala-Pro-Gly-Ser-Ala-Pro-Pro-Ala (SEQ ID No.: 1)

1

$ST_N$ 1a, R =

T(TF) 1b, R =

(2,3)ST 1c, R =

Glycophorine 1d, R =

1

3-Le^y 1e, R =

6-Le^y 1f, R =

1) AcOH
2) MeOTf,

3) Global Deprotection

Glycophorine 1d

Pal = CH₃(CH₂)₁₄CO 1) morpholine / DMF (77%)
2) HATU, HOAT, collidine, DMF, 2 (56%)

3  R =

4  R = BSA

5  R = KLH

1. R = H (Ser)
2. R = CH (Thr)

Tn Trimer Glycopeptide

Conjugation 12, carrier = KLH
13, carrier = BSA

SEQUENCE LISTING

<160> NUMBER OF SEQ ID NOS: 2

<210> SEQ ID NO 1
<211> LENGTH: 15
<212> TYPE: PRT
<213> ORGANISM: Artificial
<220> FEATURE:
<223> OTHER INFORMATION: N-terminal fragment of tumor-associated mucin.
<220> FEATURE:
<221> NAME/KEY: misc_feature
<222> LOCATION: (11)..(11)

```
-continued

<223> OTHER INFORMATION: Xaa can be any naturally occurring amino acid

<400> SEQUENCE: 1

Ala Pro Asn Thr Arg Pro Ala Pro Gly Ser Xaa Ala Pro Pro Ala
1               5                   10                  15

<210> SEQ ID NO 2
<211> LENGTH: 4
<212> TYPE: PRT
<213> ORGANISM: Artificial
<220> FEATURE:
<223> OTHER INFORMATION: N-terminal fragment of tumor-associated mucin.

<400> SEQUENCE: 2

Ala Val Ala Val
1
```

α-O-LINKED GLYCOCONJUGATES, METHODS OF PREPARATION AND USES THEREOF

This application is a divisional application of parent application Ser. No. 09/083,776 filed on Mar. 25, 1998 (now U.S. Pat. No. 6,660,714), which claims priority to provisional application No. 60/043,713 filed on Apr. 16, 1997, each of which is incorporated herein by reference in its entirety.

GOVERNMENT SUPPORT

This invention was made with government support under grants CA-28824, HL-25848 and AI-16943 from the National Institutes of Health. Accordingly, the U.S. Government has certain rights in the invention.

FIELD OF THE INVENTION

The present invention is in the field of α-O-linked glycopeptides. In particular, the present invention relates to methods for the preparation of α-O-linked glycoconjugates with clustered glycodomains which are useful as anticancer therapeutics. The present invention also provides novel compositions comprising such α-O-linked glycoconjugates and methods for the treatment of cancer using these glycoconjugates.

Throughout this application, various publications are referred to, each of which is hereby incorporated by reference in its entirety into this application to more fully describe the state of the art to which the invention pertains.

BACKGROUND OF THE INVENTION

The role of carbohydrates as signaling molecules in the context of biological processes has recently gained prominence. M. L. Phillips, et al., *Science,* 1990, 250, 1130; M. J. Polley, et al., *Proc. Natl. Acad. Sci. USA,* 1991 88, 6224: T. Taki, et al., *J. Biol. Chem.,* 1996, 261, 3075; Y. Hirabayashi, A. Hyogo, T. Nakao, K. Tsuchiya, Y. Suzuki, M. Matsumoto, K. Kon, S. Ando, *ibid.,* 1990, 265, 8144; O. Hindsgaul, T. Norberg, J. Le Pendu, R. U. Lemieux, *Carbohydr. Res.* 1982, 109, 109; U. Spohr, R. U. Lemieux, *ibid.,* 1988, 174, 211). The elucidation of the scope of carbohydrate involvement in mediating cellular interaction is an important area of inquiry in contemporary biomedical research. The carbohydrate molecules, carrying detailed structural information, tend to exist as glycoconjugates (cf. glycoproteins and glycolipids) rather than as free entities. Given the complexities often associated with isolating the conjugates in homogeneous form and the difficulties in retrieving intact carbohydrates from these naturally occurring conjugates, the applicability of synthetic approaches is apparent. (For recent reviews of glycosylation see: Paulsen, H.; *Angew. Chemie Int. Ed. Engl.* 1982, 21, 155; Schmidt, R. R., *Angew. Chemie Int. Ed. Engl.* 1986, 25, 212; Schmidt, R. R., *Comprehensive Organic Synthesis,* Vol. 6, Chapter 1(2), Pergamon Press, Oxford, 1991; Schmidt, R. R., *Carbohydrates, Synthetic Methods and Applications in Medicinal Chemistry,* Part I, Chapter 4, VCH Publishers, Weinheim, N.Y., 1992. For the use of glycals as glycosyl donors in glycoside synthesis, see Lemieux, R. U., *Can. J. Chem.,* 1964, 42, 1417; Lemieux, R. U., Fraiser-Reid, B., *Can. J. Chem.* 1965, 43, 1460; Lemieux, R. U.; Morgan, A. R., *Can. J. Chem.* 1965, 43, 2190; Thiem, J., et al., *Synthesis* 1978, 696; Thiem, J. Ossowski, P., *Carbohydr. Chem.,* 1984, 3, 287; Thiem, J., et al., *Liebigs Ann. Chem.,* 1986, 1044; Thiem, J. in *Trends in Synthetic Carbohydrate Chemistry,* Horton, D., et al., eds., ACS Symposium Series No. 386, American Chemical Society, Washington, D.C., 1989, Chapter 8.)

The carbohydrate domains of the blood group substances contained in both glycoproteins and glycolipids are distributed in erythrocytes, epithelial cells and various secretions. The early focus on these systems centered on their central role in determining blood group specificities. R. R. Race; R. Sanger, *Blood Groups* in Man, 6th ed., Blackwell, Oxford, 1975. However, it is recognized that such determinants are broadly implicated in cell adhesion and binding phenomena. (For example, see M. L. Phillips, et al., *Science* 1990, 250, 1130.) Moreover, ensembles related to the blood group substances in conjugated form are encountered as markers for the onset of various tumors. K. O. Lloyd, *Am. J. Clinical Path.,* 1987, 87, 129; K. O. Lloyd, *Cancer Biol.,* 1991, 2, 421. Carbohydrate-based tumor antigenic factors have applications at the diagnostic level, as resources in drug delivery or ideally in immunotherapy. Toyokuni, T., et al., *J. Am. Chem Soc.* 1994, 116, 395; Dranoff, G., et al., *Proc. Natl. Acad. Sci. USA* 1993, 90, 3539; Tao, M-H.; Levy, R., *Nature* 1993, 362, 755; Boon, T., *Int. J. Cancer* 1993, 54, 177; Livingston, P. O., *Curr. Opin. Immunol.* 1992, 4, 624; Hakomori, S., *Annu. Rev. Immunol.* 1984, 2, 103; K. Shigeta, et al., *J. Biol. Chem.* 1987, 262, 1358.

The present invention provides new strategies and protocols for glycopeptide synthesis. The object is to simplify such preparations so that relatively complex domains can be assembled with high stereospecificity. Major advances in glycoconjugate synthesis require the attainment of a high degree of convergence and relief from the burdens associated with the manipulation of blocking groups. Another requirement is that of delivering the carbohydrate determinant with appropriate provision for conjugation to carrier proteins or lipids. Bernstein, M. A.; Hall, L. D., *Carbohydr. Res.* 1980, 78, Cl; Lemieux, R. U., *Chem. Soc. Rev.* 1978, 7, 423; R. U. Lemieux, et al., *J. Am. Chem. Soc.* 1975, 97, 4076. This is a critical condition if the synthetically derived carbohydrates are to be incorporated into carriers suitable for clinical application.

Antigens which are selective (or ideally specific) for cancer cells could prove useful in fostering active immunity. Hakomori, S., *Cancer Res.,* 1985, 45, 2405–2414; Feizi, T., *Cancer Surveys* 1985, 4, 245–269. Novel carbohydrate patterns are often presented by transformed cells as either cell surface glycoproteins or as membrane-anchored glycolipids. In principle, well chosen synthetic glycoconjugates which stimulate antibody production could confer active immunity against cancers which present equivalent structure types on their cell surfaces. Dennis, J., *Oxford Glycostems Clyconews,* Second Ed., 1992; Lloyd, K. O., in *Specific Immunotherapy of Cancer with Vaccines,* 1993, New York Academy of Sciences, pp. 50–58. Chances for successful therapy improve with increasing restriction of the antigen to the target cell. For example, one such specific antigen is the glycosphingolipid isolated by Hakomori and collaborators from the breast cancer cell line MCF-7 and immunocharacterized by monoclonal antibody MBrl. Bremer, E. G., et al., *J. Biol. Chem.* 1984, 259, 14773–14777; Menard, S., et al., *Cancer Res.* 1983, 43, 1295–1300.

The surge of interest in glycoproteins (M. J. McPherson, et al., eds., *PCR A Practical Approach,* 1994, Oxford University Press, Oxford, G. M. Blackburn; M. J. Gait, Eds., *Nucleic Acids in Chemistry and Biology,* 1990, Oxford University Press, Oxford; A. M. Bray; A. G. Jhingran; R. M. Valero; N. J. Maeji, *J. Org. Chem.* 1944, 59, 2197; G. Jung;

A. G. Beck-Sickinger, *Angew Chem. Int. Ed. Engl.* 1992, 31, 367; M. A. Gallop; R. W. Barrett; W. J. Dower; S. P. A. Fodor; E. M. Gordon, *J. Med. Chem.* 1994, 37, 1233; H. P. Nestler; P. A. Bartlett; W. C. Still, *J. Org. Chem.* 1994, 59, 4723; M. Meldal, *Curr. Opin. Struct. Biol.* 1994, 4, 673) arises from heightened awareness of their importance in diverse biochemical processes including cell growth regulation, binding of pathogens to cells (O. P. Bahl, in *Glycoconjugates: Composition, structure, and function*, H. J. Allen, E. C. Kisailus, Eds., 1992, Marcel Dekker, Inc., New York, p. 1), intercellular communication and metastasis (A. Kobata, *Acc. Chem. Res.* 1993, 26, 319). Glycoproteins serve as cell differentiation markers and assist in protein folding and transport, possibly by providing protection against proteolysis. C. Opdenakker, et al., *FASEB J.* 1993, 7, 1330. Improved isolation techniques and structural elucidation methods (A. De; K.-H. Khoo, *Curr. Opin. Struct. Biol.* 1993, 3, 687) have revealed high levels of microheterogeneity in naturally-produced glycoproteins. R. A. Dwek, et al., *Annu. Rev. Biochem.* 1993, 62, 65. Single eukaryotic cell lines often produce many glycoforms of any given protein sequence. For instance, erythropoietin (EPO), a clinically useful red blood cell stimulant against anemia, is glycosylated by more than 13 known types of oligosaccharide chains when expressed in Chinese hamster ovary cells (CHO) (Y. C. Lee; R. T. Lee, Eds., *Neoglycoconjugates: Preparation and Applications*, 1994, Academic Press, London). The efficacy of erythropoietin is heavily dependent on the type and extent of glycosylation (E. Watson, et al., *Glycobiology*, 1994, 4, 227).

Elucidation of the biological relevance of particular glycoprotein oligosaccharide chains requires access to pure entities, heretofore obtained only by isolation. Glycoprotein heterogeneity renders this process particularly labor-intensive. However, particular cell lines can be selected to produce more homogeneous glycoproteins for structure-activity studies. U.S. Pat. No. 5,272,070. However, the problem of isolation from natural sources remains difficult.

Receptors normally recognize only a small fraction of a given macromolecular glycoconjugate. Consequently, synthesis of smaller but well-defined putative glycopeptide ligands could emerge as competitive with isolation as a source of critical structural information (Y. C. Lee; R. T. Lee, Eds., supra).

Glycoconjugates prepared by total synthesis are known to induce mobilization of humoral responses in the murine immune system. Ragupathi, G., et al., *Angew. Chem. Int. Ed. Engl.* 1997, 36, 125; Toyokuni, T.; Singhal, A. K., *Chem. Soc. Rev.* 1995, 24, 231; *Angew. Chem. Int. Ed. Engl.* 1996, 35, 1381. Glycopeptides, in contrast to most glycolipids and carbohydrates themselves, are known to bind to major histocompatability complex (MHC) molecules and stimulate T cells in favorable cases. Deck, B., et al., *J. Immunology* 1995, 1074; Haurum, J. S., et al., *J. Exp. Med.* 1994, 180, 739; Sieling, P. A., et al., *Science* 1995, 269, 227 (showing T cell recogniztion of CD1-restricted microbial glycolipid). Properly stimulated T cells express receptors that specifically recognize the carbohydrate portion of a glycopeptide. The present invention demonstrates a means of augmenting the immunogenicity of carbohydrates by use of a peptide attachment.

Preparation of chemically homogeneous glycoconjugates, including glycopeptides and glycoproteins, constitutes a challenge of high importance. Bill, R. M.; Flitsch, S. L.; *Chem. & Biol.* 1996, 3, 145. Extension of established cloning approaches to attain these goals are being actively pursued. Various expression systems (including bacteria, yeast and cell lines) provide approaches toward this end, but, as noted above, produce heterogeneous glycoproteins. Jenkins, N., et al., *Nature Biotech.* 1996, 14, 975. Chemical synthesis thus represents a preferred avenue to such bi-domainal constructs in homogeneous form. Moreover, synthesis allows for the assembly of constructs in which selected glycoforms are incorporated at any desired position of the peptide chain.

Prior to the subject invention, methods of glycopeptide synthesis pioneered by Kunz and others allowed synthetic access to homogenous target systems both in solution and solid phase (M. Meldal, *Curr. Opin. Struct. Biol*, 1994, 4, 710; M. Meldal, in *Neoglycoconjugates: Preparation and Applications*, supra; S. J. Danishefsky; J. Y. Roberge, in *Glycopeptides and Related Compounds: Chemical Synthesis, Analysis and Applications*, 1995, D. G. Large, C. D. Warren, Eds., Marcel Dekker, New York; S. T. Cohen-Anisfeld and P. T. Lansbury, Jr., *J. Am. Chem. Soc.*, 1993, 175, 10531; S. T. Anisfeld; P. T. Lansbury Jr., *J. Org. Chem*, 1990, 55, 5560; D. Vetter, et at., *Angew. Chem. Int. Ed. Engl*, 1995, 34, 60–63). Cohen-Anisfeld and Lansbury disclosed a convergent solution-based coupling of selected already available saccharides with peptides. S. T. Cohen-Anisfeld; P. T. Lansbury, Jr., *J. Am. Chem. Soc.*, supra.

Thus, few effective methods for the preparation of α-O-linked glycoconjugates were known prior to the present invention. Nakahara, Y., et al., In *Synthetic Oligosaccharides*, ACS Symp. Ser. 560, 1994, pp. 249–266; Garg, H. G., et al., *Adv. Carb. Chem. Biochem.* 1994, 50, 277. Nearly all approaches incorporated the amino acid (serine or threonine) at the monosaccharide stage. This construction would be followed by elaboration of the peptidyl and carbohydrate domains in a piecemeal fashion. Qui, D.; Koganty, R. R.; *Tetrahedron Lett.* 1997, 38, 45. Eloffson, M., et al., *Tetrahedron* 1997, 53, 369. Meinjohanns, E., et al., *J. Chem. Soc., Perkin Trans.* 1, 1996, 985. Wang, Z-G., et al., *Carbohydr. Res.* 1996, 295, 25. Szabo, L., et al., *Carbohydr. Res.* 1995, 274, 11. The scope of the synthetic problem is well known in the art, but little progress has been achieved. The present invention provides an alternate, simpler and more convergent approach (FIG. 2).

Toyokuni et al., *J. Amer. Chem. Soc.*, 1994, 116, 395, have prepared synthetic vaccines comprising dimeric Tn antigen-lipopeptide conjugates having efficacy in eliciting an immune response against Tn-expressing glycoproteins. However, prior to investigations of the present inventors, it was not appreciated that the surface of prostate cancer cells presents glycoproteins comprising Tn clusters linked via threonine rather than serine residues. Accordingly, the present invention provides a vaccine having unexpectedly enhanced anticancer efficacy.

SUMMARY OF THE INVENTION

Accordingly, one object of the present invention is to provide novel α-O-linked glycoconjugates including glycopeptides and related compounds which are useful as anti-cancer therapeutics.

Another object of the present invention is to provide synthetic methods for preparing such glycoconjugates. An additional object of the invention is to provide compositions useful in the treatment of subjects suffering from cancer comprising any of the glycoconjugates available through the preparative methods of the invention, optionally in combination with pharmaceutical carriers.

The present invention is also intended to provide a fully synthetic carbohydrate vaccine capable of fostering active immunity in humans.

A further object of the invention is to provide methods of treating subjects suffering from of cancer using any of the glycoconjugates available through the preparative methods of the invention, optionally in combination with pharmaceutical carriers.

DETAILED DESCRIPTION OF THE INVENTION

Figure 1:
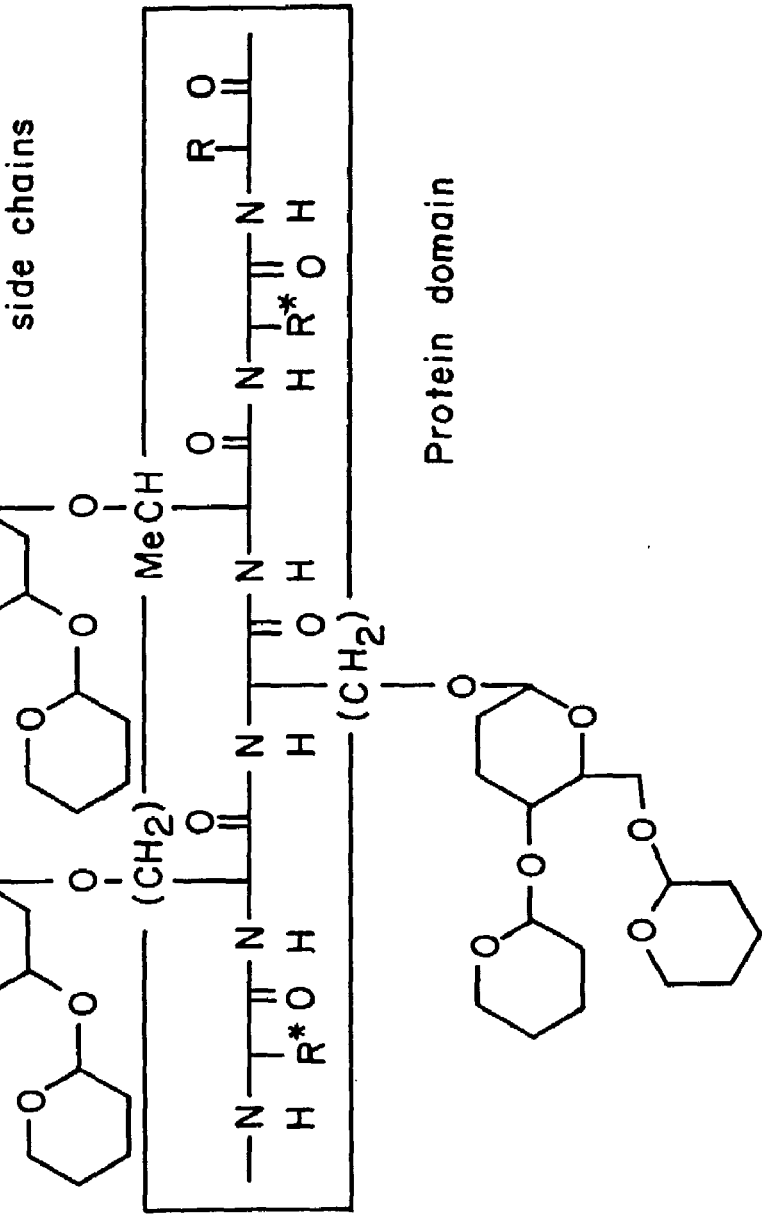
FIG. 1 shows a schematic structure for α-O-linked glycoconjugates as present in mucins.

The subject invention provides novel α-O-linked glycoconjugates, useful in the prevention and treatment of cancer.

The present invention provides a glycoconjugate having the structure:

wherein m, n, p and q are 0, 1, 2 or 3 such that m+n+p+q≦6; wherein A, B, C, D, E and F are independently amino acyl or hydroxy acyl residues wherein A is N- or O-terminal and is either a free amine or ammonium form when A is amino acyl or a free hydroxy when A is hydroxy acyl, or A is alkylated, arylated or acylated; wherein F is either a free carboxylic acid, primary carboxamide, mono- or dialkyl carboxamide, mono- or diarylcarboxamide, linear or branched chain (carboxy)alkyl carboxamide, linear or branched chain (alkoxycarbonyl)alkyl-carboxamide, linear or branched chain (carboxy)arylalkylcarboxamide, linear or branched chain (alkoxycarbonyl)alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester; wherein from one to about five of said amino acyl or hydroxy acyl residues are substituted by a carbohydrate domain having the structure:

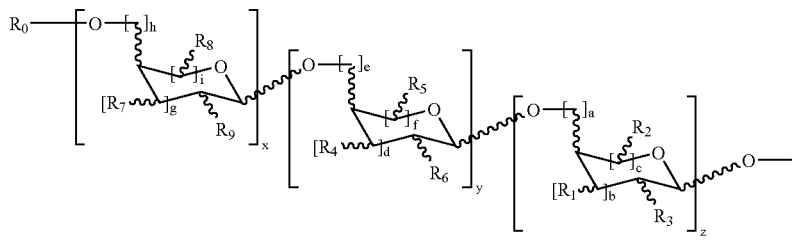

wherein a, b, c, d, e, f, g, h, i, x, y and z are independently 0, 1, 2 or 3; wherein the carbohydrate domain is linked to the respective amino acyl or hydroxy acyl residue by substitution of a side group substituent selected from the group consisting of OH, COOH and $NH_2$; wherein $R_0$ is hydrogen, a linear or branched chain alkyl, acyl, arylalkyl or aryl group; wherein $R_1$, $R_2$, $R_3$, $R_4$, $R_5$, $R_6$, $R_7$, $R_8$ and $R_9$ are each independently hydrogen, OH, $OR^i$, $NH_2$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein $R^i$ is hydrogen, CHO, $COOR^{ii}$, or a substituted or unsubstituted linear or branched chain alkyl, arylalkyl or aryl group or a saccharide moiety having the structure:

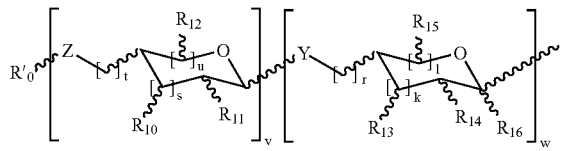

wherein Y and Z are independently NH or O; wherein k, l, r, s, t, u, v and w are each independently 0, 1 or 2, wherein $R'_0$ is hydrogen, a linear or branched chain alkyl, acyl, arylalkyl or aryl group; wherein $R_{10}$, $R_{11}$, $R_{12}$, $R_{13}$, $R_{14}$ and $R_{15}$ are each is independently hydrogen, OH, $OR^{iii}$, $NH_2$, $NHCOR^{iii}$, F, ($CH_2OH$, $CH_2OR^{iii}$, or an optionally substituted linear or branched chain lower alkyl, (mono-, di- or tri)hydroxyalkyl, (mono- di- or tri-)acyloxyalkyl, arylalkyl or aryl group; wherein $R_{16}$ is hydrogen, COOH, $COOR^{ii}$, $CONHR^{ii}$, optionally substituted linear or branched chain lower alkyl or aryl group; wherein $R^{iii}$ is hydrogen, CHO, $COOR^{iv}$, or an optionally substituted linear or branched chain alkyl, arylalkyl or aryl group; and wherein $R^{ii}$ and $R^{iv}$ are each independently H, or an optionally substituted linear or branched chain alkyl, arylalkyl or aryl group.

In a certain embodiment, the present invention provides the glycoconjugate as shown above wherein at least one carbohydrate domain has the oligosaccharide structure of a cell surface epitope. In a particular embodiment, the present invention provides the glycoconjugate wherein the epitope is $Le^a$, $Le^b$, $Le^x$, or $Le^y$. In another particular embodiment, the present invention provides the glycoconjugate wherein the epitope is MBr1, a truncated MBr1 pentasaccharide or a truncated MBr1 tetrasaccharide.

In another embodiment, the present invention provides a glycoconjugate wherein the amino acyl residue is derived from a natural amino acid. In another embodiment, the invention provides the glycoconjugate wherein at least one amino acyl residue has the formula: —NH—Ar—CO—. In a specific embodiment, the Ar moiety is p-phenylene.

In another embodiment, the present invention provides the glycoconjugate wherein at least one amino acyl or hydroxy acyl residue has the structure:

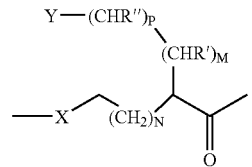

wherein M, N and P are independently 0, 1 or 2; X is NH or O; Y is OH, NH or COOH; and wherein R' and R" are independently hydrogen, linear or branched chain alkyl or aryl. In a specific embodiment, the amino acyl residue attached to the carbohydrate domain is Ser or Thr.

In another embodiment, the present invention provides the glycoconjugate wherein one or more of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{15}$ is 1RS,2RS,3-trihydroxy-propyl.

The present invention also provides a pharmaceutical composition for treating cancer comprising the above-shown glycoconjugate and a pharmaceutically suitable carrier.

The present invention further provides a method of treating cancer in a subject suffering therefrom comprising administering to the subject a therapeutically effective amount of the above-shown glycoconjugate and a pharmaceutically suitable carrier. The method of treatment is effective when the cancer is a solid tumor or an epithelial cancer.

The present invention also provides a trisaccharide having the structure:

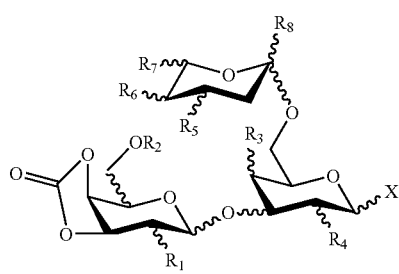

wherein $R_1$, $R_3$, $R_4$, $R_5$, $R_6$ and $R_7$ are each independently hydrogen, OH, $OR^i$, $NH_2$, $NHCOR^i$, F, $N_3$, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein $R^i$ is H, CHO, COOR$^{ii}$, or a substituted or unsubstituted linear or branched chain alkyl, arylalkyl or aryl group; wherein R$_2$ is hydrogen, a linear or branched chain alkyl, acyl, arylalkyl or aryl group; wherein R$_8$ is hydrogen, COOH, COOR$^{ii}$, CONHR$^{ii}$, a substituted or unsubstituted linear or branched chain alkyl or aryl group; wherein R$^{ii}$ is a substituted or unsubstituted linear or branched chain alkyl, arylalkyl or aryl group; and wherein X is a halide, a trihaloacetamidate, an alkyl or aryl sulfide or a dialkylphosphite. In a preferred embodiment, the invention provides the above-shown trisaccharide wherein X is a triethylphosphite. The invention further provides the trisaccharide wherein R$_7$ is 1RS,2RS,3-trihydroxypropyl or 1RS,2RS,3-triacetoxypropy). In addition, the invention provides the trisaccharide wherein R$_8$ is COOH.

The present invention also provides a trisaccharide amino acid having the structure:

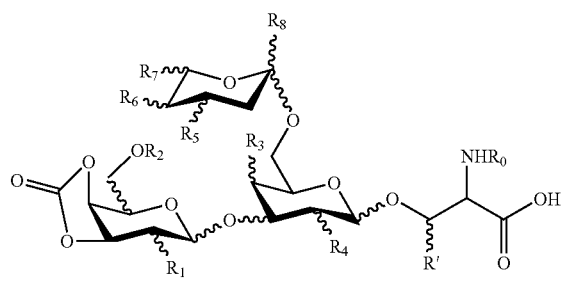

wherein R$_1$, R$_3$, R$_4$, R$_5$, R$_6$ and R$_7$ are each independently hydrogen, OH, OR$^i$, NH$_2$, NHCOR$^i$, F, N$_3$, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl or aryl group; wherein R$^i$ is H, CHO, COOR$^{ii}$, or a substituted or unsubstituted linear or branched chain alkyl, arylalkyl or aryl group; wherein R$_2$ is hydrogen, a linear or branched chain alkyl, acyl, arylalkyl or aryl group; wherein R$_8$ is hydrogen, COOH, COOR$^{ii}$, CONHR$^{ii}$, a substituted or unsubstituted linear or branched chain alkyl or aryl group; wherein R$^{ii}$ is a substituted or unsubstituted linear or branched chain alkyl, arylalkyl or aryl group; wherein R$_0$ is a base-labile N-protecting group; and wherein R' is hydrogen or a lower alkyl group. A variety of N-protecting groups would be acceptable in the preparation of the above-shown trisaccharide amino acid. R$_0$ may preferably be one of several base-sensitive protecting groups, but more preferably fluorenylmethyloxycarbonyl (FMOC).

The present invention provides a method of inducing antibodies in a human subject, wherein the antibodies are capable of specifically binding with human tumor cells, which comprises administering to the subject an amount of the glycoconjugate disclosed herein effective to induce the antibodies. In a certain embodiment, the present invention provides a method of inducing antibodies wherein the glycoconjugate is bound to a suitable carrier protein. In particular, preferred examples of the carrier protein include bovine serum albumin, polylysine or KLH.

In another embodiment, the present invention contemplates a method of inducing antibodies which further comprises co-administering an immunological adjuvant. In a certain embodiment, the adjuvant is bacteria or liposomes. Specifically, favored adjuvants include *Salmonella minnesota* cells, bacille Calmette-Guerin or QS21. The antibodies induced are typically selected from the group consisting of (2,6)-sialyl T antigen, Le$^a$, Le$^b$, Le$^x$, Le$^y$, GM1, SSEA-3 and MBr1 antibodies. The method of inducing antibodies is useful in cases wherein the subject is in clinical remission or, where the subject has been treated by surgery, has limited unresected disease.

The present invention also provides a method of preventing recurrence of epithelial cancer in a subject which comprises vaccinating the subject with the glycoconjugate shown above which amount is effective to induce antibodies. In practicing this method, the glycoconjugate may be used alone or be bound to a suitable carrier protein. Specific examples of carrier protein used in the method include bovine serum albumin, polylysine or KLH. In a certain embodiment, the present method of preventing recurrence of epithelial cancer includes the additional step of co-administering an immunological adjuvant. In particular, the adjuvant is bacteria or liposomes. Favored adjuvants include *Salmonella minnesota* cells, bacille Calmette-Guerin or QS21. The antibodies induced by the method are selected from the group consisting of (2,6)-sialyl T antigen, Le$^a$, Le$^b$, Le$^x$, Le$^y$, GM1, SSEA-3 and MBr1 antibodies.

The present invention further provides a glycoconjugate having the structure:

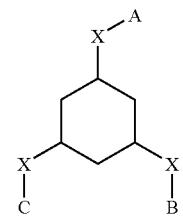

wherein X is O or NR; wherein R is H, linear or branched chain alkyl or acyl; wherein A, B and C independently linear or branched chain alkyl or acyl, —CO—(CH$_2$)$_p$—OH or aryl, or have the structure:

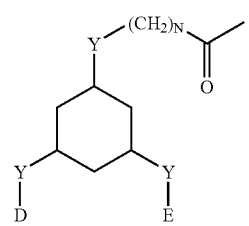

wherein Y is O or NR; wherein D and E have the structure: —(CH$_2$)$_p$—OH or —CO—(CH$_2$)$_p$—OH; wherein N and P are independently an integer between 0 and 12; wherein D and E and, when any of A, B and C are —CO—(CH$_2$)$_p$—OH, A, B and C are independently substituted by a carbohydrate domain having the structure:

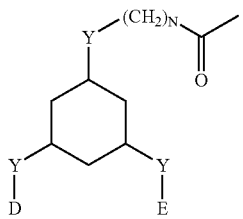

wherein Y is O or NR; wherein D and E have the structure: —(CH$_2$)$_p$OH or —CO(CH$_2$)$_p$OH; wherein n and p axe independently an integer between 0 and 12; wherein D and E and, A, B, and C when they are —CO(CH$_2$)$_p$OH, are independently substituted by a carbohydrate domain having the structure:

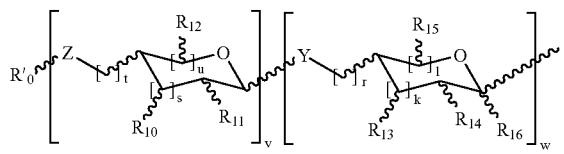

wherein Y and Z are independently NH or O; wherein k, l, r, s, t, u, v and w are each independently 0, 1 or 2, wherein R'$_0$ is hydrogen, a linear or branched chain alkyl, acyl, arylalkyl or aryl group; wherein R$_{10}$, R$_{11}$, R$_{12}$, R$_{13}$, R$_{14}$ and R$_{15}$ is independently hydrogen, OH, OR$^{iii}$, NH$_2$, NHCOR$^{iii}$, F, CH$_2$OH, CH$_2$R$^{iii}$, or an optionally substituted linear or branched chain lower alkyl, (mono-, di- or tri)hydroxyalkyl, (mono- di- or tri-)acyloxyalkyl. arylalkyl or aryl group; wherein R$_{16}$ is hydrogen, COOH, COOR$^{ii}$, CONHR$^{ii}$, optionally substituted linear or branched chain lower alkyl or aryl group; wherein R$^{iii}$ is hydrogen, CHO, COOR$^{iv}$, or an optionally substituted linear or branched chain alkyl, arylalkyl or aryl group; and wherein R$^{ii}$ and R$^{iv}$ are each independently H or an optionally substituted linear or branched chain alkyl, arylalkyl or aryl group. In a certain embodiment, the present invention provides the above-shown glycoconjugate wherein at least one carbohydrate domain has the oligosaceharide structure of a cell surface epitope. In one embodiment, the epitope is Le$^a$, Le$^b$, Le$^x$, or Le$^y$. In another embodiment, the epitope is MBr1, a truncated MBr1 pentasacchaxide or a truncated MBr1 tetrasaccharide, in a particular embodiment, the invention provides the glycoconjugate shown above wherein one or more of R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$ and R$_{15}$ is 1RS,2RS,3-tiihydroxy-propyl.

The invention also provides a pharmaceutical composition for treating cancer comprising the glycoconjugate shown above and a pharmaceutically suitable carrier.

The invention further provides a method of treating cancer in a subject suffering therefrom comprising administering to the subject a therapeutically effective amount of the glycoconjugate shown above and a pharmaceutically suitable carrier. The method is useful in cases where the cancer is a solid tumor or an epithelial cancer.

The present invention also provides a glycoconjugate comprising a core structure and a carbohydrate domain wherein the core structure is:

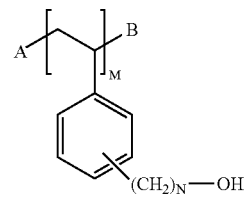

wherein M is an integer from about 2 to about 5,000; wherein N is 1, 2, 3 or 4; wherein A and B are suitable polymer termination groups, including linear or branch chain alkyl or aryl groups; wherein the core structure is substituted by the carbohydrate domain having the structure:

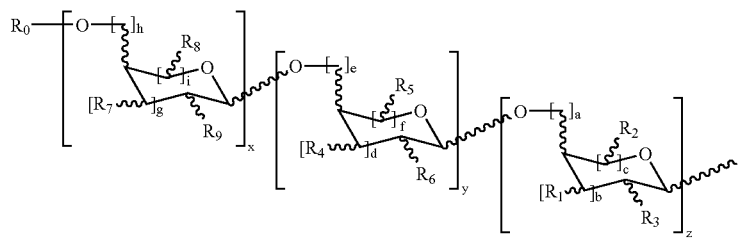

wherein a, b, c, d, e, f, g, h, i, x, y and z are independently 0, 1, 2 or 3; wherein the carbohydrate domain is linked to the core structure by substitution of the OH substituents; wherein R$_0$ is hydrogen, a linear or branched chain alkyl, acyl, arylalkyl or aryl group; wherein R$_1$, R$_2$, R$_3$, R$_4$, R$_5$, R$_6$, R$_7$, R$_8$ and R$_9$ are each independently hydrogen, OH, OR$^i$, NH$_2$, NHCOR$^i$, F, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl or aryl group; wherein R$^i$ is hydrogen, CHO, COOR$^{ii}$, or a substituted or unsubstituted linear or branched chain alkyl, arylalkyl or aryl group or a saccharide moiety having the structure:

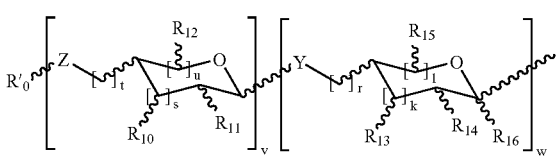

wherein Y and Z are independently NH or O; wherein k, l, r, s, t, u, v and w are each independently 0, 1 or 2, wherein $R'_0$ is hydrogen linear or branched chain alkyl, acyl, arylalkyl or aryl group wherein $R_{10}$, $R_{11}$, $R_{12}$, $R_{13}$, $R_{14}$ and $R_{15}$ is are each is independently hydrogen, OH, $OR^{iii}$, $NH_2$, $NHCOR^{iii}$, F, $CH_2OH$, $CH_2OR^{iii}$, or an optionally substituted linear or branched chain lower alkyl, (mono-, di- or tri)hydroxyalkyl, (mono- di- or tri-)acyloxyalkyl, arylalkyl or aryl group; wherein $R_{16}$ is hydrogen, COOH, $COOR^{ii}$, $CONHR^{ii}$, optionally substituted linear or branched chain lower alkyl or aryl group; wherein $R^{iii}$ is hydrogen, CHO, $COOR^{iv}$, or an optionally substituted linear or branched chain alkyl, arylalkyl or aryl group; and wherein $R^{ii}$ and $R^{iv}$ are each independently H, or an optionally substituted linear or branched chain alkyl, arylalkyl or aryl group.

In a specific embodiment, the present invention provides a method of preparing glycopeptides related to the mucin family of cell surface glycoproteins. Mucins are characterized by aberrant α-O-glycosidation patterns with clustered arrangements of carbohydrates α-O-linked to serine and threonine residues. FIG. 1. Mucins are common markers of epithelial tumors (e.g., prostate and breast carcinomas) and certain blood cell tumors. Finn, O. J., et al., *Immunol. Rev.* 1995, 145, 61.

threonine via a block approach. In addition, the present invention provides an O-linked glycopeptide incorporating such glycosyl units with clustered ST epitopes (1,20).

A broad range of carbohydrate domains are contemplated by the present invention. Special mention is made of the carbohydrate domains derived from the following cell surface epitopes and antigens:

MBr1 Epitope: Fucα1→2Galβ1→3GalNAcβ1→3Galα1→4Galβ1→4Glu→0cer

Truncated MBr1 Epitope Pentasaccharide: Fucα1→2Galβ1→3GalNAcβ1→3Galα1→4Galβ1

Truncated MBr1 Epitope Tetrasaccharide: Fucα1→2Galβ1→3GalNAcβ1→3Galα1

SSEA-3 Antigen: 2Galβ1→3GalNAcβ1→3Galα1→4Galβ1

$Le^y$ Epitope: Fucα1→2Galβ1→4(Fucα1→3)GalNAcβ1

GM1 Epitope: Galβ1→3GalNAcβ1→4Galβ1→4(NeuAcα2→3)Glu→0cer

Methods for preparing carbohydrate domains based on a solid-phase methodology have been disclosed in U.S. Pat. Nos. 5,543,505 and 5,708,163 and in PCT International Application No. PCT/US96/10229, the contents of which are incorporated by reference.

The present invention also provides a glycoconjugate having the structure:

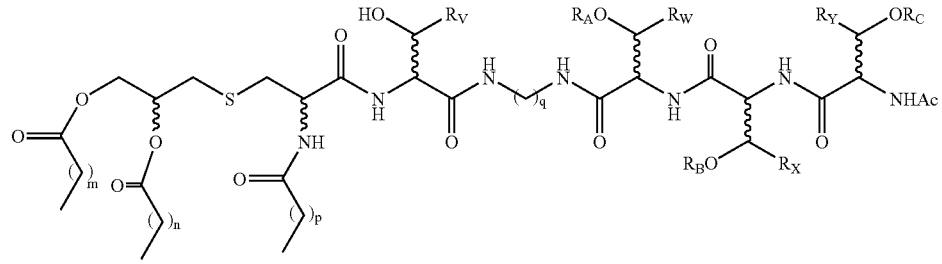

Figure 2A:
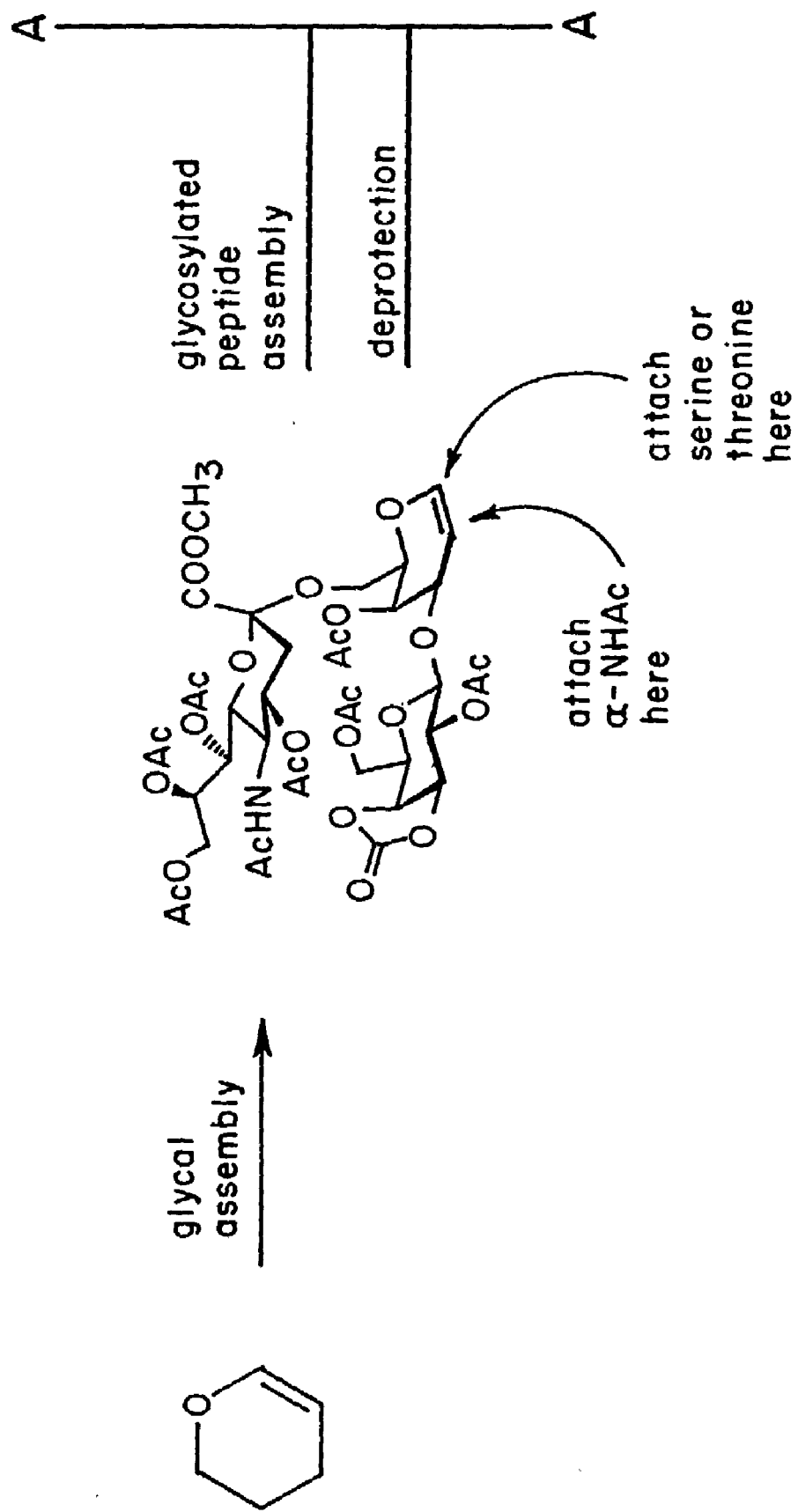
FIG. 2 provides a general synthetic strategy to mucin glycoconjugates.
Figure 2B:
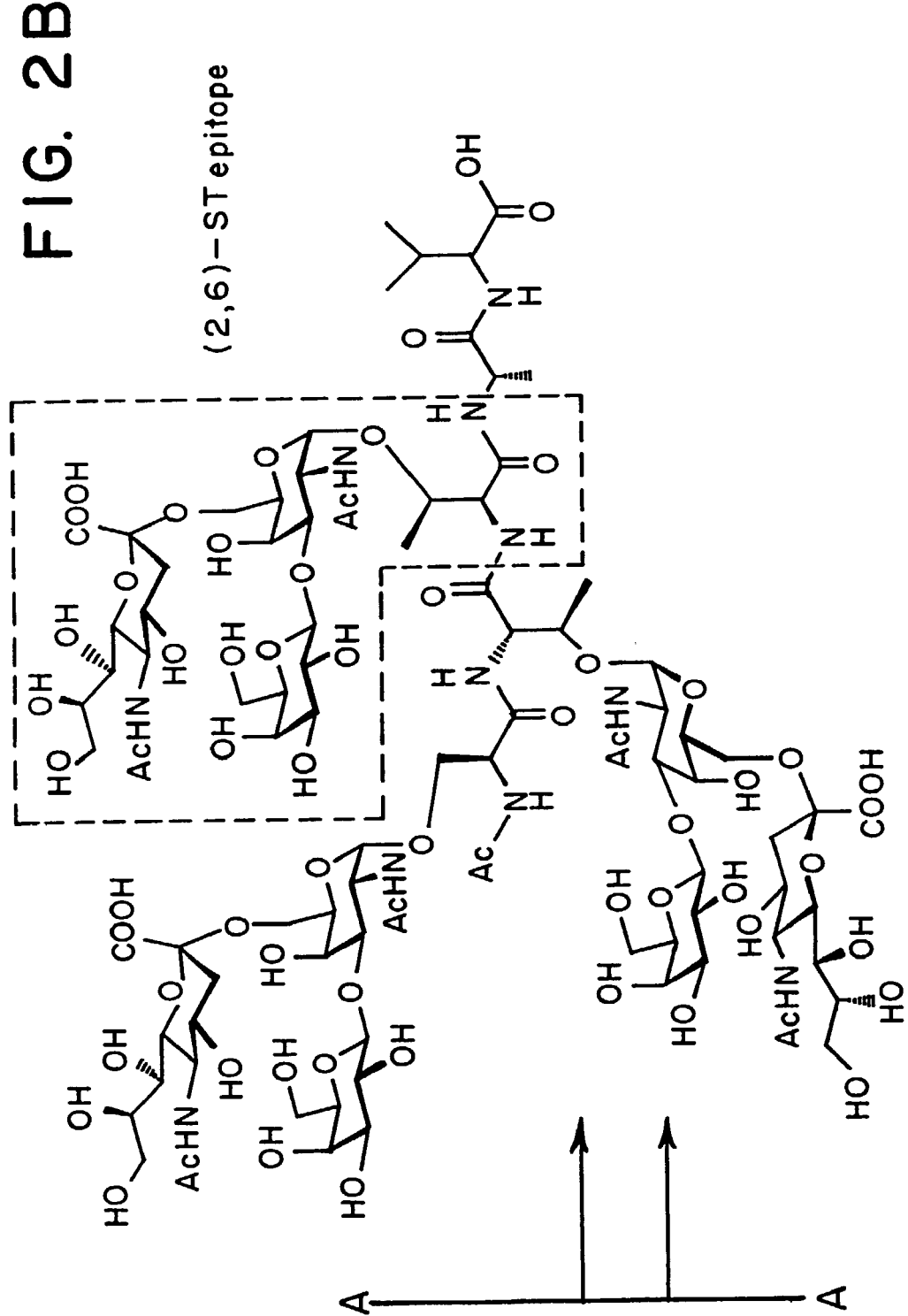

The (2,6)-Sialyl T antigen (ST antigen) is an example of the "glycophorin family" of α-O-linked glycopeptides (FIG. 2). It is selectively expressed on myelogenous leukemia cells. Fukuda, M., et al., *J. Biol. Chem.* 1986, 261, 12796. Saitoh, O., et al., *Cancer Res.* 1991, 51, 2854. Thus, in a specific embodiment, the present invention provides a synthetic route to pentapeptide 1, which is derived from the N-terminus of CD43 (Leukosialin) glycoprotein. Pallant, A., et al., *Proc. Natl. Acad. Sci. USA* 1989, 86, 1328.

In particular, the invention provides a stereoselective preparation of α-O-linked (2,6)-ST glycosyl serine and wherein m, n and p are integers between about 8 and about 20; wherein q is an integer between about 1 and about 8; wherein $R_V$, $R_W$, $R_X$ and $R_Y$ are independently hydrogen, optionally substituted linear or branched chain lower alkyl or optionally substituted phenyl; wherein $R_A$, $R_B$ and $R_C$ are independently a carbohydrate domain having the structure:

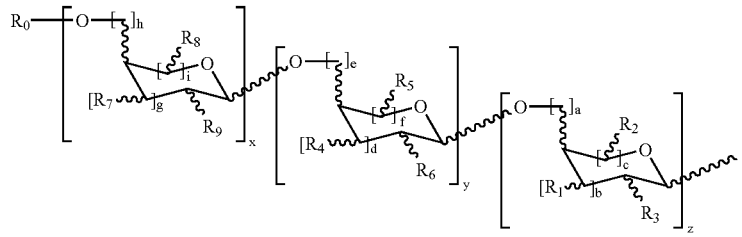

wherein a, b, c, d, e, f, g, h, i, x, y and z are independently 0, 1, 2 or 3; wherein $R_0$, is hydrogen, linear or branched chain lower alkyl, acyl, arylalkyl or aryl group; wherein $R_1$, $R_2$, $R_3$, $R_4$, $R_5$, $R_6$, $R_7$, $R_8$ and $R_9$ are each independently hydrogen, OH, $OR^i$, $NH_2$, $NHCOR^i$, F, $CH_2OH$, $CH_2OR^i$, an optionally substituted linear or branched chain lower alkyl, (mono-, di- or tri)hydroxyalkyl, (mono-, di- or tri)acyloxyalkyl, arylalkyl or aryl group; wherein $R^i$ is hydrogen, CHO, $COOR^{ii}$, or an optionally substituted linear or branched chain lower alkyl, arylalkyl or aryl group or a saccharide moiety having the structure:

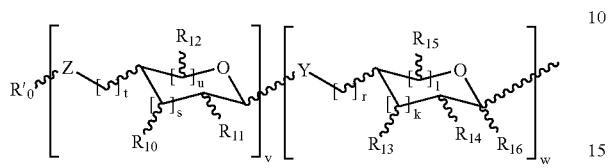

wherein Y and Z are independently NH or O; wherein k, l, r, s, t u, v and w are each independently 0, 1 or 2, wherein $R'_0$ is hydrogen, a linear or branched chain alkyl, acyl, arylalkyl or aryl group; wherein $R_{10}$, $R_{11}$, $R_{12}$, $R_{13}$, $R_{14}$ and $R_{15}$ is independently hydrogen, OH, $OR^{iii}$, $NH_2$, $NHCOR^{iii}$, F, $CH_2OH$, $CH_2OR^{iii}$, or an optionally substituted linear or branched chain lower alkyl, (mono-, di- or tri)hydroxyalkyl, (mono- di- or tri-)acyloxyalkyl, arylalkyl or aryl group; wherein $R_{16}$ is hydrogen, COOH, $COOR^{ii}$, $CONHR^{ii}$, optionally substituted linear or branched chain lower alkyl or aryl group; wherein $R^{iii}$ is hydrogen, CHO, $COOR^{iv}$, or an optionally substituted linear or branched chain alkyl, arylalkyl or aryl group; and wherein $R^{ii}$ and $R^{iv}$ are each independently H or an optionally substituted linear or branched chain alkyl, arylalkyl or aryl group. In a certain embodiment, the invention provides a glycoconjugate wherein $R_v$, $R_w$, $R_x$ and $R_y$ are methyl.

In a certain other embodiment, the carbohydrate domains may be independently monosaccharides or disaccharides. In one embodiment, the invention provides a glycoconjugate wherein y and z are 0; wherein x is 1; and wherein $R_3$ is NHAc. In another embodiment, the invention provides a glycoconjugate wherein h is 0; wherein g and i are 1; wherein $R_7$ is OH; wherein $R_0$ is hydrogen; and wherein $R_8$ is hydroxymethyl. In yet another embodiment, m, n and p are 14; and wherein q is 3. In a preferred embodiment, each amino acyl residue of the glycoconjugate therein has an L-configuration.

In a specific example, the carbohydrate domains of the glycoconjugate are independently:

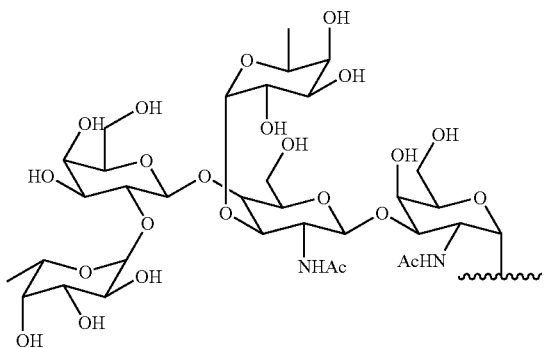

In another example, the carbohydrate domains are independently

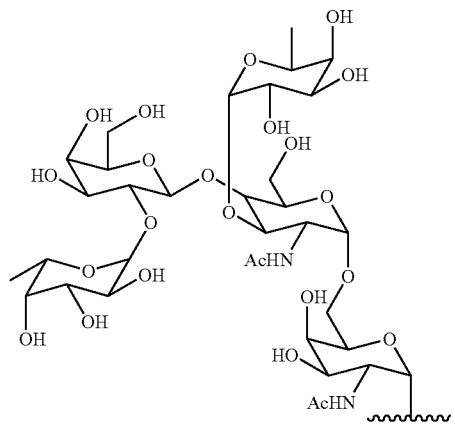

Additionally, the carbohydrate domains are independently:

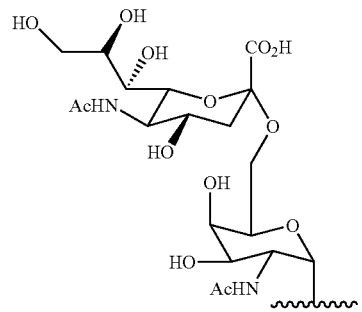

The carbohydrate domains are also independently:

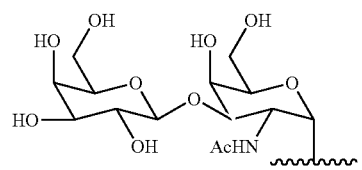

The carbohydrate domains also are independently

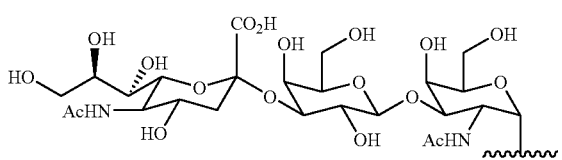

Also, the carbohydrate domains may be independently:

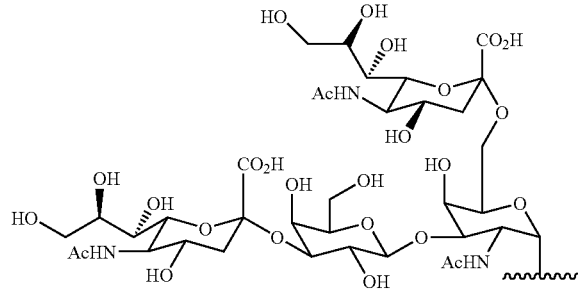

The carbohydrate domains are also independently:

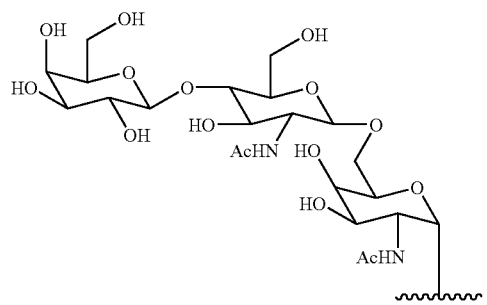

The present invention provides a glycoconjugate having the structure:

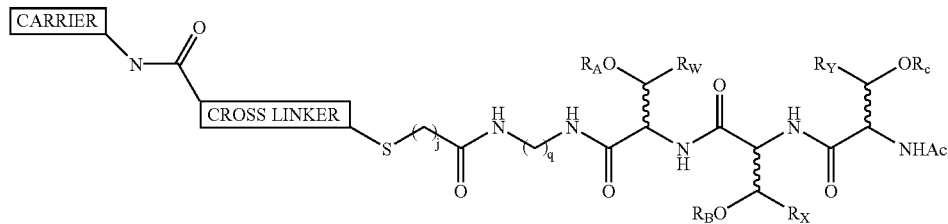

wherein the carrier is a protein; wherein the cross linker is a moiety derived from a cross linking reagent capable of conjugating a surface amine of the carrier and a thiol; wherein m, n and p are integers between about 8 and about 20; wherein j and q are independently integers between about 1 and about 8; wherein $R_V$, $R_W$, $R_X$ and $R_Y$ are independently hydrogen, optionally substituted linear or branched chain lower alkyl or optionally substituted phenyl; wherein $R_A$, $R_B$ and $R_C$ are independently a carbohydrate domain having the structure:

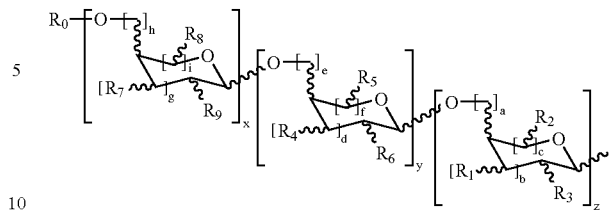

wherein a, b, c, d, e, f, g, h, i, x, y and z are independently 0, 1, 2 or 3; wherein $R_0$ is hydrogen, linear or branched chain lower alkyl, acyl, arylalkyl or aryl group; wherein $R_1$, $R_2$, $R_3$, $R_4$, $R_5$, $R_6$, $R_7$, $R_8$ and $R_9$ are each independently hydrogen, OH, $OR^i$, $NH_2$, $NHCOR^i$, F, $CH_2OH$, $CH_2OR^i$, an optionally substituted linear or branched chain lower alkyl, (mono-, di- or tri)hydroxyalkyl, (mono-, di- or tri)acyloxyalkyl, arylalkyl or aryl group; wherein $R^i$ is hydrogen, CHO, $COOR^{ii}$, or an optionally substituted linear or branched chain lower alkyl, arylalkyl or aryl group or a saccharide moiety having the structure:

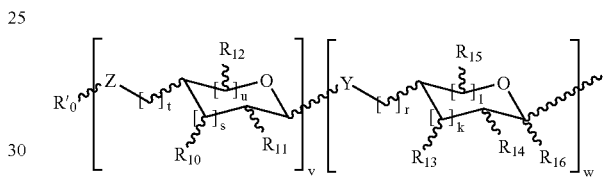

wherein Y and Z are independently NH or O; wherein k, l, r, s, t, u, v and w are each independently 0, 1 or 2, wherein $R'_0$ is hydrogen, a linear or branched chain alkyl, arylalkyl or aryl group: wherein $R_{10}$, $R_{11}$, $R_{12}$, $R_{13}$, $R_{14}$ and $R_{15}$ are each is independently hydrogen, OH, $OR^{iii}$, $NH_2$, $NHCOR^{iii}$, F, $CH_2OH$, $CH_2OR^{iii}$, or an optionally substituted linear or branched chain lower alkyl, (mono-, di- or tri)hydroxyalkyl, (mono- di- or tri-)acyloxyallcyl, arylalkyl or aryl group; wherein $R_{16}$ is hydrogen, COOH, $COOR^{ii}$, $CONHR^{ii}$, optionally substituted linear or branched chain lower alkyl or aryl group; wherein $R^{iii}$ is hydrogen, CHO, $COOR^{iv}$, or an optionally substituted linear or branched chain alkyl, arylalkyl or aryl group; and wherein $R^{ii}$ and $R^{iv}$ are each independently H, or an optionally substituted linear or branched chain alkyl, arylalkyl or aryl group.

Various proteins are contemplated as being suitable, including bovine serum albumin, KLH, and human serum albumin. Cross linkers suited to the invention are widely known in the art, including bromoacetic NHS ester, 6-(iodoacetamido)caproic acid NHS ester, maleimidoacetic acid NHS ester, maleimidobenzoic acid NHS ester, etc., In one embodiment, the glycoconjugate has the structure:

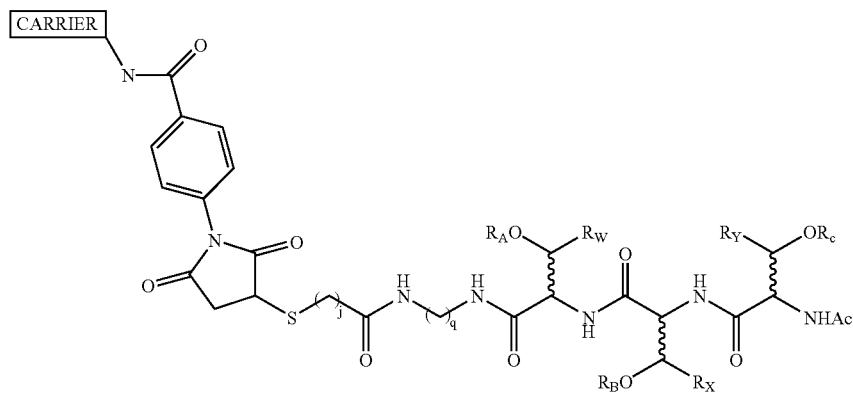

In one embodiment, the invention provides the glycoconjugate wherein $R_V$, $R_W$, $R_X$ and $R_Y$ are methyl. In another embodiment, the invention provides the glycoconjugate wherein the carbohydrate domains are monosaccharides or disaccharides. In another embodiment, the invention provides the glycoconjugate wherein y and z are 0; wherein x is 1; and wherein $R_3$ is NHAc. In a further embodiment, the invention provides the glycoconjugate wherein h is 0; wherein g and i are 1; wherein $R_7$ is OH; wherein $R_0$ is hydrogen; wherein m, n and p are 14; and wherein q is 3; and wherein $R_8$ is hydroxymethyl.

In a certain embodiment, the invention provides the glycoconjugate as disclosed wherein the protein is BSA or KLH. In a preferred embodiment, each amino acyl residue of the glycoconjugate has an L-configuration.

Specific examples of the glycoconjugate contain any of the following carbohydrate domains, which may be either the same or different in any embodiment.

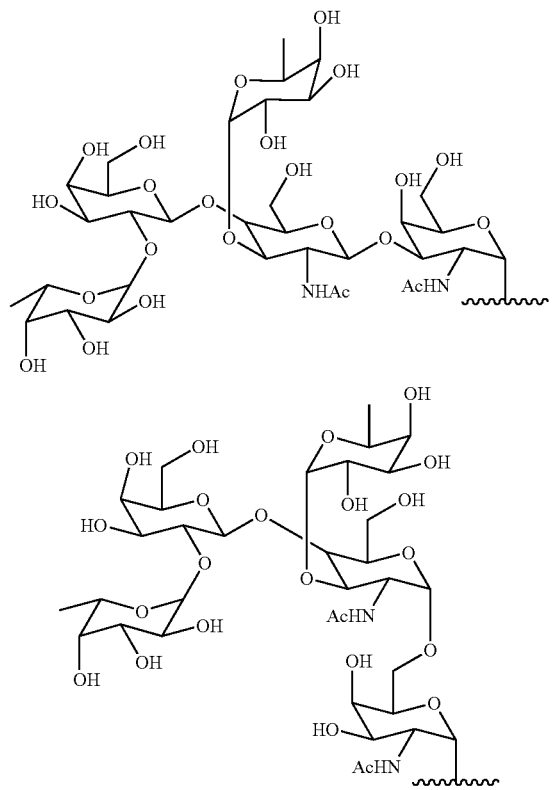
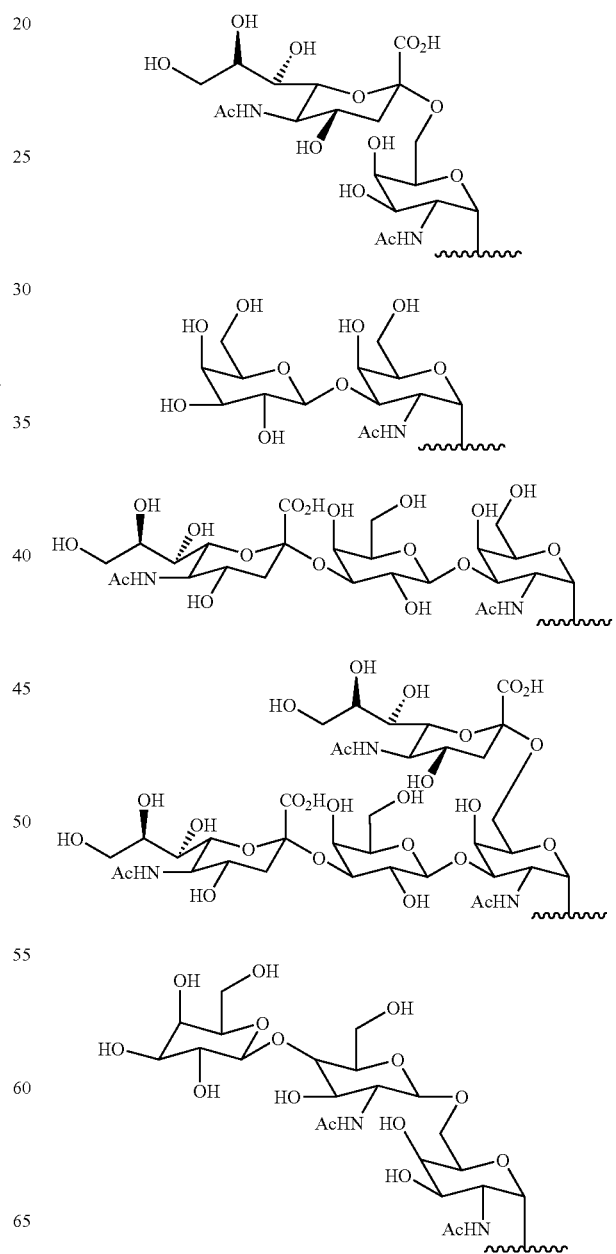

The present invention further provides a pharmaceutical composition for treating cancer comprising a glycoconjugate as above disclosed and a pharmaceutically suitable carrier.

The invention also provides a method of treating cancer in a subject suffering therefrom comprising administering to the subject a therapeutically effective amount of a glycoconjugate disclosed above and a pharmaceutically suitable carrier. In a certain embodiment, the invention provides the method wherein the cancer is a solid tumor. Specifically, the method is applicable wherein the cancer is an epithelial cancer. Particularly effective is the application to treat prostate cancer.

The invention also provides a method of inducing antibodies in a human subject, wherein the antibodies are capable of specifically binding with human tumor cells, which comprises administering to the subject an amount of the glycoconjugate disclosed above effective to induce the antibodies. In a certain embodiment, the invention provides the method wherein the carrier protein is bovine serum albumin, polylysine or KLH.

In addition, the invention provides the related method of inducing antibodies which further comprises co-administering an immunological adjuvant. The adjuvant is preferably bacteria or liposomes. In particular, the adjuvant is *Salmonella minnesota* cells, bacille Calmette-Guerin or QS21. The antibodies induced are favorably selected from the group consisting of Tn, $ST_N$, (2,3)ST, glycophorine, 3-$Le^y$, 6-$Le^y$, T(TF) and T antibodies.

The invention further provides the method of inducing antibodies wherein the subject is in clinical remission or, where the subject has been treated by surgery, has limited unresected disease.

The invention also provides a method of preventing recurrence of epithelial cancer in a subject which comprises vaccinating the subject with the glycoconjugate disclosed above which amount is effective to induce antibodies. The method may be practiced wherein the carrier protein is bovine serum albumin, polylysine or KLH. In addition, the invention provides the related method of preventing recurrence of epithelial cancer which further comprises co-administering an immunological adjuvant. Preferably, the adjuvant is bacteria or liposomes. Specifically, the preferred adjuvant is *Salmonella minnesota* cells, bacille Calmette-Guerin or QS21. The antibodies induced in the practice of the methods are selected from the group consisting of Tn, $ST_N$, (2,3)ST, glycophorine, 3-$Le^y$, 6-$Le^y$, T(TF) and T antibodies.

The present invention also provides a method of preparing a protected O-linked $Le^y$ glycoconjugate having the structure:

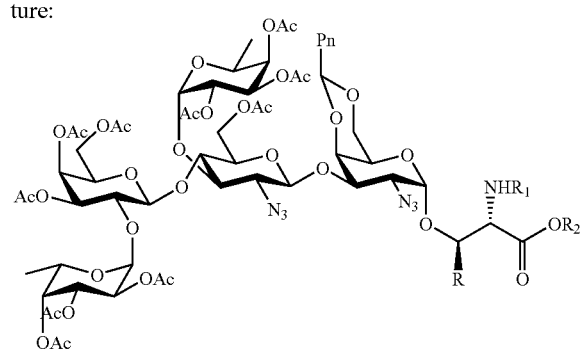

wherein R is hydrogen, linear or branched chain lower alkyl, or optionally substituted aryl; $R_1$ is t-butyloxycarbonyl, fluorenylmethyleneoxycarbonyl, linear or branched chain lower alkyl or acyl, optionally substituted benzyl or aryl; $R_2$ is a linear or branched chain lower alkyl, or optionally substituted benzyl or aryl; which comprises coupling a tetrasaccharide sulfide having the structure:

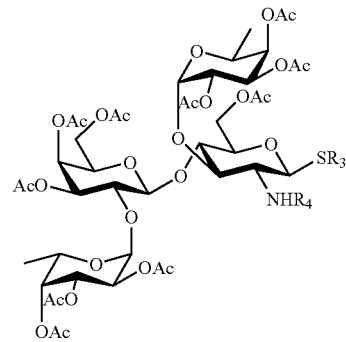

wherein $R_3$ is linear or branched chain lower alkyl or aryl; and $R_4$ is hydrogen, linear or branched chain lower alkyl or acyl, optionally substituted aryl or benzyl: or optionally substituted aryl sulfonyl; with an O-linked glycosul amino acyl component having the structure:

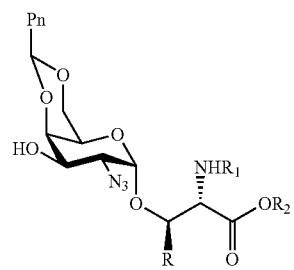

under suitable conditions to form the protected O-linked $Le^y$ glycoconjugate.

In one embodiment of the invention, the tetrasaccharide sulfide shown above may be prepared by (a) halosulfonamidating a tetrasaccharide glycal having the structure:

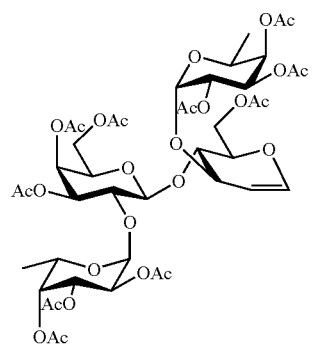

under suitable conditions to form a tetrasaccharide halosulfonamidate; and (b) treating the halosulfonamidate with a mercaptan and a suitable base to form the tetrasaccharide sulfide. In particular, the method may be practiced wherein the mercaptan is a linear or branched chain lower alkyl or an aryl; and the base is sodium hydride, lithium hydride, potassium hydride, lithium diethylamide, lithium diisopropylamide, sodium amide, or lithium hexamethyldisilazide.

The invention also provides an O-linked glycoconjugate prepared by the method disclosed.

In particular, the invention provides an O-linked glycopeptide having the structure:

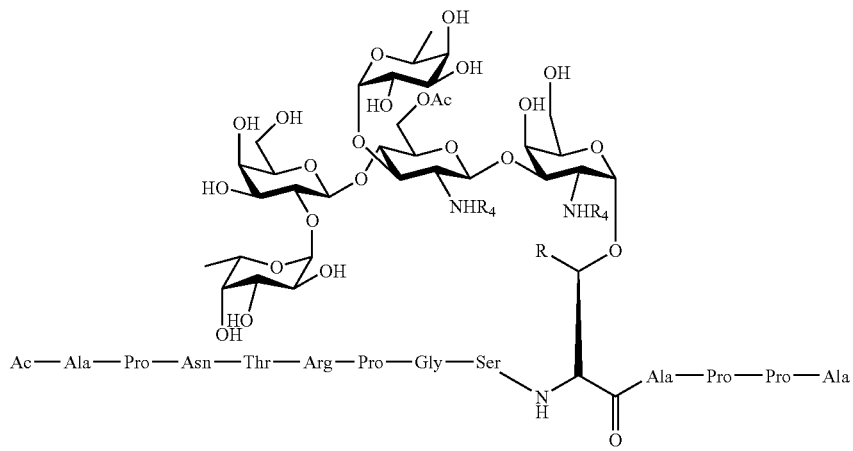

wherein $R_4$ is a linear or branched chain lower acyl; and wherein R is hydrogen or a linear or branched chain lower alkyl or aryl. Variations in the peptidic portion of the glycopeptide are within the scope the invention. In a specific embodiment, the invention provides the O-linked glycopeptide wherein $R_4$ is acetyl.

The present invention provides a method of preparing a protected O-linked Le$^y$ glycoconjugate having the structure:

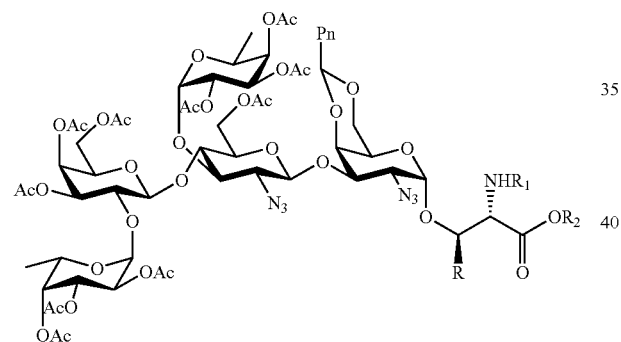

wherein R is hydrogen, linear or branched chain lower alkyl, or optionally substituted aryl; $R_1$ is t-butyloxycarbonyl, fluorenylmethyleneoxycarbonyl, linear or branched chain lower alkyl or acyl, optionally substituted benzyl or aryl; and $R_2$ is a linear or branched chain lower alkyl, or optionally substituted benzyl or aryl; which comprises coupling a tetrasaccharide azidoimidate having the structure:

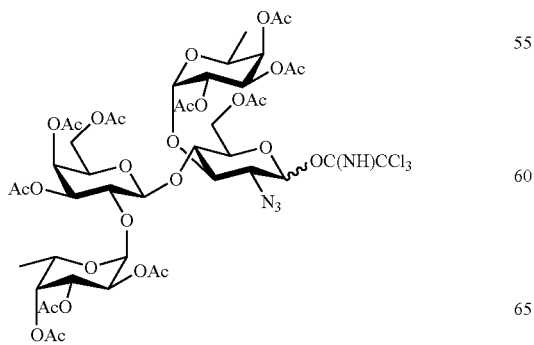

with an O-linked glycosyl amino acyl component having the structure:

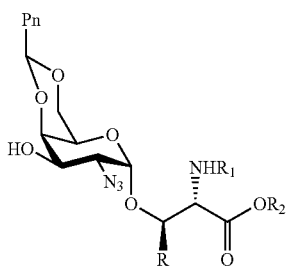

under suitable conditions to form the protected O-linked Le$^y$ glycoconjugate. The tetrasaccharide azidoimidate is favorably prepared by (a) treating a tetrasaccharide having the structure:

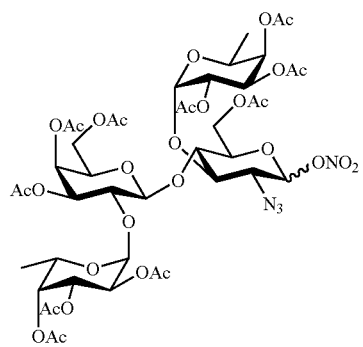

under suitable conditions to form an azido alcohol; and (b) reacting the azido alcohol with an imidoacylating reagent under suitable conditions to form the azidoimidate. The tetrasaccharide azido nitrate may be prepared by (a) converting a tetrasaccharide glycal having the structure:

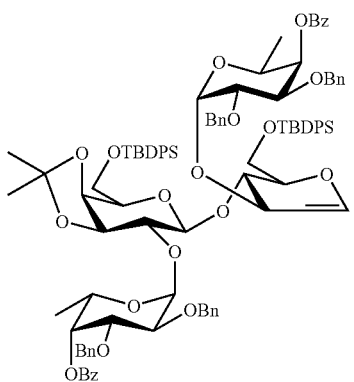

under suitable conditions to form a peracetylated tetrasaccharide glycal having the structure:

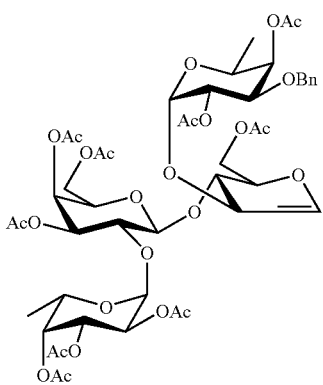

and (b) azidonitrating the glycal formed in step (a) under suitable conditions to form the tetrasaccharide azido nitrate. Step (b) is favorably effected using cerium ammonium nitrate in the presence of an azide salt selected from the group consisting of sodium azide, lithium azide, potassium azide, tetramethylammonium azide and tetraethylammonium azide.

In addition, the invention provides an O-linked glycoconjugate prepared as shown above.

Once the carbohydrate domains covalently linked to O-bearing aminoacyl side chains are prepared, the glycoconjugates of the subject invention may be prepared using either solution-phase or solid-phase synthesis protocols, both of which are well-known in the art for synthesizing simple peptides. Among other methods, a widely used solution phase peptide synthesis method useful in the present invention uses FMOC (or a related carbamate) as the protecting group for the α-amino functional group; ammonia, a primary or secondary amine (such as morpholine) to remove the FMOC protecting group and a substituted carbodiimide (such as N,N'-dicyclohexyl- or -diisopropylcarbodiimide) as the coupling agent for the C to N synthesis of peptides or peptide derivatives in a proper organic solvent. Solution-phase and solid phase synthesis of O-linked glycoconjugates in the N to C direction is also within the scope of the subject invention.

For solid-phase synthesis, several different resin supports have been adopted as standards in the field. Besides the original chloromethylated polystyrene of Merrifield, other types of resin have been widely used to prepare peptide amides and acids, including benzhydrylamine and hydroxymethyl resins (Stewart, *Solid Phase Peptide Synthesis*, Pierce Chemical Co., 1984, Rockford, Ill.; Pietta, et al., *J. Chem. Soc. D.*, 1970, 650–651; Orlowski, et al, *J. Org. Chem.*, 1976, 50, 3701–5; Matsueda et al, Peptides, 1981, 2, 45–50; and Tam, *J. Org. Chem.*, 1985, 50, 5291–8) and a resin consisting of a functionalized polystyrene-grafted polymer substrate (U.S. Pat. No. 5,258,454). These solid phases are acid labile (Albericio, et al., *Int. J. Peptide Research.* 1987, 30, 206–216). Another acid labile resin readily applicable in practicing the present invention uses a trialkoxydi-phenylmethylester moiety in conjunction with FMOC-protected amino acids (Rink, *Tetrahedron Letters*, 1987, 28, 3787–90; U.S. Pat. No. 4,859,736; and U.S. Pat. No. 5,004,781). The peptide is eventually released by cleavage with trifluoroacetic acid. Adaptation of the methods of the invention for a particular resin protocol, whether based on acid-labile or base-sensitive N-protecting groups, includes the selection of compatible protecting groups, and is within the skill of the ordinary worker in the chemical arts.

The glycoconjugates prepared as disclosed herein are useful in the treatment and prevention of various forms of cancer. Thus, the invention provides a method of treating cancer in a subject suffering therefrom comprising administering to the subject a therapeutically effective amount of any of the α-O-linked glycoconjugates disclosed herein, optionally in combination with a pharmaceutically suitable carrier. The method may be applied where the cancer is a solid tumor or an epithelial tumor, or leukemia. In particular, the method is applicable where the cancer is breast cancer, where the relevant epitope may be MBr1.

The subject invention also provides a pharmaceutical composition for treating cancer comprising any of the α-O-linked glycoconjugates disclosed hereinabove, as an active ingredient, optionally though typically in combination with a pharmaceutically suitable carrier. The pharmaceutical compositions of the present invention may further comprise other therapeutically active ingredients.

The subject invention further provides a method of treating cancer in a subject suffering therefrom comprising administering to the subject a therapeutically effective amount of any of the α-O-linked glycoconjugates disclosed hereinabove and a pharmaceutically suitable carrier.

The compounds taught above which are related to α-O-linked glycoconjugates are useful in the treatment of cancer, both in vivo and in vitro. The ability of these compounds to inhibit cancer cell propagation and reduce tumor size in tissue culture will show that the compounds are useful to treat, prevent or ameliorate cancer in subjects suffering therefrom.

In addition, the glycoconjugates prepared by processes disclosed herein are antigens useful in adjuvant therapies as vaccines capable of inducing antibodies immunoreactive with various epithelial tumor and leukemia cells. Such adjuvant therapies may reduce the rate of recurrence of epithelial cancers and leukemia, and increase survival rates after surgery. Clinical trials on patients surgically treated for cancer who are then treated with vaccines prepared from a cell surface differentiation antigen found in patients lacking the antibody prior to immunization, a highly significant increase in disease-free interval may be observed. Cf. P. O. Livingston, et al., *J. Clin. Oncol.*, 1994, 12, 1036.

The magnitude of the therapeutic dose of the compounds of the invention will vary with the nature and severity of the condition to be treated and-with the particular compound and its route of administration. In general, the daily dose range for anticancer activity lies in the range of 0.001 to 25 mg/kg of body weight in a mammal, preferably 0.001 to 10 mg/kg, and most preferably 0.001 to 1.0 mg/kg, in single or multiple doses. In unusual cases, it may be necessary to administer doses above 25 mg/kg.

Any suitable route of administration may be employed for providing a mammal, especially a human, with an effective dosage of a compound disclosed herein. For example, oral, rectal, topical, parenteral, ocular, pulmonary, nasal, etc., routes may be employed. Dosage forms include tablets, troches, dispersions, suspensions, solutions, capsules, creams, ointments, aerosols, etc.

The compositions include compositions suitable for oral, rectal, topical (including transdermal devices, aerosols, creams, ointments, lotions and dusting powders), parenteral (including subcutaneous, intramuscular and intravenous), ocular (ophthalmic), pulmonary (nasal or buccal inhalation) or nasal administration. Although the most suitable route in any given case will depend largely on the nature and severity of the condition being treated and on the nature of the active ingredient. They may be conveniently presented in unit dosage form and prepared by any of the methods well known in the art of pharmacy.

In preparing oral dosage forms, any of the unusual pharmaceutical media may be used, such as water, glycols, oils, alcohols, flavoring agents, preservatives, coloring agents, and the like in the case of oral liquid preparations (e.g., suspensions, elixers and solutions); or carriers such as starches, sugars, microcrystalline cellulose, diluents, granulating agents, lubricants, binders, disintegrating agents, etc., in the case of oral solid preparations are preferred over liquid oral preparations such as powders, capsules and tablets. If desired, capsules may be coated by standard aqueous or non-aqueous techniques. In addition to the dosage forms described above, the compounds of the invention may be administered by controlled release means and devices.

Pharmaceutical compositions of the present invention suitable for oral administration may be prepared as discrete units such as capsules, cachets or tablets each containing a predetermined amount of the active ingredient in powder or granular form or as a solution or suspension in an aqueous or nonaqueous liquid or in an oil-in-water or water-in-oil emulsion. Such compositions may be prepared by any of the methods known in the art of pharmacy. In general compositions are prepared by uniformly and intimately admixing the active ingredient with liquid carriers, finely divided solid carriers, or both and then, if necessary, shaping the product into the desired form. For example, a tablet may be prepared by compression or molding, optionally with one or more accessory ingredients. Compressed tablets may be prepared by compressing in a suitable machine the active ingredient in a free-flowing form such as powder or granule optionally mixed with a binder, lubricant, inert diluent or surface active or dispersing agent. Molded tablets may be made by molding in a suitable machine, a mixture of the powdered compound moistened with an inert liquid diluent.

The present invention will be better understood from the Experimental Details which follow. However, one skilled in the art will readily appreciate that the specific methods and results discussed are merely illustrative of the invention as described in the claims which follow thereafter. It will be understood that the processes of the present invention for preparing α-O-linked glycoconjugates encompass the use of various alternate protecting groups known in the art. Those protecting groups used in the disclosure including the Examples below are merely illustrative.

Experimental Details: General Procedures

All air- and moisture-sensitive reactions were performed in a flame-dried apparatus under an argon atmosphere unless otherwise noted. Air-sensitive liquids and solutions were transferred via syringe or canula. Wherever possible, reactions were monitored by thin-layer chromatography (TLC). Gross solvent removal was performed in vacuum under aspirator vacuum on a Buchi rotary evaporator, and trace solvent was removed on a high vacuum pump at 0.1–0.5 mmHg.

Melting points (mp) were uncorrected and performed in soft glass capillary tubes using an Electrothermal series IA9100 digital melting point apparatus. Infrared spectra (IR) were recorded using a Perkin-Elmer 1600 series Fourier-Transform instrument. Samples were prepared as neat films on NaCl plates unless otherwise noted. Absorption bands are reported in wavenumbers ($cm^1$). Only relevant, assignable bands are reported.

Proton nuclear magnetic resonance ($^1$H NMR) spectra were determined using a Bruker AMX-400 spectrometer at 400 MHz. Chemical shifts are reported in parts per million (ppm) downfield from tetramethylsilane (TMS; $\delta$=0 ppm) using residual $CHCl_3$ as a lock reference ($\delta$=7.25 ppm). Multiplicities are abbreviated in the usual fashion: s=singlet; d=doublet; t=triplet; q=quartet; m=multiplet; br=broad. Carbon nuclear magnetic resonance ($^{13}$C NMR) spectra were performed on a Bruker AMX-400 spectrometer at 100 MHz with composite pulse decoupling. Samples were prepared as with $^1$H NMR spectra, and chemical shifts are reported relative to TMS (0 ppm); residual $CHCl_3$ was used as an internal reference ($\delta$=77.0 ppm). All high resolution mass spectral (HRMS) analyses were determined by electron impact ionization (EI) on a JEOL JMS-DX 303 HF mass spectrometer with perfluorokerosene (PFK) as an internal standard. Low resolution mass spectra (MS) were determined by either electron impact ionization (EI) or chemical ionization (CI) using the indicated carrier gas (ammonia or methane) on a Delsi-Nermag R-10—10 mass spectrometer. For gas chromatography/mass spectra (GCMS), a DB-5 fused capillary column (30 m, 0.25 mm thickness) was used with helium as the carrier gas. Typical conditions used a temperature program from 60–250° C. at 40° C./min.

Thin layer chromatography (TLC) was performed using precoated glass plates (silica gel 60, 0.25 mm thickness). Visualization was done by illumination with a 254 nm UV lamp, or by immersion in anisaldehyde stain (9.2 mL p-anisaldehyde in 3.5 mL acetic acid, 12.5 mL conc. sulfuric acid and 338 mL 95.% ethanol (EtOH)) and heating to colorization. Flash silica gel chromatography was carried out according to the standard protocol.

Unless otherwise noted, all solvents and reagents were commercial grade and were used as received, except as indicated hereinbelow, where solvents were distilled under argon using the drying methods listed in parentheses: $CH_2Cl_2$ ($CaH_2$); benzene ($CaH_2$); THF (Na/ketyl); $Et_2O$ (Na/ketyl); diisopropylamine ($CaH_2$).

| Abbreviations | |
|---|---|
| TLC | thin layer chromatography |
| EtOAc | ethyl acetate |
| TIPS | triisopropylsilyl |
| PMB | p-methoxybenzyl |
| Bn | benzyl |
| Ac | acetate |

-continued

| Abbreviations | |
|---|---|
| hex | hexane |
| THF | tetrahydrofuran |
| coll | collidine |
| LiHMDS | lithium hexamethyldisilazide |
| DMF | N,N-dimethylformamide |
| DMAP | 2-dimethylaminopyridine |
| DDQ | 2,3-dichloro-5,6-dicyano-1,4-benzoquinone |
| TBAF | tetra-n-butylammonium fluoride |
| M.S. | molecular sieves |
| r.t. | room temperature |
| r.b. | round bottom flask |

EXAMPLE 1

2,6-Di-O-acetyl-3,4-O-carbonyl-β-D-galactopyranosyl-(1–3)-6-O-(triisopropylsilyl)-4-O-acetyl-galactal (3). Galactal 2 (1.959 g, 9.89 mmol, 1.2 eq.) was dissolved in 100 mL of anhydrous $CH_2Cl_2$ and cooled to 0° C. Solution of dimethyldioxirane (200 mL of ca 0.06M solution in acetone) was added via cannula to the reaction flask. After 1 hr the starting material was consumed as judged by TLC. Solvent was removed with a stream of $N_2$ and the crude epoxide was dried in vacuo for 1 hr at room temperature. The crude residue (single spot by TLC) was taken up in 33 mL of THF and 6-O-triisopropyl-galactal acceptor (2.50 g, 8.24 mmol) in 20 mL THF was added. The resulting mixture was cooled to −78° C. and $ZnCl_2$ (9.8 mL of 1M solution in ether) was added dropwise. The reaction was slowly warmed up to rt and stirred overnight. The mixture was diluted with EtOAc and washed with sat. sodium bicarbonate, then with brine and finally dried over $MgSO_4$. After evaporation of the solvent the crude material was purified by flash chromatography (40-45-50-60% EtOAc/hexane) to yield pure product which was immediately acetylated. 3.36 g was dissolved in 50 mL of dry $CH_2Cl_2$, triethylamine (19.2 mL), cat amount of DMAP (ca 20 mg) were added and the solution was cooled to 0 C. Acetic anhydride (9.9 mL) was added dropwise at 0° C. The reaction was stirred at rt overnight. The solvent was removed in vacuo and the crude material was chromatographed (50% EtOAc/hexane) to give glycal 3 (3.3 g, 75%): $^1$H NMR (500 MHz, $CDCl_3$) δ 6.42 (d, J=6.3 Hz, 1H, H-1, glycal), 4.35 (½ AB, dd, J=6.8 Hz, 11.5 Hz, 1H, H-6'a), 4.28 (½AB, dd, J=6.1, 11.5 Hz, 1H, H-6'b).

EXAMPLE 2

2,6-Di-O-acetyl-3,4-O-carbonyl-β-D-galactopyranosyl-(1–3)-4-O-acetyl-galactal (4). Compound 3 (1.5 g, 2.43 mmol) was dissolved in 24 mL of THF and cooled to 0° C. A mixture of TBAF (5.8 mL, 5.83 mmol, 2.4 eq.) and acetic acid (336 mL, 2.4 eq.) was added to the substrate at 0° C. The reaction was stirred at 30° C. for 5 hrs. The reaction mixture was diluted with ethyl acetate and quenched with sat sodium bicarbonate. Organic phase was washed with sat sodium bicarbonate, brine and subsequently dried over magnesium sulphate. The crude product was purified by chromatography (80-85-90% EtOAc/hexane) to yield compound 4 (0.9 g, 80%): $^1$H NMR (500 MHz, $CDCl_3$) δ 6.38 (dd, J=1.8, 6.3 Hz, 1H, H-1, glycal), 5.39 (m, 1H, H-4), 2.22 (s, 3H, acetate), 2.16 (s, 3H, acetate), 2.13 (s, 3H, acetate).

EXAMPLE 3

[(Methyl 5-acetamido-4,7,8,9-tetra-O-acetyl-3,5-dideoxy-O-glycero-α-D-galacto-2-nonulopyranosylonate)-(2–6)]-(2,6-di-O-acetyl-3,4-O-carbonyl-β-D-galactopyranosyl)-(1–3)-4-O-acetyl-galactal. (6). A flame dried flask was charged with sialyl phosphite donor 5 (69 mg, 0.11 mmol, 1.3 eq.) and acceptor 4 (40 mg, 0.085 mmol) in the dry box (Argon atmosphere). The mixture was dissolved in 0.6 mL of dry THF. 0.6 mL of dry toluene was added and the solution was slowly cooled to −60° C. to avoid precipitation. Trimethylsilyl triflate (2.4 μL, 0.11 eq.) was added and the mixture was stirred at −45° C. The reaction was quenched at −45° C. after 2 hrs (completion judged by TLC) with 2 mL of sat. sodium bicarbonate, warmed until water melted and the mixture was poured into an excess of ethyl acetate. Organic layer was washed with sat. sodium bicarbonate and dried over anhydrous sodium sulphate. $^1$H NMR of the crude material revealed a 4:1 ratio of α:β isomers (66.4 mg, 84%). The mixture was separated by flash chromatography on silica gel (2-2.5-3-3.5-4% $MeOH/CH_2Cl_2$) to yield compound 6 (50 mg, 63% yield): $^1$H NMR (500 MHz, $CDCl_3$) δ 6.42 (d, J=6.2 Hz, 1H), 5.37 (m, 1H), 5.32–5.29 (m, 4H), 5.26–5.24 (m, 1H), 5.12–5.10 (m, 2H), 4.98 (d, J=3.5 Hz, 1H), 4.92–4.85 (m, 1H), 4.83–4.80 (m, 3H), 4.54 (m, 1H), 4.45 (dd, J=3.0, 13.5 Hz, 1H), 4.33–4.20 (m, 3H), 4.22–4.02 (m, 7H), 3.96 (dd, J=7.6, 10.9 Hz, 1H, H-2), 2.59 (dd, J=4.6, 12.9 Hz, 1H, H-2e NeuNAc), 2.30 (dd, J=12.9 Hz, 1H, H-2ax NeuNAc), 2.16, 2.14, 2.13, 2.12, 2.06, 2.03, 2.02 (s, 7×3H, acetates), 1.88 (s, 3H, CH3CONH); FTIR (neat) 2959.2 (C—H), 1816.5, 1745.0 (C=O), 1683.6, 1662.4 (glycal C=C), 1370.6, 1226.9, 1038.7; HRMS (EI) calc. for C39H51NO25K (M+K) 972.2386. found 972.2407.

EXAMPLE 4

α/β Mixture of azidonitrates 7. Compound 6 (370 mg, 0.396 mmol) was dissolved in 2.2 mL of dry acetonitrile and the solution was cooled to −20° C. Sodium azide ($NaN_3$, 38.6 mg, 0.594, 1.5 eq.) and cerium ammonium nitrate (CAN, 651.3, 1.188 mmol, 3eq.) were added and the mixture was vigorously stirred at −15° C. for 12 hrs. The heterogeneous mixture was diluted with ethyl acetate, washed twice with ice cold water and dried over sodium sulphate to provide 400 mg of the crude product. Purification by flash chromatography provided mixture 7 (246 mg, 60% yield): $^1$H NMR (400 MHz, $CDCl_3$) 6.35 (d, J=4.2 Hz, 1H, H-1, α-nitrate), 3.79 (s, 3H, methyl ester), 3.41 (dd, J=4.7, 11.0, 1H, H-2), 2.54 (dd, J=4.6, 12.8, H-2 eq NeuNAc); FTIR (neat) 2117.4 (N3), 1733.9 (C=O); MS (EI) calc. 1037.8. found 1038.4 (M+H).

EXAMPLE 5

α-Azidobromide 8. A solution of the compound 7 (150 mg, 0.145 mmol) in 0.6 mL of dry acetonitrile was mixed with lithium bromide (62.7 mg, 0.725 mmol, 5 eq.) and stirred at rt for 3 hrs in the dark. The heterogeneous mixture was diluted with dichloromethane and the solution was washed twice with water, dried over magnesium sulphate and the solvent was evaporated without heating. After flash chromatography (5% MeOH, $CH_2Cl_2$) α-bromide 8 (120 mg, 75% yield) was isolated and stored under an argon atmosphere at −80° C.: $^1$H NMR (500 MHz, $CDCl_3$) δ 6.54 (d, J=3.7 Hz, 1H, H-1), 3.40 (dd, J=4.5, 10.8 Hz, 1H, H-2), 2.57 (dd, J=4.5, 12.9, 1H, H-2 eq NeuNAc), 2.20, 2.15, 2.14, 2.12, 2.04, 2.02 (singlets, each 3H, acetates), 1.87 (s, 3H, CH3CONH); MS (EI) calc. for C39H51N4BrO25 1055.7. found 1057.4 (M+H).

EXAMPLE 6

Azido-trichloroacetamidate 9. Compound 7 (600 mg, 0.578 mmol) was dissolved in 3.6 mL of acetonitrile and the resulting solution was treated with thiophenol (180 µL) and diisopropylethylamine (100 µL). After 10 minutes the solvent was removed with a stream of nitrogen. The crude material was purified by chromatography (2-2.5-3-3.5% MeOH/CH$_2$Cl$_2$) to provide 472 mg (82%) of intermediate hemiacetal. 60 mg (0.06 mmol) of this intermediate was taken up in 200 mL of CH$_2$Cl$_2$ and treated with trichloroacetonitrile (60 µL) and 60 mg potassium carbonate. After 6 hrs the mixture is diluted with CH$_2$Cl$_2$, solution is removed with a pipette and the excess K$_2$CO$_3$ was washed three times with CH$_2$Cl$_2$. After evaporation of solvent the crude was purified by flash chromatography (5% MeOH/CH$_2$Cl$_2$) to provide 9 (53.2 mg, 64% yield for two steps, 1:1 mixture of α/β anomers). The anomers can be separated by flash chromatography using a graded series of solvent systems (85-90-95-100% EtOAc/hexane).

EXAMPLE 7

Preparation of glycosyl-L-threonine 13 by AgClO$_4$-promoted glycosidation with glycosyl bromide 8. A flame dried flask is charged with silver perchlorate (27.3 mg, 2 eq), 115 mg of 4 Å molecular sieves and N-FMOC-L-threonine benzyl ester (37.3 mg, 0.086 mmol, 1.2 eq) in the dry box. 0.72 mL of CH$_2$Cl$_2$ was added to the flask and the mixture was stirred at rt for 10 minutes. Donor 8 (76 mg, 0.072 mmol) in 460 µL of CH$_2$Cl$_2$ was added slowly over 40 minutes. The reaction was stirred under argon atmosphere at rt for two hours. The mixture was then diluted with CH$_2$Cl$_2$ and filtered through celite. The precipitate was thoroughly washed with CH$_2$Cl$_2$, the filtrate was evaporated and the crude material was purified on a silica gel column (1-1.5-2-2.5% MeOH/CH$_2$Cl$_2$) to provide 13 (74 mg, 74% yield). The undesired β-anomer was not detected by $^1$H NMR and HPLC analysis of the crude material. 13: $^1$H NMR (500 MHz, CDCl$_3$) δ 7.77 (d, J=7.5 Hz, 2H), 7.63 (d, J=7.2 Hz, 2H), 7.40–7.25 (m, 8H), 5.72 (d, 9.2 Hz, 1H), 5.46 (s, 1H), 5.33 (m, 1H), 5.29 (d, J=8.2 Hz, 1H), 5.23 (s, 2H), 5.11–5.04 (m, 3H), 4.87–4.71 (m, 4H), 4.43–4.39 (m, 3H), 4.33–4.25 (m, 4H), 4.09–3.97 (m, 6H), 3.79 (s, 3H, methyl ester), 3.66 (dd, J=3.7, 10.6 Hz, 1H, H-3), 3.38 (dd, J=3.0, 10.7 Hz, 1H, H-2), 2.52 (dd, J=4.3, 12.7, 1H, H-2 eq NeuNAc), 2.20, 2.13, 2.11, 2.10, 2.04, 2.03, 2.02 (singlets, 3H, acetates), 1.87 (s, 3H, CH3CONH), 1.35 (d, J=6.15 Hz, Thr-CH$_3$); FTIR (neat) 2110.3 (N3), 1748.7 (C=O), 1223.9, 1043.6; HRMS (EI) calc. for C65H75N5O30K (M+K) 1444.4130. found 1444.4155.

EXAMPLE 8

Glycosyl-L-serine 12. BF$_3$.OEt$_2$ promoted glycosydation with trichloroacetamidate 9: A flame dried flask is charged with donor 9 (50 mg, 0.044 mmol), 80 mg of 4 Å molecular sieves and N-FMOC-L-serine benzyl ester (27.5 mg, 0.066 mmol) in the dry box. 0.6 mL of THF was added to the flask and the mixture was cooled to −30° C. BF$_3$.OEt$_2$ (2.8 mL, 0.022 mmol, 0.5 eq.) was added and the reaction was stirred under argon atmosphere. During three hours the mixture was warmed to −10° C. and then diluted with EtOAc and washed with sat sodium bicarbonate while still cold. The crude material was purified on silica gel column (2-2.5-3% MeOH/CH$_2$Cl$_2$) to provide 12 (40 mg, 66% yield) as a 4:1 mixture of α:β isomers. The pure α-anomer was separated by flash chromatography (80-85-90-100% EtOAc/hexane).

EXAMPLE 9

Glycosyl-L-threonine (15). Compound 13 (47 mg, 33.42 µmol) was treated with thiolacetic acid (3 mL, distilled three times) for 27 hrs at rt. Thiolacetic acid was removed with a stream of nitrogen, followed by toluene evaporation (four times). The crude product was purified by flash chromatography (1.5-2-2.5-3-3.5% MeOH/CH$_2$Cl$_2$) to yield 37 mg (78%) of an intermediated which was immediately dissolved in 7.6 mL of methanol and 0.5 mL of water. After purging the system with argon 6.5 mg of palladium catalyst (10% Pd—C) was added and hydrogen balloon was attached. After 8 hrs hydrogen was removed by argon atmosphere, the catalyst was removed by filtration through filter paper and the crude material was obtained upon removal of solvent. Flash Chromatography (10% MeOH/CH$_2$Cl$_2$) provided pure compound 15 (36 mg, 78%): $^1$H NMR (500 MHz, CDCl$_3$) mixture of rotamers, characteristic peaks δ 3.80 (s, 3H, methyl ester), 3.41 (m, 1H, H-2), 2.53 (m, 1H, H-2e NeuNAc)), 1.45 (d, J=5.1 Hz, Thr-CH$_3$), 1.35 (d, J=5.8 Hz, Thr-CH3); FTIR (neat) 1818.2, 1747.2 (C=O), 1371.1, 1225.6, 1045.0; HRMS (EI) calc. for C60H73N3O31K (M+K) 1370.3870. found 1370.3911.

EXAMPLE 10

Glycosyl-L-serine (14). The compound 14 was prepared in 80% yield from 12 following the same procedure as for 15.

EXAMPLE 11

General procedure for peptide coupling:
Glycosyl amino acid 14 or 15 (1 eq) and the peptide with a free amino group (1.2 eq) were dissolved in CH$_2$Cl$_2$ (22 mL/1 mmol). The solution was cooled to 0° C. and IIDQ (1.15–1.3 eq.) is added (1 mg in ca 20 mL CH$_2$Cl$_2$). The reaction was then stirred at rt for 8 hrs. The mixture was directly added to the silica gel column.

EXAMPLE 12

General procedure for FMOC deprotection:
A substrate (1 mmol in 36 mL DMF) was dissolved in anhydrous DMF followed by addition of KF (10 eq) and 18-crown-6 ether (catalytic amount). The mixture was then stirred for 48 hrs at rt. Evaporation of DMF in vacuo was followed by flash chromatography on silica gel.

EXAMPLE 13

Glycopeptide 16. $^1$H NMR (500 MHz, CDCl$_3$) δ 3.45–3.30 (m, 3×1H, H-2), 3.74 (s, 3H, methyl ester), 2.58–2.49 (m, 3×1H, H-2 eq NeuNAc); FTIR (neat) 2961.7, 1819.2, 1746.5, 1663.5, 1370.5, 1225.7, 1042.5; MS (EI) calc. 3760. found 1903.8/doubly charged=3806 (M+2Na).

EXAMPLE 14

Glycopeptide 1. $^1$HNMR (500 MHz, D$_2$O) d 4.73 (m, 2H, 2× H-1), 4.70 (d, 1H, H-1), 4.64 (m, 3H, 3×H-1'), 4.26–4.20

(m, 5H), 4.12–4.00 (m, 7H), 3.95–3.82 (7H), 3.77–3.27 (m, 51H), 2.55–2.51 (m, 3H, 3×H-2 eq NeuNAc), 1.84–1.82 (m, 21H, CH3CONH), 1.52–1.45 (m, 3H, H-2ax NeuNAc), 1.20 (d, J=7.2 Hz, 3H), 1.18 (d, J=6.6 Hz, 3H), 1.12 (d, J=6.2 Hz, 3H), 0.71 (d, J=6.6 Hz, 6H, val); 13C NMR (500 MHz, D2O) anomeric carbons: 105.06, 105.01, 100.60, 100.57, 100.53, 100.11, 99.52, 98.70; MS (FAB) C96H157N11O64 2489 (M+H); MS(MALDI) 2497.

EXAMPLE 15

Glycopeptide 19. MS (EI) calc. for C178H249N15O94Na2 4146 (M+2Na). found 4147, negative ionization mode confirmed the correct mass; MALDI (Matrix Assisted Laser Desorption Ionization) provided masses 4131, 4163.

EXAMPLE 16

Glycopeptide 20 MS (FAB) C119H193N15O70N 2975 (M+Na)

EXAMPLE 17

Preparation of azidonitrates 4': To a solution of protected galactal 3' (4.14 g, 12.1 mmol) in 60 ml of anhydrous $CH_3CN$ at −20° C. was added a mixture of $NaN_3$ (1.18 g, 18.1 mmol) and CAN (19.8 g, 36.2 mmol). The reaction mixture was vigorously stirred at −20° C. for overnight. Then the reaction mixture was diluted with diethyl ether, and washed with cold water and brine subsequently. Finally, the solution was dried over anhydrous $Na_2SO_4$. After evaporation of the solvent, the residue was separated by chromatography on silica gel. A mixture of α- and β-isomers (4') (2.17 g, 40% yield) was obtained. The ratio of α-isomer and β-isomer was almost 1:1 based on $^1H$ NMR. 4a': $[\alpha]_D^{20}$ 94.5° (c 1.14, $CHCl_3$); FT-IR (film) 2940, 2862, 2106, 1661, 1460, 1381, 1278 $cm^{-1}$; $^1H$ NMR (300 MHz, $CDCl_3$) δ 6.34 (d, J=3.9 Hz, 1H), 4.34(m, 2H), 4.21 (t, J=6.4 Hz, 1H), 3.95 (dd, J=9.6, 7.2 Hz, 1H), 3.85 (dd, J=9.6, 6.4 Hz, 1H), 3.78 (m, 1H), 1.52 (s, 3H), 1.35 (s, 3H), 1.04 (m, 21H); $^{13}C$ NMR (75 MHz, $CDCl_3$) δ 110.29, 97.02, 73.36, 71.89, 71.23, 61.95, 59.57, 28.18, 25.96, 17.86, 11.91; HRMS(FAB) calc. for $C_{18}H_{34}N_4O_7SiK$ [M+K$^+$] 485.1833. found 485.1821. 4b': $[\alpha]_D^{20}$ 27.9° (c 1.28, $CHCl_3$); FT-IR (film) 2940, 2862, 2106, 1666, 1459, 1376, 1283 $cm^{-1}$; $^1H$ NMR (300 MHz, $CDCl_3$) δ 5.50 (d, J=8.9 Hz, 1H), 4.30 (dd, J=4.3, 1.5 Hz, 1H), 4.15 (dd, J=6.2, 4.3 Hz, 1H), 3.89–4.03 (m, 3H), 3.56 (dd, J=8.9, 7.3 Hz, 1H), 1.58 (s, 3H), 1.38 (s, 3H), 1.08 (m, 21H); $^{13}C$ NMR (75 MHz, $CDCl_3$) δ 110.90, 98.09, 77.53, 74.58, 71.99, 61.82, 61.68, 28.06, 25.97, 17.85, 11.89; HRMS (FAB) calc. for $C_{18}H_{34}N_4O_7SiK$ [M+K$^+$] 485.1833. found 485.1857.

EXAMPLE 18

Preparation of trichloroacetimidates 5a' and 5b': To a solution of a mixture of azidonitrates (4') (1.36 g, 3.04 mmol) in 10 ml of anhydrous $CH_3CN$ at 0° C. were slowly added Et(i-Pr)$_2$N (0.53 ml, 3.05 mmol) and PhSH (0.94 ml, 9.13 mmol) subsequently. The reaction mixture was stirred at 0° C. for 1 hour, then the solvent was evaporated at room temperature in vacuo. The residue was separated by chromatography on silica gel to give the hemiacetal (1.22 g, 99.8% yield). To a solution of this hemiacetal (603 mg, 1.50 mmol) in 15 ml of anhydrous $CH_2Cl_2$ at 0° C. were added $K_2CO_3$ (1.04 g, 7.50 mmol) and $CCl_3CN$ (1.50 ml, 15.02 mmol). The reaction mixture was stirred from 0° C. to room temperature for 5 hours. The suspension was filtered through a pad of celite and washed with $CH_2Cl_2$. The filtrate was evaporated and the residue was separated by chromatography on silica gel to give α-trichloroacetimidate 5a'(118 mg, 14% yield), β-trichloroacetimidate 5b' (572 mg, 70% yield) and recovered hemiacetal (72 mg). 5a': $[\alpha]_D^{20}$ 84.0° (c 1.02, $CHCl_3$); FT-IR (film) 2942, 2867, 2111, 1675, 1461, 1381, 1244 $cm^{-1}$; $^1H$ NMR (300 MHz, $CDC_{13}$) δ 8.69 (s, 1H), 6.29 (d, J=3.3 Hz, 1H), 4.47 (dd, J=8.0, 5.3 Hz, 1H), 4.39 (dd, J=5.3, 2.4 Hz, 1H), 4.25 (m, 1H), 3.97 (dd, J=9.5, 7.8 Hz, 1H), 3.87 (dd, J=9.5, 6.0 Hz, 1H), 3.67 (dd, J=8.0, 3.3 Hz, 1H), 1.53 (s, 3H), 1.36 (s, 3H), 1.04 (m, 21H); $^{13}C$ NMR (75 MHz, $CDCl_3$) δ 160.67, 109.98, 94.72, 77.20, 73.35, 72.11, 70.83, 62.01, 60.80, 28.29, 26.09, 17.88, 11.88; HRMS (FAB) calc. for $C_{20}H_{35}N_4O_5SiKCl_3$ [M+K$^+$] 583.1080. found 583.1071. 5b': $[\alpha]_D^{20}$ 30.6° (c 1.12, $CHCl_3$); FT-IR (film) 2941, 2110, 1677, 1219 $cm^{-1}$; $^1H$ NMR (300 MHz, $CDC_{13}$)_δ 8.71 (s, 1H), 5.57 (d, J=9.0 Hz, 1H), 4.27 (d, J=5.2 Hz, 1H), 3.95–4.02 (m, 4H), 3.63 (t, J=9.0 Hz, 1H). 1.57 (s, 3H), 1.34 (s, 3H), 1.04 (m, 21H); $^{13}C$ NMR (75 MHz, $CDCl_3$) δ 160.94, 110.55, 96.47, 77.20, 74.58, 72.21, 64.84, 61.89, 28.29, 26.07, 17.87, 11.90; HRMS (FAB) calc. for $C_{20}H_{35}N_4O_5SiKCl_3$ [M+K$^+$] 583.1080. found 583.1073.

EXAMPLE 19

Preparation of glycosyl fluorides 6a' and 6b': To a solution of the hemiacetal prepared previously (68.0 mg, 0.169 mmol) in 3 ml of anhydrous $CH_2Cl_2$ at 0° C. was added DAST (134 ml, 1.02 mmol) slowly. The reaction mixture was stirred at 0° C. for 1 hour. Then the mixture was diluted with EtOAc, washed with sat. $NaHCO_3$ and brine subsequently. Finally, the solution was dried over anhydrous $Na_2SO_4$. After evaporation of the solvent, the residue was separated by chromatography on silica gel to give α-fluoride 6a' (30.2 mg, 44% yield) and β-fluoride 6b' (33.7 mg, 49% yield). 6a': $[\alpha]_D^{20}$ 689.5° (c 1.47, $CHCl_3$); FT-IR (film) 2944, 2867, 2115, 1462, 1381 $cm^{-1}$; $^1H$ NMR (300 MHz, $CDC_{13}$) δ 5.59 (dd, J=53.0, 2.6 Hz, 1H), 4.34–4.40 (m, 2H), 4.26 (m, 1H), 3.96 (t, J=9.3 Hz, 1H), 3.88 (dd, J=9.3, 6.0 Hz, 1H), 3.48 (ddd, J=25.5, 7.0, 2.6 Hz, 1H), 1.50(s, 3H), 1.34 (s, 3H), 1.05 (m, 21H); $^{13}C$ NMR (75 MHz, $CDCl_3$) δ 110.03, 107.45, 104.46, 77.21, 76.38, 73.21, 71.79, 70.48, 61.88, 61.23, 60.91, 28.17, 26.03, 17.09, 11.92; HRMS (FAB) calc. for $C_{18}H_{35}N_3O_4SiF$ [M+H$^+$] 404.2378. found 404.2369. 6b': $[\alpha]_D^{20}$ 153.8° (c 1.65, $CHCl_3$); FT-IR (film) 2943, 2867, 2116, 1456, 1382, 1246 $cm^{-1}$; $^1H$ NMR (300 MHz, $CDCl_3$) δ 5.05 (dd, J=52.6, 7.4 Hz, 1H), 4.27 (dt, J=5.5, 2.0 Hz, 1H), 3.89–4.05 (m, 4H), 3.70 (dt, J=12.3, 5.1 Hz, 1H), 1.53 (s, 3H), 1.32 (s, 3H), 1.04 (m, 21H); $^{13}C$ NMR (75 MHz, $CDCl_3$) δ 110.64, 109.09, 106.24, 76.27, 76.16, 73.42, 71.63, 64.80, 64.52, 61.77, 27.80, 25.78, 17.03, 11.86; HRMS (FAB) calc. for $C_{18}H_{35}N_3O_4SiF$ [M+H$^+$] 404.2378. found 404.2373.

EXAMPLE 20

Coupling of β-trichloroacetimidate 5b' with protected serine derivative 7': synthesis of 9a' and 9b': To a suspension of β-trichloroacetimidate 5b' (52.3 mg, 0.096 mmol), serine derivative 7' (44.0 mg, 0.105 mmol) and 200 mg 4 Å molecular sieve in a mixture of 2 ml of anhydrous $CH_2Cl_2$ and 2 ml of anhydrous hexane at −78° C. was added a solution of TMSOTf (1.91 μl, 0.01 mmol) in 36 μl of $CH_2Cl_2$. The reaction mixture was stirred at −78° C. for a half hour, then warmed up to room temperature for 3 hours.

The reaction was quenched by Et₃N. The suspension was filtered through a pad of celite and washed with EtOAc. The filtrate was washed with H₂O, brine and dried over anhydrous Na₂SO₄. After evaporation of the solvent, the residue was separated by chromatography on silica gel to give α-product 9a' (55 mg, 71% yield) and β-product 9b' (22 mg, 29% yield). 9a': $[\alpha]_D^{20}$ 70.5° (c 2.0, CHCl₃); FT-IR (film) 3433, 3348, 2943, 2867, 2109, 1730, 1504, 1453, 1381, 1336 cm⁻¹; ¹H NMR (300 MHz, CDC₁₃) δ 7.74 (d, J=7.5 Hz, 2H), 7.57 (d, J=7.5 Hz, 2H), 7.25–7.40 (m, 9H), 5.73 (d, J=8.4 Hz, 1H), 5.24 (d, J=12.1 Hz, 1H), 5.17(d, J=12.1, 1H),4.73 (d, J=3.2 Hz, 1H),4.60 (m, 1H), 4.41 (dd, J=10.2, 7.2 Hz, 1H), 4.20–4.31 (m, 4H), 3.82–3.98 (m, 5H), 3.23 (dd, J=8.0, 3.2 Hz, 1H), 1.47 (s, 3H), 1.31 (s, 3H), 1.02 (m, 21H); ¹³C NMR (75 MHz, CDCl₃) δ 169.65, 155.88, 143.81, 143.73, 141.27, 135.04, 128.63, 128.54, 127.71, 127.60, 125.18, 125.11, 109.67, 98.71, 77.23, 72.88, 72.39, 68.95, 68.79, 67.73, 67.36, 62.28, 61.10, 54.39, 47.08, 28.26, 26.10, 17.91, 11.90; HRMS (FAB) calc. for C₄₃H₅₆N₄O₉SiK [M+K⁺] 839.3453. found 839.3466, 839.3453. 9b': $[\alpha]_D^{20}$ 20.6° (c 1.05, CHCl₃); FT-IR (film) 3433, 2943, 2866, 2114, 1729, 1515, 1453, 1382 cm⁻¹; ¹H NMR (300 MHz, CDC₁₃) δ 7.78 (d, J=7.4 Hz, 2H), 7.63 (t, J=7.4 Hz, 2H), 7.30–7.44 (m, 9H), 5.91 (d, J=8.4 Hz, 1H), 5.30 (d, J=12.4 Hz, 1H), 5.26 (d, J=12.4 Hz, 1H), 4.65 (m, 1H), 4.48 (dd, J=10.0, 2.6 Hz, 1H), 4.39 (t, J=7.4 Hz, 2H), 4.23–4.28 (m, 3H), 3.89–4.04 (m, 3H), 3.85 (dd, J=10.0, 3.1 Hz, 1H), 3.78 (m, 1H), 3.41 (t, J=8.2 Hz, 1H), 1.58 (s, 3H), 1.36 (s, 3H), 1.08 (m, 21H); ¹³C NMR (75 MHz, CDCl₃) δ 169.37, 155.92, 143.90, 143.69, 141.25, 135.27, 128.55, 128.27, 127.94, 127.68, 127.07, 125.27, 125.21, 119.94, 110.37, 102.30, 76.87, 73.78, 72.19, 69.68, 67.40, 67.33, 65.44, 61.99, 54.20, 47.06, 28.32, 26.10, 17.89, 11.88; HRMS (FAB) calc. for C₄₃H₅₆N₄O₉SiK [M+K⁺] 839.3453. found 839.3466.

EXAMPLE 21

Coupling of β-trichloroacetimidate 5b' with protected serine derivative 7' in THF promoted by TMSOTf (0.5 eq.): To a suspension of trichloroacetimidate 5b' (14.4 mg, 0.027 mmol), serine derivative 7' (16.7 mg, 0.040 mmol) and 50 mg 4 Å molecular sieve in 0.2 ml of anhydrous THF at −78° C. was added a solution of TMSOTf (2.7 μl, 0.013 mmol) in 50 μl of THF. The reaction was stirred at −78° C. for 2 hours and neutralized with Et₃N. The reaction mixture was filtered through a pad of celite and washed with EtOAc. The filtrate was washed with H₂O, brine and dried over anhydrous Na₂SO₄. After evaporation of the solvent, the residue was separated by chromatography on silica gel to give the a-product 9a' (18.5 mg, 86% yield).

EXAMPLE 22

Coupling of α-trichloroacetimidate 5a with protected serine derivative 7' in THF Promoted by TMSOTf (0.5 eq.): To a suspension of trichloroacetimidate 5a' (12.3 mg, 0.023 mmol), serine derivative 7' (14.1 mg, 0.034 mmol) and 50 mg 4 Å molecular sieve in 0.2 ml of anhydrous THF at −78° C. was added a solution of TMSOTf (2.2 μl, 0.011 mmol) in 45 μl of THF. The reaction was stirred at −78° C. for 4 hours and neutralized with Et₃N. The reaction mixture was filtered through a pad of celite and washed with EtOAc. The filtrate was washed with H₂O, brine and dried over anhydrous Na₂SO₄. After evaporation of the solvent, the residue was separated by chromatography on silica gel to give the α-product 9a' (11.8 mg, 66% yield).

EXAMPLE 23

Coupling of β-trichloroacetimidate 5b' with protected threonine derivative 8: Synthesis of 10a' and 10b': To a suspension of β-trichloroacetimidate 5b' (50.6 mg, 0.093 mmol), threonine derivative 8' (44.0 mg, 0.102 mmol) and 200 mg 4 Å molecular sieve in a mixture of 2 ml of anhydrous CH₂Cl₂ and 2 ml of anhydrous hexane at −78° C. was added a solution of TMSOTf (1.85 μl, 0.009 mmol) in 35 μl of CH₂Cl₂. The reaction mixture was stirred at −78° C. for a half hour, then warmed up to room temperature for 4 hours. The reaction was quenched by Et₃N. The suspension was filtered through a pad of celite and washed with EtOAc. The filtrate was washed with H₂O, brine and dried over anhydrous Na₂SO₄. After evaporation of the solvent, the residue was separated by chromatography on silica gel to give recovered threonine derivative 7' (28.0 mg), the α-product 10a' (22.0 mg, 29% yield) and the β-product 10b' (3.0 mg, 4% yield). 10a': $[\alpha]_D^{20}$ 55.2° (c 0.88, CHCl₃); FT-IR (film) 3430, 2941, 2866, 2109, 1730, 1510, 1452, 1380 cm⁻¹; ¹H NMR (300 MHz, CDC₁₃) δ 7.75 (d, J=7.5 Hz, 2H), 7.59 (d, J=7.5 Hz, 2H), 7.26–7.41 (m, 9H), 5.62 (d, J=9.4 Hz, 1H), 5.22 (d, J=12.3 Hz, 1H), 5.18 (d, J=12.3 Hz, 1H), 4.73 (d, J=3.6 Hz, 1H), 4.36–4.47 (m, 3H), 4.19–4.32 (m, 4H), 4.09 (m, 1H), 3.91 (dd, J=9.8, 6.6 Hz, 1H), 3.83 (dd, J=9.8, 5.5 Hz, 1H), 3.24 (dd, J=8.1, 3.6 Hz, 1H), 1.49 (s, 3H), 1.33 (s, 3H), 1.32 (d, J=6.0 Hz, 3H), 1.05 (m, 21H); ¹³C NMR (75 MHz, CDCl₃) δ 170.12, 156.74, 143.94, 143.69, 141.29, 135.00, 128.65, 128.59, 127.70, 127.10, 125.19, 119.96, 109.78, 99.09, 77.22, 73.16, 72.53, 69.03, 67.71, 67.40, 62.54, 61.61, 58.84, 47.15, 28.32, 26.17, 18.76, 17.94, 11.92; HRMS (FAB) calc. for C₄₄H₅₈N₄O₉SiK [M+K⁺] 853.3608. found 853.3588. 10b': $[\alpha]^{p20}$ 92.4° (c 0.47, CH₂Cl₂); FT-IR (film) 3434, 3351, 2940, 2865, 2111, 1728, 1515, 1455 cm⁻¹; ¹H NMR (300 MHz, CDC₁₃) δ 7.74 (d, J=7.5 Hz, 2H), 7.59 (t, J=7.5 Hz, 2H). 7.25–7.40 (m, 9H), 5.68 (d, J=9.3 Hz, 1H), 5.20 (d, J=12.4 Hz, 1H), 5.17 (d, J=12.4 Hz, 1H), 4.58 (m, 1H), 4.47 (dd, J=9.3, 3.4 Hz, 1H), 4.34 (d, J=7.8 Hz, 2H), 4.18–4.29 (m, 3H), 3.96 (t, J=8.9 Hz, 1H), 3.84 (dd, J=10.0, 5.2 Hz, 1H), 3.81 (dd, J=8.2, 5.2 Hz, 1H), 3.65 (m, 1H), 3.34 (t, J=8.1 Hz, 1H), 1.55 (s, 3H), 1.32 (s, 3H), 1.30 (d, J=6.4 Hz, 3H), 1.02 (m, 21H); ¹³C NMR (75 MHz, CDCl₃) δ 169.89, 156.73, 143.96, 143.73, 141.27, 135.38, 128.61, 128.27, 127.93, 127.67, 127.08, 125.26, 119.93, 110.26, 99.32, 77.91, 77.82, 74.03, 73.55, 72.01, 67.42, 67.25, 65.32, 61.66, 58.61, 47.12, 28.36, 26.08, 17.88, 16.52, 11.87; HRMS(FAB) calc. for C₄₄H₅₈N₄O₉SiNa [M+Na⁺] 837.3869. found 837.3887.

EXAMPLE 24

Coupling of α-glycosyl fluoride 6a' with protected threonine derivative 8' in CH₂Cl₂ promoted by (Cp)₂ZrCl₂—AgClO₄: To a suspension of AgClO₄ (25.1 mg, 0.121 mmol), (Cp)₂ZrCl₂ (17.8 mg, 0.06 mmol) and 150 mg 4 Å molecular sieve in 1 ml of anhydrous CH₂Cl₂ at −30° C. was added a solution of α-glycosyl fluoride 6a' (16.3 mg, 0.04 mmol) and threonine derivative 8' (19.2 mg, 0.045 mmol) in 4.0 ml of anhydrous CH₂Cl₂ slowly. The reaction was stirred at −30° C. for 6 hours and quenched with sat. NaHCO₃. The solution was filtered through a pad of celite and washed with EtOAc. The filtrate was washed with sat. NaHCO₃, brine and dried over anhydrous Na₂SO₄. After evaporation of the solvent, the residue was separated by chromatography on silica gel to give the α-product 10a' (24.8 mg, 75% yield) and the β-product 10b' (3.9 mg, 12% yield).

EXAMPLE 25

Coupling of β-glycosyl fluoride 6b' with protected threonine derivative 8' in $CH_2Cl_2$ promoted by $(Cp)_2ZrCl_2$—$AgClO_4$: To a suspension of $AgCl_4$ (24.4 mg, 0.118 mmol), $(Cp)_2ZrCl_2$ (17.2 mg, 0.059 mmol) and 200 mg 4 Å molecular sieve in 1 ml of anhydrous $CH_2Cl_2$ at −30° C. was added a solution of β-glycosyl fluoride 6b' (15.8 mg, 0.03918 mmol) and threonine derivative 8' (20.3 mg, 0.04702 mmol) in 4.0 ml of anhydrous $CH_2Cl_2$ slowly. The reaction was stirred at −30° C. for 10 hours and quenched with sat. $NaHCO_3$. The solution was filtered through a pad of celite and washed with EtOAc. The filtrate was washed with sat. $NaHCO_3$, brine and dried over anhydrous $Na_2SO_4$. After evaporation of the solvent, the residue was separated by chromatography on silica gel to give the α-product 10a' (22.3 mg, 70% yield) and the β-product 10b' (3.9 mg, 12% yield).

EXAMPLE 26

Deprotection of the silyl group of 9a': To a solution of the α-product 9a' (15.0 mg, 0.01873 mmol) in 2 ml of THF at 0° C. were added HOAc (56 μl, 0.978 mmol) and 1M TBAF (240 μl, 0.240 mmol). The reaction was run at 0° C. for 1 hour, and then warmed up to room temperature for 3 days. The mixture was diluted with EtOAc, washed with $H_2O$, brine, and finally dried over anhydrous $Na_2SO_4$. After evaporation of the solvent, the residue was separated by chromatography on silica gel to give desired product 11' (12.4 mg, 100%). 11': $[\alpha]_D^{20}$ 78.3° (c 0.67, $CH_2Cl_2$); FT-IR (film) 3432, 3349, 2987, 2938, 2109, 1729, 1517, 1452, 1382 cm$^{-1}$; $^1$H NMR (300 MHz, $CDC_{13}$) δ 7.75 (d, J=7.5 Hz, 2H), 7.59 (d, J=7.5 Hz, 2H), 7.27–7.41 (m, 9H), 6.01 (d, J=9.2 Hz, 1H), 5.21 (d, J=12.4 Hz, 1H), 5.18 (d, J=12.4 Hz, 1H), 4.74 (d, J=3.3 Hz, 1H), 4.58 (m, 1H), 4.41 (d, J=7.0 Hz, 2H), 4.14–4.23 (m, 3H), 4.02 (dd, J=5.4, 2.4 Hz, 1H), 3.91–3.97 (m, 2H), 3.68–3.85 (m, 2H), 3.27 (dd, J=8.2, 3.3 Hz, 1H), 1.48 (s, 3H), 1.33 (s, 3H); $^{13}$C NMR (75 MHz, $CDCl_3$) δ 169.71, 155.85, 143.78, 143.71, 141.32, 135.03, 128.59, 127.72, 127.08, 125.08, 119.99, 110.20, 99.12, 77.20, 73.35, 73.11, 70.22, 68.54, 67.76, 67.04, 62.48, 60.73, 54.66, 47.12, 28.10, 26.14; HRMS (FAB) calc. for $C_{34}H_{37}N_4O_9$ [M+H$^+$] 645.2560. found 645.2549.

EXAMPLE 27

Deprotection of the silyl group of 10a': To a solution of the α-product 10a' (16.0 mg, 0.02 mmol) in 3 ml of THF at 0° C. were added HOAc (67 μl, 1.18 mmol) and 1M TBAF (300 μl, 0.3000 mmol). The reaction was run at 0° C. for 1 hour; and then warmed up to room temperature for 3 days. The mixture was diluted with EtOAc, washed with $H_2O$, brine, and finally dried over anhydrous $Na_2SO_4$. After evaporation of the solvent, the residue was separated by chromatography on silica gel to give desired product 12' (12.1 mg, 94%). 12': $[\alpha]_D^{20}$ 731.8° (c 0.62, $CH_2Cl_2$); FT-IR (film) 3430, 2986, 2936, 2109, 1728, 1515, 1451, 1382 cm$^{-1}$; $^1$H NMR (300 MHz, $CDC_{13}$) δ 7.75 (d, J=7.4 Hz, 2H), 7.60 (d, J=7.4 Hz, 2H), 7.25–7.41 (m, 9H), 5.67 (d, J=9.0 Hz, 1H), 5.21 (br.s, 2H), 4.82 (d, J=3.2 Hz, 1H), 4.40–4.52 (m, 3H), 4.33–4.38 (m, 2H), 4.19–4.29 (m, 2H), 4.09 (m, 1H), 3.75–3.92 (m, 2H), 3.30 (dd, J=8.0, 3.2 Hz, 1H), 2.04 (m, 1H), 1.50 (s, 3H), 1.35 (s, 3H), 1.30 (d, J=6.2 Hz, 3H); $^{13}$C NMR (75 MHz, $CDCl_3$) δ 170.13, 156.69, 143.91, 143.69, 141.30, 134.98, 128.61, 127.72, 127.10, 125.20, 119.97, 110.25, 98.39, 76.26, 73.49, 68.35, 67.75, 67.36, 62.62, 61.31, 58.69, 47.16, 28.18, 26.24, 18.54; HRMS (FAB) calc. for $C_{35}H_{39}N_4O_9$ [M+H$^+$] 659.2716. found 659.2727.

EXAMPLE 28

Preparation of compound 14': To a suspension of trichloroacetimidate 13' (332.0 mg, 0.435 mmol), the acceptor 11' (140.2 mg, 0.218 mmol) and 1.0 g 4 Å molecular sieve in 4 ml of anhydrous $CH_2Cl_2$ at −30° C. was added a solution of $BF_3.Et_2O$ (13.8 μl, 0.109 mmol) in 120 μl of anhydrous $CH_2Cl_2$ slowly. The reaction mixture was stirred at −30° C. for overnight, then warmed up to room temperature for 3 hours. The reaction was quenched with $Et_3N$, filtered through a pad of celite and washed with EtOAc. The filtrate was washed with $H_2O$, brine and dried over anhydrous $Na_2SO_4$. After evaporation of the solvent, the residue was separated by chromatography on silica gel to give crude recovered acceptor 11' which was further converted to compound 9a' (87.0 mg, 0.109 mmol) and crude coupling product which was further reduced to compound 14' by pyridine and thiolacetic acid. The crude coupling product was dissolved in 1 ml of anhydrous pyridine and 1 ml of thiolacetic acid at 0° C. The reaction mixture was stirred at room temperature for overnight. The solvent was evaporated in vacuo at room temperature and the residue was separated by chromatography on silica gel to give compound 14' (99.6 mg, 72% yield based on 50% conversion of acceptor 11'). 14': $[\alpha]_D^{20}$ 267.9° (c 4.0, $CHCl_3$); FT-IR (film) 3361, 3018, 1751, 1672, 1543, 1452, 1372 cm$^{-1}$; $^1$H NMR (300 MHz, $CDC_{13}$) δ 7.72 (d, J=7.5 Hz, 2H), 7.58 (m, 2H), 7.26–7.38 (m, 9H), 6.26 (d, J=8.2 Hz, 1H), 5.83 (d, J=9.3 Hz, 1H), 5.59 (d, J=9.2 Hz, 1H), 5.32 (d, J=2.7 Hz, 1H), 5.16 (s, 2H), 5.02–5.11 (m, 2H), 4.94 (dd, J=10.4, 3.4 Hz, 1H), 4.59 (d, J=3.4 Hz, 1H), 4.35–4.52 (m, 6H), 3.60–4.19 (m, 16H), 2.11 (s, 3H), 2.05 (s, 3H), 2.02 (s, 3H), 2.01 (s, 3H), 2.00 (s, 3H), 1.93 (s, 3H), 1.91 (s, 3H), 1.83 (s, 3H), 1.48(s, 3H), 1.24 (s, 3H); $^{13}$C NMR (75 MHz, $CDCl_3$) δ 170.33, 170.23, 170.15, 170.07, 169.94, 169.85, 169.19, 155.92, 143.75, 143.64, 141.22, 135.12, 128.62, 128.39, 127.67, 127.01, 124.99, 119.93, 109.81, 101.12, 100.84, 98.14, 77.21, 75.49, 74.28, 72.61, 72.12, 70.74, 69.10, 68.80, 67.61, 67.38, 67.28, 67.09, 66.64, 62.28. 60.77, 54.25, 53.03, 50.09, 47.09, 27.76, 26.40, 23.18, 23.03, 20.71, 20.47, 20.36; HRMS (FAB) calc. for $C_{62}H_{75}N_3O_{26}Na$ [M+Na$^+$] 1300.4539. found 1300.4520.

EXAMPLE 29

Preparation of Compound 15': To a suspension of trichloroacetimidate 13' (305.0 mg, 0.3996 mmol), the acceptor 12' (131.6 mg, 0.1998 mmol) and 1.0 g 4 Å molecular sieve in 4 ml of anhydrous $CH_2Cl_2$ at −30° C. was added a solution of $BF_3Et_2O$ (12.7 μl, 0.10 mmol) in 115 μl of anhydrous $CH_2Cl_2$ slowly. The reaction mixture was stirred at −30° C. for overnight, then warmed up to room temperature for 3 hours. The reaction was quenched with $Et_3N$, filtered through a pad of celite and washed with EtOAc. The filtrate was washed with $H_2O$, brine and dried over anhydrous $Na_2SO_4$. After evaporation of the solvent, the residue was separated by chromatography on silica gel to give crude recovered acceptor 12' which was further converted to compound 10a' (85.0 mg, 0.104 mmol) and crude coupling product which was further reduced to compound 15' by pyridine and thiolacetic acid. The crude coupling product was dissolved in 1 ml of anhydrous pyridine and 1 ml of thiolacetic acid at 0° C. The reaction mixture was stirred at room temperature for overnight. The solvent was evaporated in vacuo at room temperature and the residue was separated by chromatography on silica gel to give compound 15' (71.1 mg, 58% yield based on 48% conversion of acceptor 12'). 15': $[\alpha]_D^{20}$ 346.8° (c 0.53, CHCl$_3$); FT-IR (film) 3366, 2986, 1750, 1673, 1541, 1452, 1372 cm$^{-1}$; $^1$H NMR (300 MHz, CDC$_{13}$) δ 7.73 (d, J=7.4 Hz, 1H), 7.57 (d, J=7.4 Hz, 2H), 7.27–7.45 (m, 9H), 5.83 (d, J=9.4 Hz, 1H), 5.74 (d, J=9.4 Hz, 1H), 5.61 (d, J=8.9 Hz, 1H), 5.31 (d, J=3.0 Hz, 1H), 4.91–5.16 (m, 5H), 4.62 (d, J=3.2 Hz, 1H), 4.32–4.46 (m, 6H), 3.95–4.22 (m, 11H), 3.64–3.84 (m, 3H), 3.57 (m, 1H), 2.12 (s, 6H), 2.10 (s, 3H), 2.06 (s, 3H), 2.01 (s, 6H), 1.93 (s, 3H), 1.86 (s, 3H), 1.51 (s, 3H), 1.26 (s, 3H), 1.22 (d, J=5.5 Hz, 3H); $^{13}$C NMR (75 MHz, CDCl$_3$) δ 170.70, 170.38, 170.19, 169.94, 169.86, 169.74, 169.20, 156.34, 143.72, 143.59, 141.26, 134.59, 128.74, 128.37, 127.71, 127.03, 124.92, 119.94, 109.76, 101.48, 100.86, 99.48, 77.20, 76.23, 75.49, 74.41, 72.74, 72.43, 70.76, 69.26, 69.13, 67.56, 67.45, 67.13, 66.65, 62.29, 60.78, 58.47, 52.83, 50.35, 47.16, 27.86, 26.54, 23.22, 23.03, 20.72, 20.49, 20.37, 18.20; HRMS (FAB) calc. for C$_{63}$H$_{78}$N$_3$O$_{26}$ [M+H$^+$] 1292.4871. found 1292.4890.

EXAMPLE 30

Synthesis of compound 1': The trisaccharide 14' (105.8 mg, 0.083 mmol) was dissolved in 5 ml of 80% aq. HOAc at room temperature. The reaction mixture was stirred at room temperature for overnight, then at 40° C. for 3 hours. The solution was extracted with EtOAc, washed with sat. NaHCO$_3$, H$_2$O, brine, and dried over anhydrous Na$_2$SO$_4$. After evaporation of the solvent, the residue was separated by chromatography on silica gel to give diol (93.0 mg, 91% yield). To a solution of this diol (91.5 mg, 0.074 mmol) in 10 ml of anhydrous CH$_2$Cl$_2$ at 0° C. were added catalytic DMAP (4.5 mg, 0.037 mmol), Et$_3$N (103 µl, 0.74 mmol) and Ac$_2$O (28 µl, 0.30 mmol) subsequently. The reaction was run for overnight at room temperature. The reaction mixture was diluted with EtOAc, washed with H$_2$O, brine and dried over anhydrous Na$_2$SO$_4$. After evaporation of the solvent, the residue was separated by chromatography on silica gel to give peracetylated compound (88.8 mg, 91% yield). To a suspension of 10% Pd/C (5.0 mg) in a mixture of 1 ml of MeOH and 0.1 ml of H$_2$O was added a solution of the peracetylated compound (38.5 mg, 0.03 mmol) in 4.0 ml of MeOH. The reaction was stirred under H$_2$ atmosphere at room temperature for 4 hours. The reaction mixture was passed through a short column of silica gel to remove the catalyst and washed with MeOH. After removal of the solvent, the residue was dissolved in 1.5 ml of DMF and to this solution was added 0.5 ml of morpholine at 0° C. slowly. The reaction was stirred at room temperature for overnight. The solvent was evaporated in vacuo and the residue was separated by chromatography on silica gel to give 29.0 mg material which was further deacetylated in basic condition. The material got previously was dissolved in 50 ml of anhydrous THF and 5 ml of anhydrous MeOH. The solution was cooled to 0° C. and to this solution was added a solution of NaOMe (14.0 mg, 0.26 mmol) in 5 ml of anhydrous MeOH. The reaction was stirred at room temperature for overnight and quenched with 50% aq. HOAc. After evaporation of the solvent, the residue was separated by chromatography on reverse-phase silica gel to give crude product, which was further purified by gel permeation filtration on Sephadex LH-20 to give the final product 1' (1 5.1 mg, 77% yield). 1': $[\alpha]_D^{20}$ 715.6° (c 0.1, H$_2$O); $^1$H NMR (300 MHz, CD$_3$OD-D$_2$O) δ 4.85 (d, J=3.4 Hz, 1H), 4.55 (d, J=7.4 Hz, 1H), 4.46 (d, J=7.0 Hz, 1H), 4.26 (dd, J=10.9, 3.5 Hz, 1H), 3.34–4.09 (m, 20H), 2.07 (s, 3H), 2.06 (s, 3H); $^{13}$C NMR (75 MHz, CD$_3$OD-D$_2$O) δ 175.64, 175.36, 104.61, 102.98, 99.57, 80.35, 76.94, 76.36, 74.32, 73.88, 72.57, 71.30, 70.82, 70.16, 69.21, 62.50, 61.62, 56.64, 51.58, 51.22, 23.63, 23.40; HRMS(FAB) calc. for C$_{25}$H$_{44}$N$_3$O$_{18}$ [M+H$^+$] 674.2620. found 674.2625.

EXAMPLE 31

Synthesis of Compound 2': The trisaccharide 15' (70.2 mg, 0.054 mmol) was dissolved in 5 ml of 80% aq. HOAc at room temperature. The reaction mixture was stirred at room temperature for overnight, then at 40° C. for 3 hours. The solution was extracted with EtOAc, washed with sat. NaHCO$_3$, H$_2$O, brine, and dried over anhydrous Na$_2$SO$_4$. After evaporation of the solvent, the residue was separated by chromatography on silica gel to give diol (67.1 mg, 99% yield). To a solution of diol (65.1 mg, 0.052 mmol) in 8 ml of anhydrous CH$_2$Cl$_2$ at 0° C. were added catalytic DMAP (3.2 mg, 0.026 mmol), Et$_3$N (72 µl, 0.52 mmol) and Ac$_2$O (20 µl, 0.21 mmol) subsequently. The reaction was run for overnight at room temperature. The reaction mixture was diluted with EtOAc, washed with H$_2$O, brine and dried over anhydrous Na$_2$SO$_4$. After evaporation of the solvent, the residue was separated by chromatography on silica gel to give peracetylated compound (66.0 mg, 95% yield). To a suspension of 10% Pd/C (5.0 mg) in a mixture of 1 ml of MeOH and 0.1 ml of H$_2$O was added a solution of the peracetylated compound (22.1 mg, 0.017 mmol) in 4.0 ml of MeOH. The reaction was stirred under H$_2$ atmosphere at room temperature for 4 hours. The reaction mixture was passed through a short column of silica gel to remove the catalyst and washed with MeOH. After removal of the solvent, the residue was dissolved in 1.5 ml of DMF and to this solution was added 0.5 ml of morpholine at 0° C. slowly. The reaction was stirred at room temperature for overnight. The solvent was evaporated in vacuo and the residue was separated by chromatography on silica gel to give 29.0 mg material which was further deacetylated in basic condition. The material got previously was dissolved in 50 ml of anhydrous THF and 5 ml of anhydrous MeOH. The solution was cooled to 0° C. and to this solution was added a solution of NaOMe (14.9 mg, 0.276 mmol) in 5 ml of anhydrous MeOH. The reaction was stirred at room temperature for overnight and quenched with 50% aq. HOAc. After evaporation of the solvent, the residue was separated by chromatography on reverse-phase silica gel to give crude product, which was further purified by gel permeation filtration on Sephadex LH-20 to give the final product 2' (8.4 mg, 74% yield). 2': $[\alpha]_D^{20}$ 418.4° (c0.1, H$_2$O); $^1$H NMR(300 MHz, CD$_3$O$_D$-D$_2$O) δ 4.91 (d, J=3.3 Hz, 1H), 4.56(d, J=8.2 Hz, 1H), 4.46 (d, J=7.4 Hz, 1H), 3.52–4.22 (m, 20H), 2.10 (s, 3H), 2.06 (s, 3H), 1.36 (d, J=6.5 Hz, 3H); $^{13}$C NMR (75 MHz, CD$_3$OD-D$_2$O) δ 175.90, 175.48, 104.20, 103.97, 102.47, 79.75, 78.71, 76.72, 76.56, 73.92, 73.76, 70.94, 70.52, 70.10, 69.79, 68.98, 62.25, 61.28, 56.25, 51.20, 50.79, 23.51, 19.44; HRMS(FAB) calc. for C$_{26}$H$_{46}$N$_3$O$_{16}$ [M+H$^+$] 688.2776. found 688.2774.

EXAMPLE 32

Preparation of thioglycoside 17': To a suspension of perbenzylated lactal 16' (420 mg, 0.49 mmol) and 600 mg of 4 Å molecular sieve in 5 ml of anhydrous $CH_2Cl_2$ was added benzenesulfonamide (116 mg, 0.74 mmol) at room temperature. After 10 minutes, the suspension was cooled to 0° C. and $I(sym\text{-}collidine)_2ClO_4$ was added in one portion. Fifteen minutes later, the solution was filtered through a pad of celite and washed with EtOAc. The organic solution was washed with $Na_2S_2O_3$, brine and dried over $Na_2SO_4$. After evaporation of the solvent, the residue was separated by chromatography on silica-gel to give 500 mg of iodosulfonamide derivative (90% yield). To a solution of ethanethiol (150 μl, 1.98 mmol) in 4 ml of anhydrous DMF at −40° C. was added a solution of LiHMDS (0.88 ml, 0.88 mmol). After 15 minutes, a solution of iodosulfonamide (450 mg, 0.397 mmol) in 6 ml of anhydrous DMF was added slowly at that temperature. The reaction mixture was stirred at −40° C. for 4 hours, and quenched with $H_2O$. The aqueous solution was extracted by EtOAc three times and the combined organic layer was washed with $H_2O$, brine and dried over $Na_2SO_4$. After evaporation of the solvent, the residue was separated by chromatography on silica gel to give the desired thioglycoside 17' (350 mg, 83% yield) and recover the iodosulfonamide (60 mg). 17': IR (film) 3020, 3000, 2860, 1480, 1450 $cm^{-1}$; $^1H$ NMR (300 MHz, $CDCl_3$) δ 7.87 (d, J=7.7 Hz, 2H), 7.17–7.45 (m, 33H), 5.01 (d, J=8.9 Hz, 1H), 4.93 (d, J=11.4 Hz, 1H), 4.79 (s, 2H), 4.69 (m, 3H), 4.56 (d, J=11.3 Hz, 2H), 4.30–4.50 (m, 6H), 3.95 (t, J=5.0Hz, 1H), 3.90 (d, J=2.7 Hz, 1H), 3.75 (m, 3H), 3.65 (m, 2H), 3.52 (m, 2H), 3.39–3.46 (m, 3H), 2.50 (q, J=7.4 Hz, 2H), 1.12 (t, J=7.4 Hz, 3H); HRMS(FAB) calc. for $C_{62}H_{67}O_{11}NS_2K$ [M+K$^+$]1104.3789. found 1104.3760.

EXAMPLE 33

Preparation of trisaccharide 20': In a round-bottom flask were placed thioglycoside 17'(2.10 g, 1.97 mmol), acceptor 18' (964 mg, 2.95 mmol), di-t-butylpyridine (2.65 ml, 11.81 mmol) and 7.0 g of 4 Å molecular sieve. The mixture was dissolved in 10 ml of anhydrous $CH_2Cl_2$ and 20 ml of anhydrous $Et_2O$. This solution was cooled to 0° C. and then MeOTf (1.11 ml, 8.85 mmol) was added to it slowly. The reaction mixture was stirred at 0° C. for overnight. After filtration through a pad of celite, the organic layer was submitted to aqueous work-up. The EtOAc extraction was dried over $Na_2SO_4$. After evaporation of the solvent, the residue was separated by chromatography on silica gel to give 20α' (206 mg, 8%) and 20β' (2.26 g, 86%). 20β': IR (film) 3020, 3000, 2860, 1480, 1450 $cm^{-1}$; $^1H$ NMR (300 MHz, $CDCl_3$) δ 7.82 (d, J=7.7 Hz, 2H), 7.20–7.45 (m, 43H), 6.32 (d, J=6.2 Hz, 1H), 4.96 (d, J=9.2 Hz 1H), 4.90 (d, J=6.2 Hz, 1H), 4.80 (m, 4H), 4.72 (s, 2H), 4.54–4.68 (m, 6H), 4.28–4.48 (m, 6H), 4.07 (br.s, 1H), 4.00 (t, J=5.0 Hz, 1H), 3.90 (s, 1H), 3.74 (m, 4H), 3.35–3.61 (m, 10H); HRMS (FAB) calc. for $C_{80}H_{83}O_{15}NSK$ [M+K$^+$] 1368.5123. found 1368.5160.

EXAMPLE 34

Preparation of trisaccharide 21': In a round-bottom flask were placed thioglycoside 17' (966 mg, 0.906 mmol), acceptor 19' (219 mg, 1.18 mmol), di-t-butylpyridine (1.22 ml, 5.44 mmol) and 2.5 g of 4 Å molecular sieve. The mixture was dissolved in 5 ml of anhydrous $CH_2Cl_2$ and 10 ml of anhydrous $Et_2O$. This solution was cooled to 0° C. and then MeOTf (0.51 ml, 4.53 mmol) was added to it slowly. The reaction mixture was stirred at 0° C. for 5 hours. After filtration through a pad of celite, the organic layer was submitted to aqueous work-up. The EtOAc extraction was dried over $Na_2SO_4$. After evaporation of the solvent, the residue was separated by chromatography on silica gel to give 21α' (59 mg, 6%) and 21β' (910 mg, 84%). 21α': IR (film) 3020, 3000, 2860, 1480, 1450 $cm^{-1}$; $^1H$ NMR (300 MHz, $CDCl_3$) δ (7.83 (d, J=7.5 Hz, 2H), 7.12–7.46 (m, 33H), 6.36 (d, J=6.2 Hz, 1H), 5.11 (d, J=8.9 Hz, 1H), 4.98 (d, J=10.9 Hz, 1H), 4.93 (d, J=11.6 Hz, 1H), 4.83 (d, J=8.1 Hz, 1H), 4.80 (d, J=11.6 Hz, 1H), 4.68–4.73 (m, 4H), 4.50–4.58 (m, 3H), 4.27–4.32 (m, 4H), 4.27 (d, J=6.2 Hz, 1H), 4.05 (m, 1H), 3.97 (m, 2H), 3.83 (m, 2H), 3.70 (m, 2H), 3.58 (m, 2H), 3.24–3.49 (m, 4H), 1.52 (s, 3H), 1.41 (s, 3H); HRMS(FAB) calc. for $C_{69}H_{75}O_{15}NSNa$ [M+Na$^+$] 1212.4756. found 1212.4720. 21β': IR (film) 3020, 3000, 2860, 1480, 1450 $cm^{-1}$; $^1H$ NMR (300 MHz, $CDCl_3$) δ_(7.87 (d, J=7.2 Hz, 2H), 7.19–7.45 (m, 33H), 6.35 (d, J=6.2 Hz, 1H), 4.98 (d, J=8.9 Hz, 1H), 4.95 (d, J=11.6 Hz, 1H), 4.78 (m, 4H), 4.67 (m, 3H), 4.56 (m, 2H), 4.50 (d, J=12.0 Hz, 1H), 4.43 (d, J=6.2 Hz, 1H), 4.27–4.39 (m, 4H), 4.04 (d, J=6.2 Hz, 1H), 3.97 (t, J=7.2 Hz, 1H), 3.90 (d, J=2.5 Hz, 1H), 3.73–3.82 (m, 3H), 3.48–3.66 (m, 6H), 3.35–3.42 (m, 3H), 1.43 (s, 3H), 1.30 (s, 3H); HRMS(FAB) calc. for $C_{69}H_{75}O_{15}NSNa$ [M+Na$^+$] 1212.4755. found 1212.4780.

EXAMPLE 35

Preparation of trisaccharide 22': In a flame-dried flask was condensed 30 ml of anhydrous $NH_3$ at −78° C. To this liquid $NH_3$ was added sodium metal (320 mg, 13.95 mmol) in one portion. After 15 minutes, the dry ice-ethanol bath was removed and the dark blue solution was refluxed for 20 minutes. It was cooled down to −78° C. again and a solution of trisaccharide 20' (619 mg, 0.47 mmol) in 6 ml of anhydrous THF was added slowly. The reaction mixture was refluxed at −30° C. for half hour and quenched with 10 ml of MeOH. After evaporation of $NH_3$, the basic solution was neutralized by Dowex resin. The organic solution was filtered and evaporated to give crude product which was submitted to acetylation. The crude product was dissolved in 3.0 ml of pyridine and 2.0 ml of $Ac_2O$ in the presence of 10 mg of DMAP at 0° C. The reaction mixture was stirred from 0° C. to room temperature for overnight. After aqueous work-up, the organic layer was dried over $Na_2SO_4$. The solvent was evaporated and the residue was separated by chromatography on silica gel to give peracetylated trisaccharide 22' (233 mg, 59%). 22': $[α]_D^{20}$ −19.77° (c 1.04, $CHCl_3$); IR(film) 1740, 1360 $cm^{-1}$, $^1H$ NMR (300 MHz, $CDCl_3$) δ 6.46 (dd, J=6.2, 1.5 Hz, 1H), 5.64 (d, J=9.1 Hz, 1H), 5.54 (d, J=2.0 Hz, 1H), 5.40 (d, J=4.5 Hz, 1H), 5.36 (d, J=2.9 Hz, 1H), 5.12 (m, 2H), 4.98 (dd, J=10.4, 3.4 Hz, 1H), 4.70 (d, J=6.2 Hz, 1H), 4.58 (d, J=7.3 Hz, 1H), 4.50 (m, 2H), 4.26 (t, J=5.0 Hz, 1H), 4.12 (m, 3H), 3.89 (m, 2H), 3.78 (m, 2H), 3.64 (m, 1H), 2.16 (s, 3H), 2.13 (s, 3H), 2.12 (s, 3H), 2.09 (s, 3H), 2.07 (s, 3H), 2.06 (s, 3H), 2.05 (s, 3H), 2.02 (s, 3H), 1.98 (s, 3H); $^{13}C$ NMR (75 MHz, $CDCl_3$) δ 170.29, 170.14, 169.24, 145.34, 128.20, 100.85, 100.72, 88.86, 75.58, 74.26, 72.58, 72.06, 70.71, 70.61, 68.98, 66.77, 66.55, 64.19, 63.53, 62.09, 60.70, 52.97, 23.05, 20.72, 20.56; HRMS(FAB) calc. for $C_{36}H_{49}O_{22}NNa$ [M+Na$^+$] 870.2645. found 870.2644.

EXAMPLE 36

Preparation of trisaccharide donor 23': To a solution of trisaccharide glycal 20' (460 mg, 0.346 mmol) in 3 ml of anhydrous $CH_3CN$ at −25° C. were added $NaN_3$ (34 mg, 0.519 mmol) and CAN (569 mg, 1.4 mmol) subsequently. The mixture was stirred at −25° C. for 8 hours. After aqueous work-up, the organic layer was dried over $Na_2SO_4$. The solvent was evaporated and the residue was separated by chromatography on silica gel to give a mixture of azidonitrate derivatives (134 mg, 27%). This azidonitrate mixture was hydrolyzed in the reductive condition. The azidonitrates was dissolved in 2 ml of anhydrous $CH_3CN$ at room temperature. $EtN(i-Pr)_2$ (16 µl, 0.091 mmol) and PhSH (28 µl, 0.272 mmol) were added subsequently. After 15 minutes, the reaction was complete and the solvent was evaporated at room temperature. The hemiacetal derivative (103 mg, 74%) was obtained after chromatography on silica gel. This hemiacetal (95 mg, 0.068 mmol) was dissolved in 2 ml of anhydrous $CH_2Cl_2$. To this solution were added 1 ml of $CCl_3CN$ and 0.5 g of $K_2CO_3$ at room temperature. The reaction was run for overnight. After filtration through a pad of celite, the organic solvent was evaporated and the residue was separated by chromatography on silica gel to give 23α' (18 mg, 17%) and 23β' (70 mg, 67%). 23α': $^1H$ NMR (300 MHz, $CDCl_3$) δ 8.71 (s, 1H), 7.96 (d, J=8.2 Hz, 2H), 6.92–7.50 (m, 33H), 6.56 (d, J=2.8 Hz, 1H), 5.02 (m, 3H), 4.92 (d, J=11.6 Hz, 2H), 4.86 (d, J=11.6 Hz, 1H), 4.22–4.64 (m, 18H), 3.95–4.07 (m, 3H), 3.85 (m, 2H), 3.72 (m, 2H), 3.63 (m, 1H), 3.35–3.56 (m, 4H), 3.34 (dd, J=10.3, 2.8 Hz, 1H). 23β': $^1H$ NMR (300 MHz, $CDCl_3$) δ 8.40 (s, 1H), 8.10 (d, J=8.1 Hz, 2H), 6.90–7.45 (m, 33 H), 6.37 (d, J=9.4 Hz, 1H), 5.93 (d, J=8.2 Hz, 1H), 5.04 (d, J=11.6 Hz, 2H), 4.98 (D, J=11.6 Hz 1H), 4.90 (d, J=11.7 Hz, 1H), 4.83 (d, J=11.7 Hz, 1H), 4.79 (d, J=11.6 Hz, 1H), 4.77 (d, j=11.6 Hz, 1H), 4.72 (d, J=8.2 Hz, 1H), 4.40–4.63 (m, 8H), 4.19–4.38 (m, 5H), 3.86–4.10 (m, 6H), 3.63 (m, 2H), 3.42–3.50 (m, 4H), 3.35 (m, 2H), 3.25 (d, J=9.1 Hz, 1H).

EXAMPLE 37

Preparation of trisaccharide donor 24': To a solution of trisaccharide glycal 21' (225 mg, 0.264 mmol) in 2 ml of anhydrous $CH_3CN$ at −15° C. were added $NaN_3$ (26 mg, 0.40 mmol) and CAN (436 mg, 0.794 mmol) subsequently. The mixture was stirred at −15° C. for overnight. After aqueous work-up, the organic layer was dried over $Na_2SO_4$. The solvent was evaporated and the residue was separated by chromatography on silica gel to give a mixture of azidonitrate derivatives (130 mg, 51%). This azidonitrate mixture was hydrolyzed in the reductive condition. The azidonitrates (125 mg, 0.129 mmol) was dissolved in 5 ml of anhydrous $CH_3CN$ at room temperature. $EtN(i-Pr)_2$ (25 µl, 0.147 mmol) and PhSH (45 µl, 0.441 mmol) were added subsequently. After 15 minutes, the reaction was complete and the solvent was evaporated at room temperature. The hemiacetal derivative (92 mg, 77%) was obtained after chromatography on silica gel. This hemiacetal (80 mg, 0.087 mmol) was dissolved in 5 ml of anhydrous $CH_2Cl_2$. To this solution were added 0.9 ml of $CCl_3CN$ and 0.12 g of $K_2CO_3$ at room temperature. The reaction was run for overnight. After filtration through a pad of celite, the organic solvent was evaporated and the residue was separated by chromatography on silica gel to give a mixture of α and β isomer of 24' (71 mg, 77%, α:β 3:1). 24': $^1H$ NMR (300 MHz, $CDCl_3$) δ 9.55 (s, 1H, NH of β isomer), 8.71 (s, 1H, NH of α isomer), 6.54 (d, J=3.6 Hz, amomeric H of α isomer)

EXAMPLE 38

Preparation of trisaccharide donor 25': The azidonitrate derivatives (100 mg, 0.103 mmol) from peracetylated trisaccharide 21' was dissolved in 0.5 ml of anhydrous $CH_3CN$ at room temperature. To this solution was added anhydrous LiBr (45 mg, 0.52 mmol). The mixture was stirred for 3 hours. After aqueous work-up, the solvent was evaporated and the residue was separated by chromatography on silica gel to give compound 25' (91 mg, 90%). 25': $^1H$ NMR (300 MHz, $CDCl_3$) δ 6.04 (d, J=3.6 Hz, 1H, anomeric H).

EXAMPLE 39

Preparation of trisaccharide donor 26': The trisaccharide donor 25' (91 mg, 0.093 mmol) was dissolved in 2 ml of anhydrous THF at 0° C. To this solution was added LiSPh (100 ml, 0.103 mmol). The reaction was run at 0° C. for half hour. The solvent was removed and the residue was separated by chromatography on silica gel to give compound 26' (61 mg, 66%). 26': IR (film) 3000, 2100, 1750, 1680, 1500 $cm^{-1}$; $^1H$ NMR (300 MHz, $CDCl$,) δ 7.61 (m, 2H), 7.39 (m, 3H), 5.50 (d, J=9.1 Hz, 1H), 5.35 (m, 2H), 5.11 (m, 2H), 4.96 (dt, J=10.5, 3.5 Hz, 1H), 4.84 (dd, J=10.2, 3.0 Hz, 1H), 4.50 (m, 4H), 4.16 (m, 3H), 3.59–3.90 (m, 8H), 2.15 (s, 3H), 2.10 (s, 3H), 2.08 (s, 3H), 2.06 (s, 6H), 2.05 (s, 3H), 2.04 (s, 3H), 1.87 (s, 3H).

EXAMPLE 40

Preparation of trisaccharide donor 27': The trisaccharide 21' (860 mg, 0.722 mmol) was dissolved in 2 ml of pyridine and 1 ml of $Ac_2O$ in the presence of 10 mg of DMAP. The reaction was run at 0° C. to room temperature for overnight. After aqueous work-up, the solvent was removed and the residue was dissolved in 10 ml of MeOH and 5 ml of EtOAc at room temperature. To this solution were added $Na_2HPO_4$ (410 mg, 2.89 mmol) and 20% Na—Hg (1.0 g, 4.35 mmol). The reaction was run for 2 hours and aqueous work-up followed. After removal of the organic solvent, the residue was separated by chromatography on silica gel to give N-acetyl trisaccharide glycal (740 mg, 94%). The trisaccharide glycal (624 mg, 0.571 mmol) was dissolved in 3 ml of anhydrous $CH_3CN$ at −40° C. To the solution were added $NaN_3$ (56 mg, 0.86 mmol) and CAN (939 mg, 1.71 mmol) subsequently. The mixture was stirred at −40° C. for 4 hours. After aqueous work-up, the organic solvent was removed and the residue was separated by chromatography on silica gel to give a mixture of α and β azidonitrate anomers (191 mg, 27%). This mixture of anomers (172 mg, 0.137 mmol) was dissolved in 1 ml of $CH_3CN$ at room temperature. To the solution were added $EtN(i-Pr)_2$ (24 µl, 0.137 mmol) and PhSH (42 µl, 0.410 mmol) subsequently. The reaction was complete in half hour and the solvent was blown off. Separation on column afforded desired hemiacetal (170 mg). This hemiacetal was dissolved in 1 ml of $CH_2Cl_2$ at room temperature. To the solution were added 1 ml of $CCl_3CN$ and 500 mg of $K_2CO_3$. The reaction was run at room temperature for overnight. After filtration through a pad of celite, the organic solvent was removed and the residue was separated by chromatography on silica gel to give desired α-trichloroacetimidate 27' (70 mg, 42%). 27': IR (film) 3000, 2120, 1670, 1490, 1450 cm$^{-1}$; $^1$H NMR (300 MHz, CDCl$_3$) δ 8.62 (s, 1H), 7.06–7.48 (m, 30H), 6.44 (d, J=3.0 Hz, 1H), 5.21 (d, J=11.4 Hz, 1H), 5.03 (m, 2H), 4.89 (d, J=11.0 Hz, 1H), 4.80 (d, J=11.3 Hz, 1H), 4,69 (d, J=11.1 Hz, 1H), 4.64 (d, J=7.8 Hz, 1H), 4.44–4.58 (m, 5H), 4.18–4.36 (m, 7H), 3.96–4.08 (m, 3H), 3.72–3.81 (m, 3H), 3.38–3.62 (m, 6H), 3.31 (dd, J=7.0, 2.7 Hz, 1H), 1.59 (s, 3H), 1.31 (s, 3H), 1.14 (s, 3H); HRMS(FAB) calc. for C$_{68}$H$_{74}$O$_{15}$N$_5$Cl$_3$Na [M+Na+] 1316.4145. found 1316.4110.

EXAMPLE 41

Coupling of trisaccharide donor 23α' with methyl N-Fmoc Serinate: To a solution of trisaccharide donor 23α' (70 mg, 0.046 mmol), methyl N-Fmoc serinate (23.4 mg, 0.068 mmol) and 300 mg of 4 Å molecular sieve in 0.5 ml of THF at –78° C. was added TMSOTf (4.6 μl, 0.023 mmol). The reaction was stirred at –35° C. for overnight. The reaction was quenched by Et$_3$N and the solution was filtered through a pad of celite. The filtrate was evaporated and the residue was separated by chromatography on silica gel to give 29α' (70 mg, 90%) and 29β' (7.0 mg, 9.0%).

EXAMPLE 42

Coupling of trisaccharide donor 24' with benzyl N-Fmoc serinate: To a solution of trisaccharide donor 24' (33 mg, 0.030 mmol), benzyl N-Fmoc serinate (33.0 mg, 0.075 mmol) and 100 mg of 4 Å molecular sieve in 0.3 ml of THF at –78° C. was added TMSOTf (6.0 μl, 0.030 mmol). The reaction was stirred from –78° C. to room temperature for 2 hours. The reaction was quenched by Et$_3$N and the solution was filtered through a pad of celite. The filtrate was evaporated and the residue was separated by chromatography on silica gel to give 30' (8.6 mg, 22%, α:β 2:1). 30': IR (film) 3400, 3000, 2100, 1740, 1500 cm$^{-1}$; $^1$H NMR (300 MHz, CDCl$_3$) δ 6.25 (d, J=8.4 Hz, ⅔H), 5.90 (d, J=8.6 Hz, ⅓H), 5.76 (d, J=9.0 Hz, ⅓H), 5.71 (d, J=9.0 Hz, ⅔); MS(CI) 1306 [M$^+$].

EXAMPLE 43

Coupling of trisaccharide donor 25α' with benzyl N-Fmoc serinate: To a solution of benzyl N-Fmoc serinate (45 mg, 0.107 mmol), AgClO$_4$ (37.0 mg, 0.179 mmol) and 200 mg of 4 Å molecular sieve in 0.6 ml of anhydrous CH$_2$Cl$_2$ was added a solution of trisaccharide donor 25α' (88 mg, 0.0893 mmol) in 0.5 ml of CH$_2$Cl$_2$ slowly. The reaction was run at room temperature for overnight. After filtration through a pad of celite, the solvent was removed and the residue was separated by chromatography on silica gel to give the coupling product 30' (66 mg, 56%, α:β 3.5:1).

EXAMPLE 44

Coupling of trisaccharide donor 26β' with benzyl N-Fmoc serinate: To a solution of benzyl N-Fmoc serinate (45 mg, 0.107 mmol), trisaccharide donor 26β' (23 mg, 0.023 mmol) and 50 mg of 4 Å molecular sieve in 1.0 ml of anhydrous CH$_2$Cl$_2$ at 0° C. was added a solution of NIS (6.2 mg, 0.027 mmol) and TfOH (0.24 μl, 0.003 mmol) in 0.5 ml of CH$_2$Cl$_2$ slowly. The reaction was run at 0° C. for 1 hour. The reaction was quenched by Et$_3$N and aqueous work-up followed. The organic solvent was dried over Na$_2$SO$_4$. After removal of the solvent, the residue was separated by chromatography on silica gel to give the coupling product 30' (12.1 mg, 40%, α:β 2:1).

EXAMPLE 45

Coupling of trisaccharide donor 27α' with benzyl N-Fmoc serinate: To a solution of trisaccharide donor 27α' (40.1 mg, 0.029 mmol), benzyl N-Fmoc serinate (18.0 mg, 0.044 mmol) and 200 mg of 4 Å molecular sieve in 2.0 ml of THF at –20° C. was added TMSOTf (1.8 μl, 0.009 mmol). The reaction was stirred from –20° C. to room temperature for 3 hours. The reaction was quenched by Et$_3$N and aqueous work-up followed. After dried over Na$_2$SO$_4$, the filtrate was evaporated and the residue was separated by chromatography on silica gel to give 31' (24 mg, 51%). 31': IR(film) 3000, 2920, 2860, 2100, 1720, 1665, 1500, 1480, 1450 cm$^{-1}$; $^1$H NMR (300 MHz, CDCl$_3$) δ 7.78 (m, 2H), 7.65 (d, J=7.5 Hz, 1H), 7.60 (d, J=7.5 Hz, 1H), 7.20–7.42 (m, 39 H), 6.18 (d, J=7.8 Hz, 1H), 6.05 (d, J=7.3 Hz, 1H), 5.23 (s, 2H), 4.95–5.02 (m, 3H), 4.80 (s, 2H), 4.78 (d, J=2.8 Hz, 1H, anomeric H), 4.72 (s, 2H), 4.58 (m, 4H), 4.37–4.52 (m, 6H), 4.24–4.31 (m, 2H), 4.20 (m, 1H), 4.08 (m, 2H), 3.92–4.02 (m, 5H), 3.78–3.85 (m, 5H), 3.65 (m, 1H), 3.58 (t, J=6.2 Hz, 1H), 3.36–3.46 (m, 5H), 3.26 (dd, J=7.5, 2.8 Hz, 1H), 1.85 (s, 3H), 1.48 (s, 3H), 1.34 (S, 3H); HRMS(FAB) calc. for C$_{90}$H$_{95}$O$_{19}$N$_5$Na [M+Na+]1572.6520. found 1572.6550.

EXAMPLE 46

Coupling of trisaccharide donor 28' with benzyl N-Fmoc serinate: To a solution of trisaccharide donor 28' (α:β 1:1)(162 mg, 0.163 mmol), benzyl N-Fmoc serinate (48.0 mg, 0.097 mmol) and 300 mg of 4 Å molecular sieve in 2.0 ml of THF at –78° C. was added BF$_3$.Et$_2$O (0.5 eq., 0.082 mmol) in CH$_2$Cl$_2$. The reaction was stirred from –78° C. to room temperature for 2 hours. The reaction was quenched by Et$_3$N and aqueous work-up followed. After dried over Na$_2$SO$_4$, the filtrate was evaporated and the residue was separated by chromatography on silica gel to give 32' (81 mg, 67%). 32': IR(film) 3420, 3020, 2940, 2880, 2120, 1745, 1500, 1450 cm$^{-1}$, $^1$H NMR (300 MHz, CDCl$_3$) δ 7.74 (d, J=7.4 Hz, 2H), 7.60 (t, J=7.5 Hz, 2H), 7.20–7.39 (m, 9H), 5.85 (d, J=8.4 Hz, 1H), 5.48 (d, J=12.6 Hz, 1H), 5.32 (d, J=3.4 Hz, 1H), 5.19 (d, J=12.6 Hz, 1H), 5.07 (d, J=8.0 Hz, 1H), 4.90 (dd, J=10.3, 3.4 Hz, 1H), 4.83 (t, J=10.3 Hz, 1H), 4.72 (d, J=9.3 Hz, 1H), 4.67 (d, J=9.6 Hz, 1H), 3.80–4.47 (m, 9H), 3.62 (t, J=9.5 Hz, 1H), 3.32–3.42 (m, 2H), 2.93 (d, J=7.7 Hz, 1H), 2.14 (s, 3H), 2.08 (s, 6H), 2.04 (s, 3H), 2.02 (s, 3H), 1.95 (s, 3H), 1.55 (s, 3H), 1.34 (s, 3H).

EXAMPLE 47

Coupling of trisaccharide donor 28β' with benzyl N-Fmoc serinate: To a solution of trisaccharide donor 28β' (12.0 mg, 0.012 mmol), benzyl N-Fmoc serinate (9.0 mg, 0.022 mmol) and 100 mg of 4 Å molecular sieve in 0.5 ml of THF at –40° C. was added BF$_3$ Et$_2$O (1.5 eq., 0.018 mmol) in CH$_2$Cl$_2$. The reaction was stirred from –40° C. to room temperature for 2 hours. The reaction was quenched by Et$_3$N and aqueous work-up followed. After dried over Na$_2$SO$_4$, the filtrate was evaporated and the residue was separated by chromatography on silica gel to give 32' (5.2 mg, 35%).

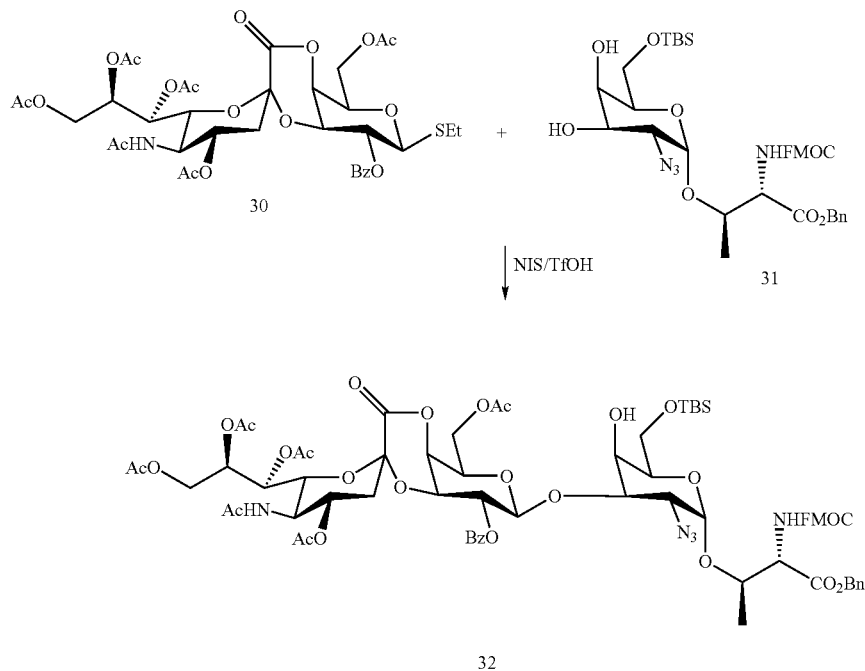

2,3-ST Antigen Precursor

A mixture of thioethyl glycosyl donor 30 (52 mg, 0.064 mmol) and 6-TBDMS acceptor 31 (94 mg, 0.13 mmol) were azeotroped with benzene (4×50 mL), then placed under high vacuum for 1 h. The mixture was placed under nitrogen, at which time 4 Å mol sieves (0.5 g), $CH_2Cl_2$ (5 mL), and NIS (36 mg, 0.16 mmol) were added. The mixture was cooled to 0° C., and trifluoromethanesulfonic acid (1% in $CH_2Cl_2$, 0.96 mL, 0.064 mmol) was added dropwise over 5 min. The suspension was warmed to ambient temperature immediately following addition and stirred 20 min. The mixture was partitioned between EtOAc (50 mL) and sat. $NaHCO_3$ (50 mL). The phases were separated, and the organic phase washed with brine (50 mL), dried ($Na_2SO_4$), and concentrated. The residue was purified by flash chromatography on silica gel (4:1, EtOAc:hexanes) to provide 59 mg (62%) of the trisaccharide 32 as a colorless crystalline solid.

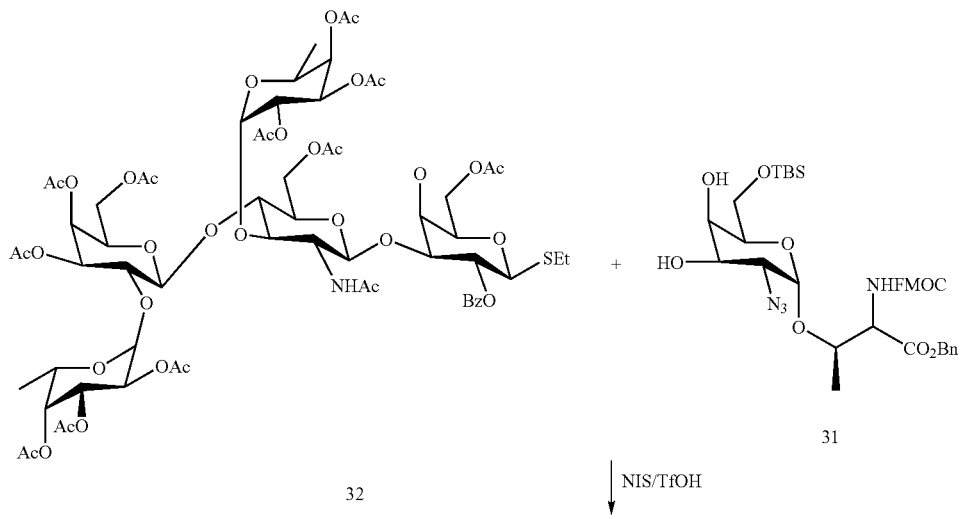

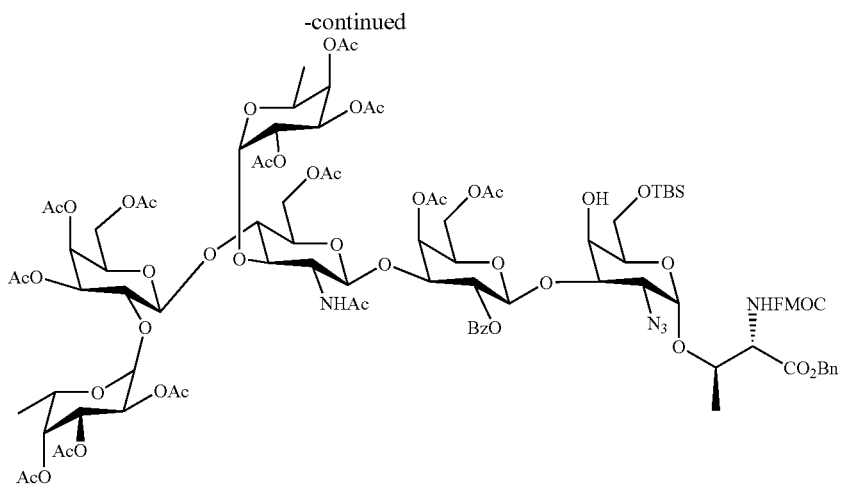

Le$^y$ Antigen Precursor

To thiodonor 32 (44.0 mg, 29.5 µmol) and acceptor 31 (42.4 mg, 59.0 µmol) (azeotroped 3 times with toluene) were added CH$_2$Cl$_2$ and freshly activated 4 Å molecular sieves. The mixture was stirred for 20 min, then cooled to 0° C. N-iodosuccinimide (16.6 mg, 73.8 µmol) was added, followed by the dropwise addition of a 1% solution of TfOH in CH$_2$Cl$_2$. The red mixture was stirred at 0° C. for 5 min, then was diluted with EtOAc. The organic phase was washed with sat. NaHCO$_3$, sat. Na$_2$S$_2$O$_3$, and brine, dried over MgSO$_4$, then concentrated in vacuo. Flash chromatography (1:1 EtOAc/CH$_2$Cl$_2$ to 2:1 EtOAc/CH$_2$Cl$_2$) afforded 43.2 mg (68%) of the coupled product 34.

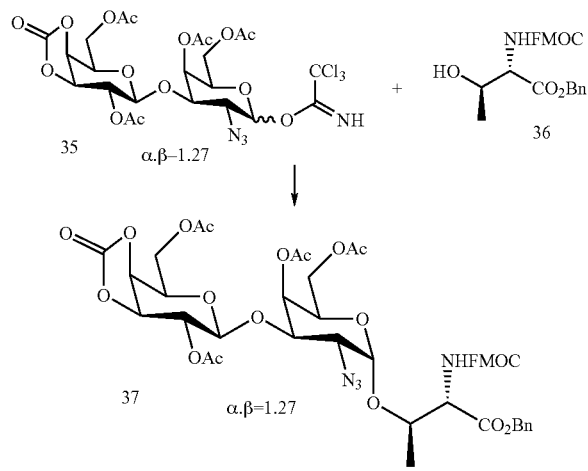

Coupling of b-Trichloroacetimidate with Protected Threonine

To a solution of trichloroacetimidate 35 (98 mg, 0.13 mmol), threonine derivative 36 (70 mg, 0.167 mmol) and 100 mg 4 Å molecular sieve in 6 ml of anhydrous CH$_2$Cl$_2$ at −30° C. was added TMSOTf (14 mL, 0.07 mmol). The reaction was stirred at −30° C. for 1 hour, then neutralized with Et$_3$N. The reaction mixture was filtered through a pad of celite and washed with EtOAc. The filtrate was washed with H$_2$O, brine and dried over anhydrous Na$_2$SO$_4$. After evaporation of the solvent, the residue was separated by chromatography on silica gel to give β-product 37β (56 mg, 42%) and the α-product 37α (57 mg, 42%).

Discussion

The synthetic approach taken in the present invention encompasses four phases (FIG. 2). First, the complete glycodomain is assembled in the form of an advanced glycal. This is followed by efficient coupling to a serine, threonine or analogous residue. The third stage involves peptide assembly incorporating the full glycosyl domain amino acids into the peptide backbone. The concluding phase involves global deprotection either in concurrent or segmental modes.

Figure 3:
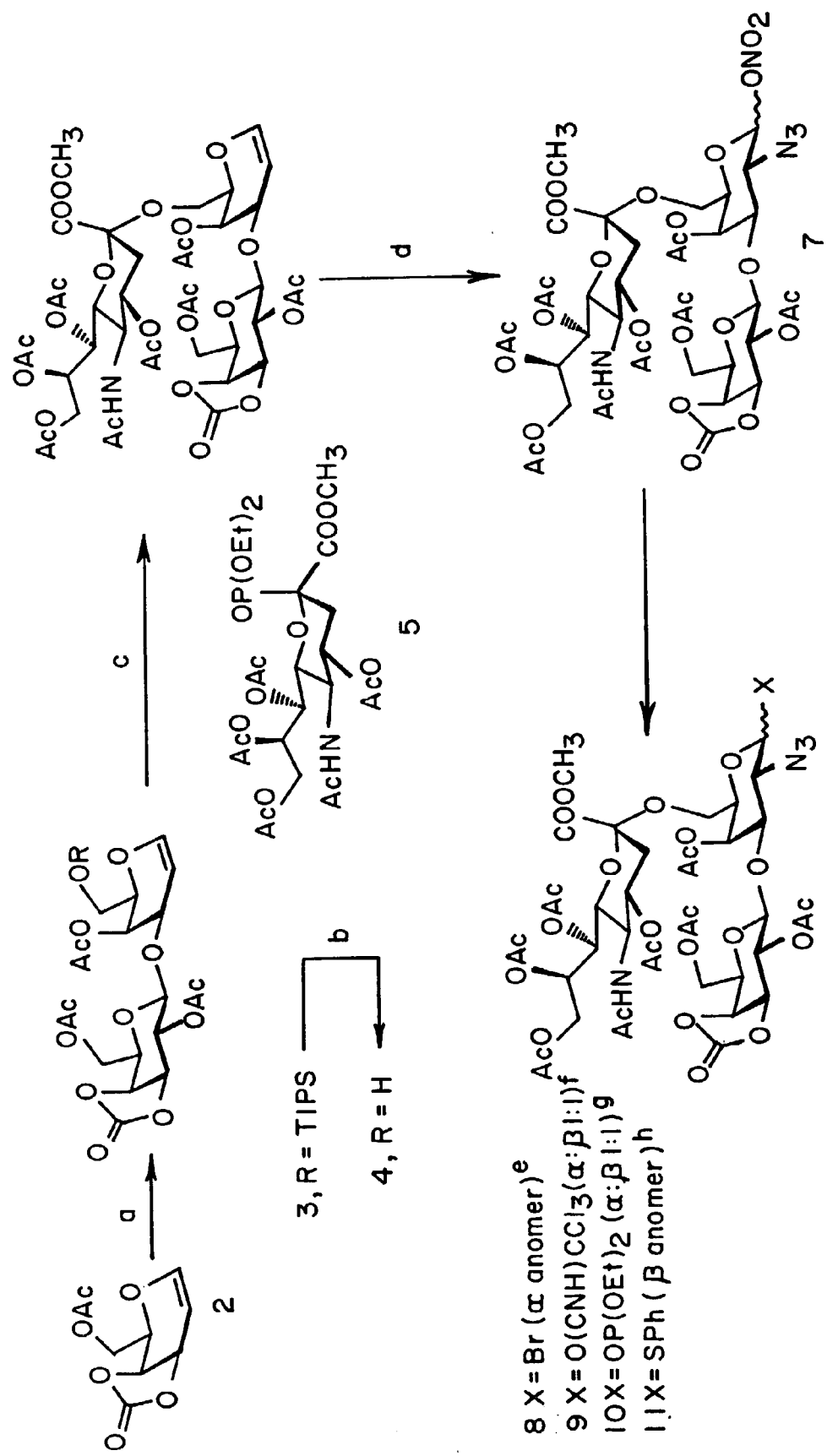
FIG. 3 provides a synthetic route to prepare key intermediate β-phenylthioglycoside 11. Reaction conditions: (a) (1) DMDO, $CH_2Cl_2$; (2) 6-O-TIPS-galactal, $ZnCl_2$, −78° C. to 0° C.; (3) $Ac_2O$, $Et_3N$, DMAP, 75%; (b) TBAF/AcOH/THF; 80%; (c) 5 (1.3 eq), TMSOTf (0.1 eq), THF:Toluene 1:1, −60° C. to −45° C., 84%, α:β 4:1; (d) $NaN_3$, CAN, $CH_3CN$, −15° C., 60%; (e) LiBr, $CH_3CN$, 75%; (f) (1) 1 PhSH, $iPr_2NEt$, $CH_3CN$, 82% (2) $CCl_3CN$, $K_2CO_3$, $CH_2Cl_2$, 80%; (g) (1) PhSH, $iPr_2NEt$; (2) $CIP(OEt)_2$, $iPr_2NEt$, THF, (labile compd, ~72% for two steps); (h) (1) LiBr, $CH_3CN$, 75%; (2) LiSPh, THF, 0° C., 70%).

The synthetic starting point was the readily available glycal 2 (FIG. 3). (Oxidation of this compound with dimethyldioxirane and subsequent coupling of the resultant epoxide with 6-O-TIPS-galactal was promoted by ZnCl$_2$ in the standard way. Toyokuni, T.; Singhal, A. K.; *Chem. Soc. Rev.* 1995, 24, 231. Acetylation of the crude product yielded disaccharide 3 in high yield and stereoselectivity. Removal of the TIPS protecting group under mild conditions set the stage for attachment of sialic acid to acceptor 4. The use of sialyl phosphite 5 as the donor, under promotion of catalytic amounts of TMSOTf, consistently provided high yields (80–85%) of a 4:1 mixture of products. Martin, T. J., et al., *Glycoconjugate J.* 1993, 10, 16. Sim, M. M, et al., *J. Am. Chem. Soc.* 1993, 115, 2260. Thus, the advanced glycal 6 ("2,6-ST glycal") is available in four steps with high efficiency.

The trisaccharide glycal 6 was submitted to azidonitration as shown (FIG. 3). Compound 7 thus obtained in 60% yield lent itself to conversion to a variety of donor constructs (see 8–11). For instance, α-bromide 8 can be used as a donor directly or could be converted to β-phenylthioglycoside 11 with lithium thiophenoxide in a stereoselective manner. Alternatively, mixtures of nitrates 7 was hydrolyzed and the resulting hemiacetal converted to 1:1 mixture of α:β trichloroacetamidates (9) and diethylphoshites (10) in high yields (FIG. 3). (Nitrate hydrolysis: Gauffeny, F., et al., *Carbohydr. Chem.* 1991, 219, 237. Preparation and application of trichloroacetamidates: Schmidt, R. R. and Kinzy, W.; *Adv. Carbohydr. Chem. Biochem.* 1994, 50, 21. Phosphite donors: Kondo, H., et al.; *J. Org. Chem.* 1994, 59, 864.)

TABLE I

Reaction of 11 with N-FMOC-Ser(OH)—OBn.

| X (11) | Catalyst/Promoter | R = H (12) α:β(%) | R = CH$_3$ (13) α:β(%) |
|---|---|---|---|
| —Br (8α) | AgClO$_4$(1.5 eq), CH$_2$Cl$_2$, rt | 2.6:1 (70%) | α only (74%) |
| —O(CNH)CCl$_3$ (9β) | BF$_3$OEt$_2$(0.5 eq), THF, -30 C | 12:1 (65%) | α only (63%) |
| —O(CNH)CCl$_3$ (9αβ 1:1) | BF$_3$OEt$_2$(0.5 eq), THF, -30 C | 4:1 (66%) | α only (60%) |
| —OP(OEt)$_2$ (10αβ 1:1) | BF$_3$OEt$_2$(0.5 eq), THF, -30 C | 30:1 (30%) | — |

The availability of various donor types (8–11) enabled the investigation of the direct coupling of (2,6)-ST trisaccharide to benzyl ester of N-Fmoc-protected L-serine and L-threonine. The results are summarized in Table 1. As with Fmoc protected L-threonine as the acceptor, all of the donors afforded the α-O glycosyl threonine system in high stereoselectivity. By contrast, the outcome of the coupling reactions with similarly protected L-serine acceptors was dependent on the character of the donor and on the reaction conditions. In all cases, the desired α-anomer 12 was the major product. (For previous attempts to couple a trisaccharide donor to serine, in which β-anomers were isolated as the major products, see: Paulsen, H. et al., *Liebigs Ann. Chem.* 1988, 75; Iijima, H.; Ogawa, T., *Carbohydr. Res.* 1989, 186, 95.) With donor 10 the ratio of desired α-product:undesired β-glycoside was ca 30:1.

Figure 4A:
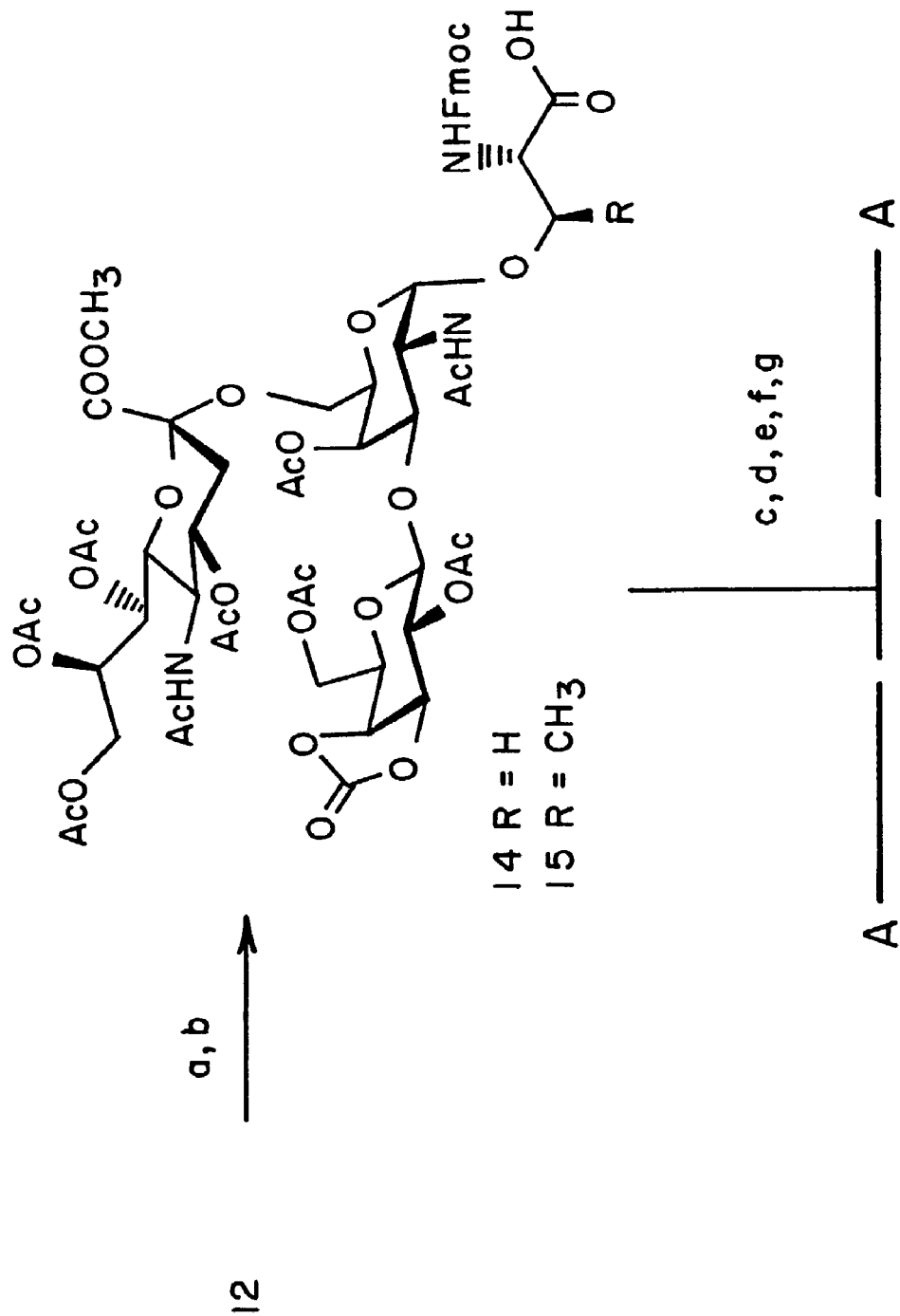
FIG. 4 presents a synthetic route to glycoconjugate mucin 1. Reaction conditions: (a) $CH_3COSH$, 78%; (b) $H_2$/10% Pd—C, MeOH, $H_2O$, quant.; (c) $H_2N$-Ala-Val-OBn, IIDQ, $CH_2Cl_2$, 85%; (d) KF, DMF, 18-crown-6, 95%; (e) 15, IIDQ, 87%; (f) KF, DMF, 18-crown-6, 93%; (g) 14, IIDQ, 90%; (h) (1) KF, DMF, 18-crown-6; (2) $Ac_2O$, $CH_2Cl_2$,; (i) $H_2$/10% Pd—C, MeOH, $H_2O$, 92% (three steps); (j) NaOH, $H_2O$, 80%.
Figure 4B:
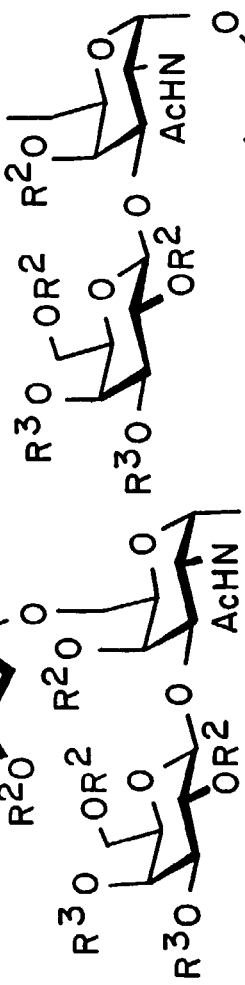

The glycopeptide assembly phase was entered with building units 14 and 15, thereby reducing the number of required chemical operations to be performed on the final glycopeptide. Thus, compounds 14 and 15 were obtained in two steps from 12 and 13, respectively. The azide functionality was transformed directly to N-acetyl groups by the action of CH$_3$COSH in 78–80% yield and the benzyl ester was removed quantitatively by hydrogenolysis (FIG. 4). Paulsen, H., et al., *Liebigs Ann. Chem.* 1994, 381.

The glycopeptide backbone was built in the C→N-terminus direction (FIG. 4). Iteration of the coupling step between the N-terminus of a peptide and protected glycosyl amino acid, followed by removal of the FMOC protecting group provided protected pentapeptide 16. The peptide coupling steps of block structures such as 12 and 13 proceeded in excellent yields. Both IIDQ and DICD coupling reagents work well (85–90%). FMOC deprotection was achieved under mild treatment with KF in DMF in the presence of 18-crown-6. Jiang, J., et al., *Synth. Commun.* 1994, 24, 187. The binal deblocking of glycopeptide 16 was accomplished in three stages: (i) Fmoc removal with KF and protection of the amino terminus with acetyl group; (ii) hydrogenolysis of the benzyl ester; and (iii) final saponification of three methyl esters, cyclic carbonates and acetyl protection with aqueous NaOH leading to glycopeptide mucin model 1 (FIG. 4).

Figure 5A:
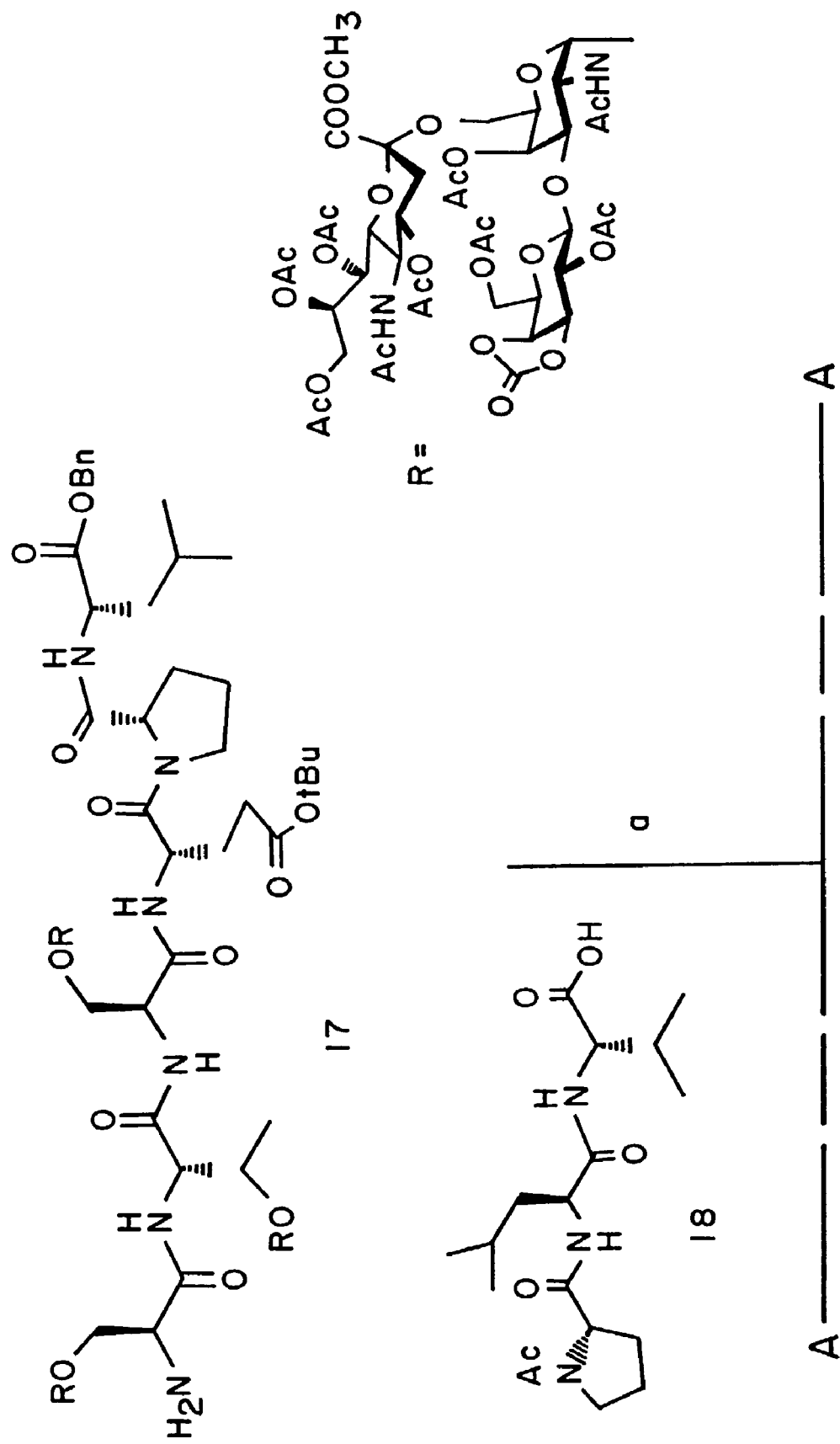
FIG. 5 shows a synthetic route to prepare glycoconjugates by a fragment coupling. Reagents: (a) IIDQ, $CH_2Cl_2$, rt, 80%; (b) $H_2$/Pd—C, MeOH, $H_2O$, 95%; (c) $CF_3COOH$, $CH_2Cl_2$; (d) NaOH, $H_2O$, MeOH.
Figure 5B:
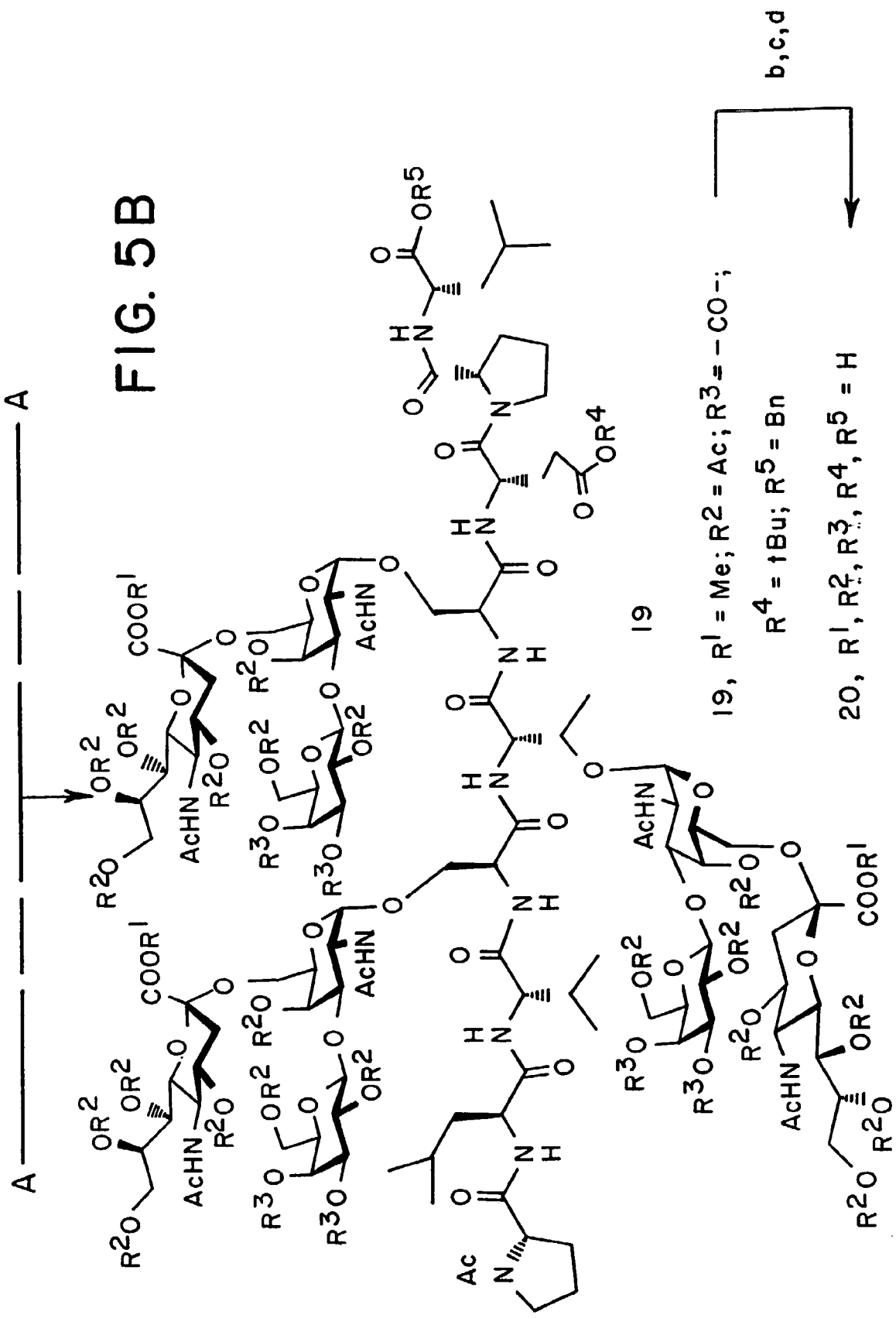
Figure 6:
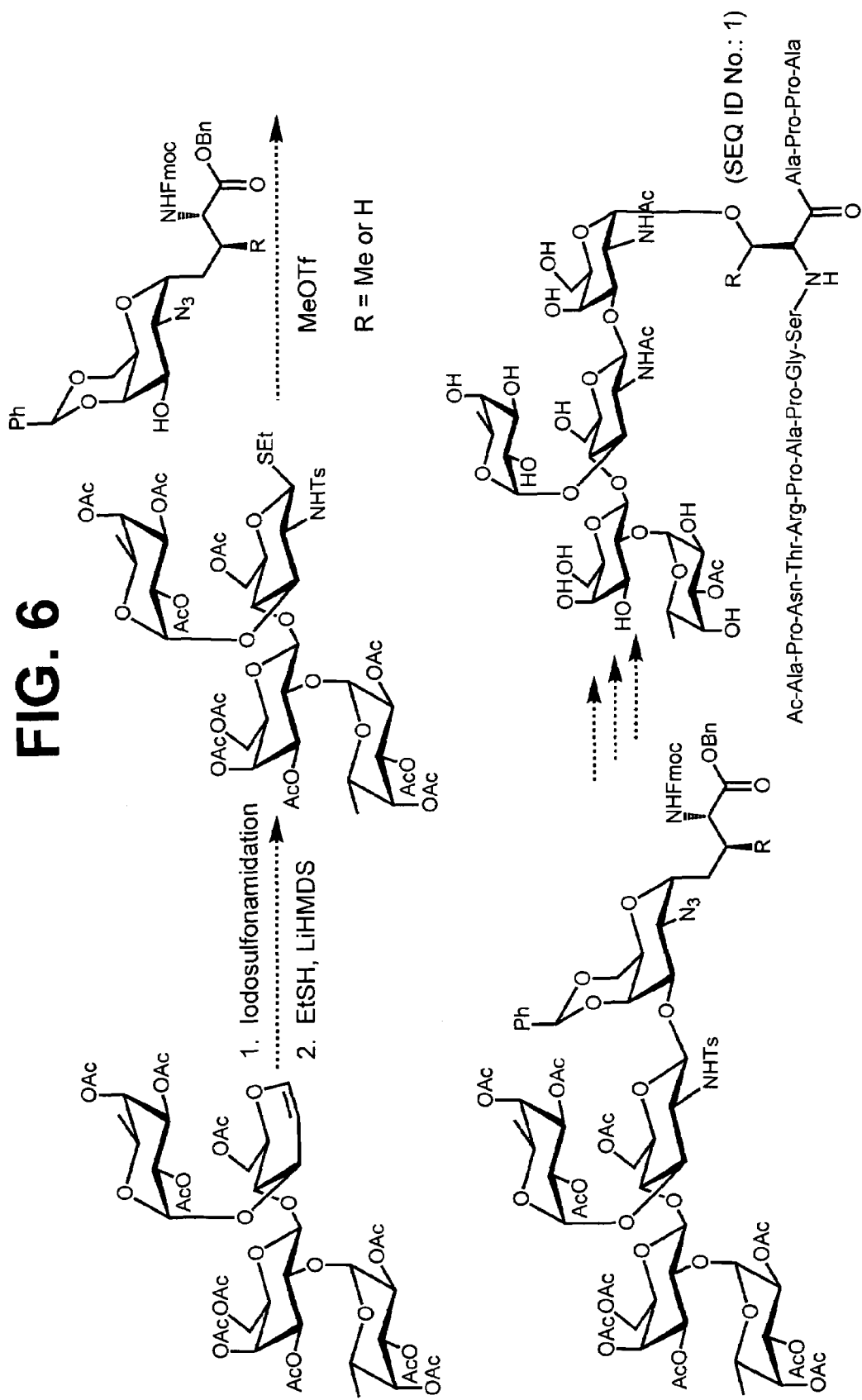
FIG. 6 shows the synthesis of α-O-linked glycopeptide conjugates of the $Le^y$ epitope via an iodosulfonamidation/4+2 route.
Figure 7A:
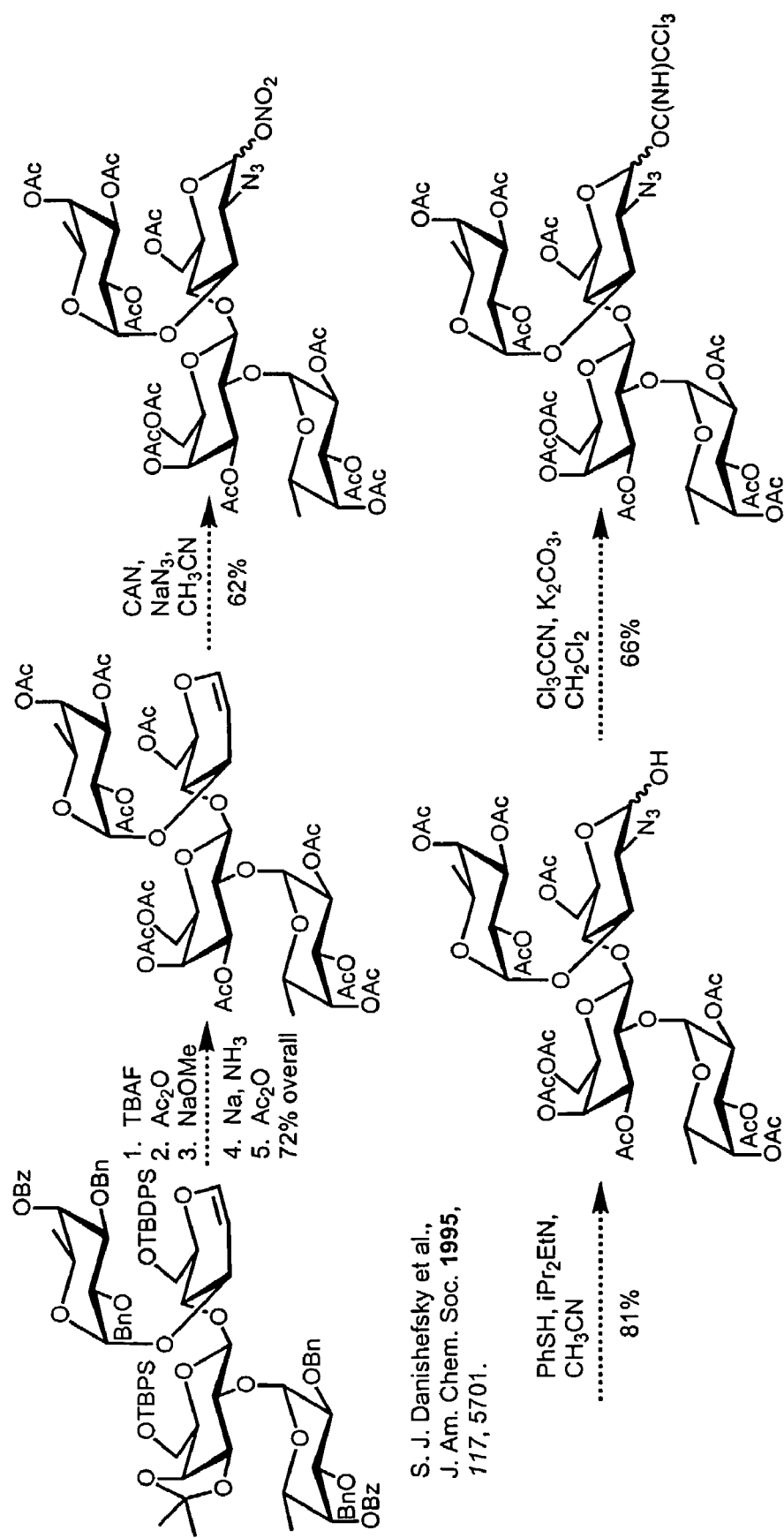
FIG. 7 provides the synthesis of α-O-linked glycopeptide conjugates of the $Le^y$ epitope via an azidonitration/4+2 route.
Figure 7B:
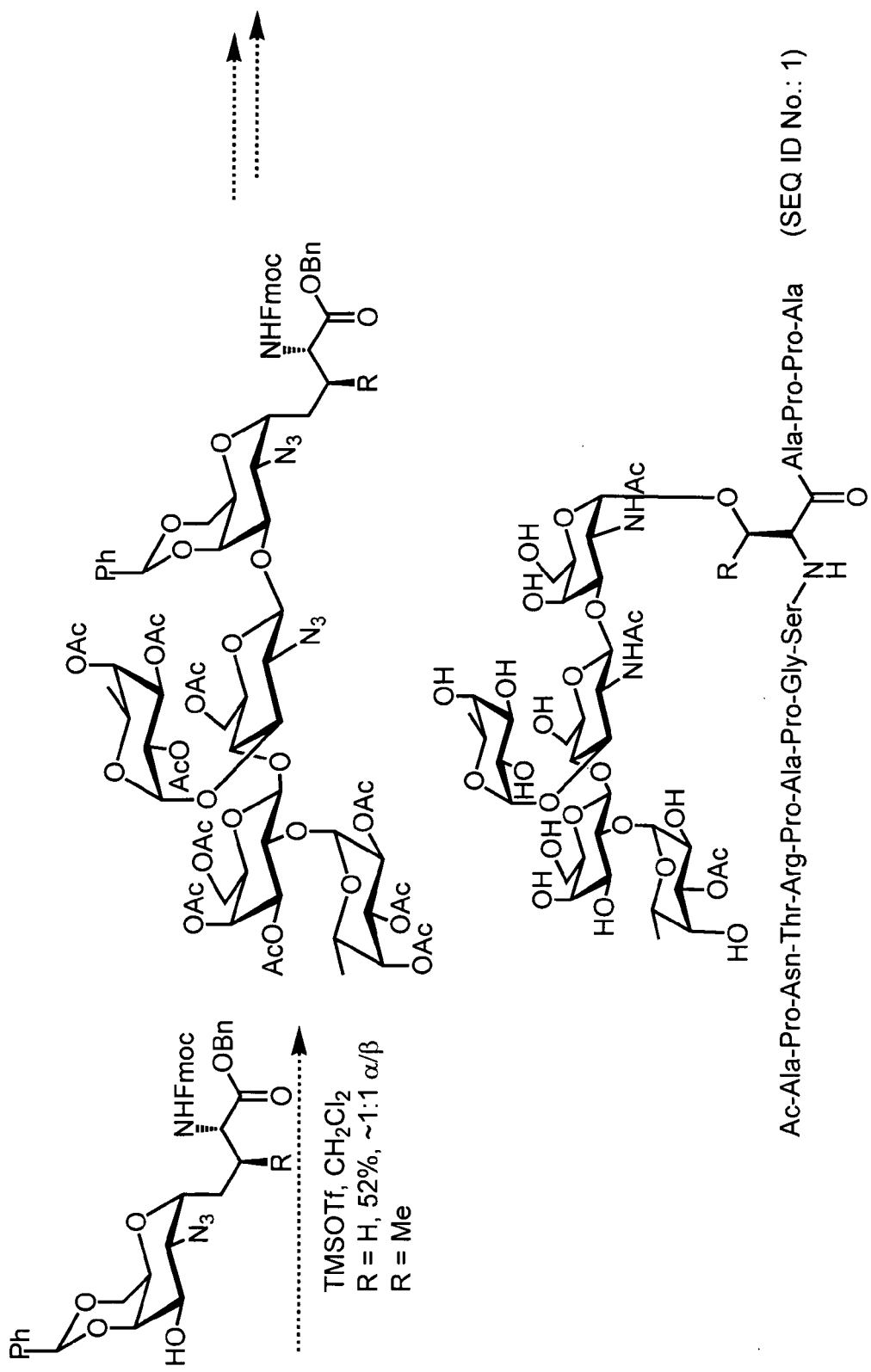
Figure 8A:
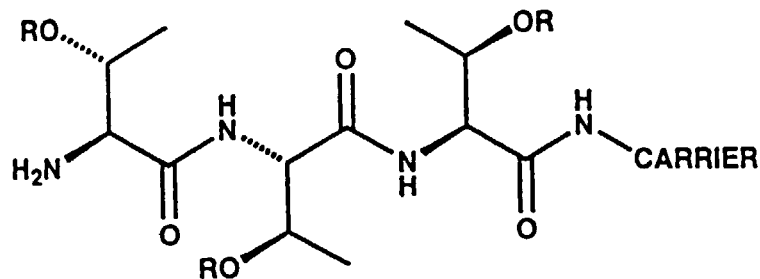
FIGS. 8 and 9 present examples of glycopeptides derived by the method of the invention.
Figure 8B:
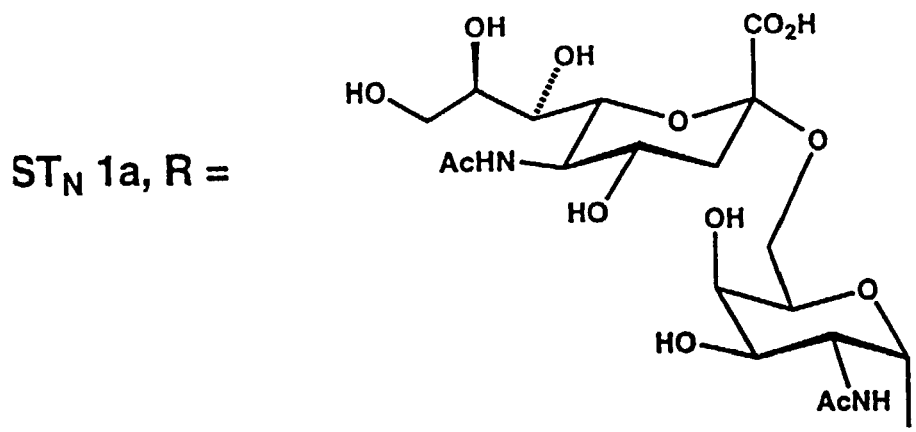
Figure 8C:
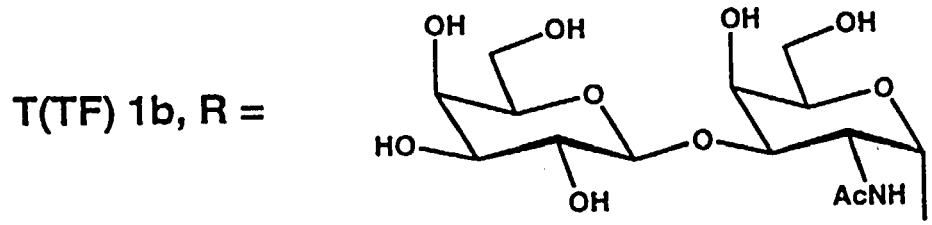
Figure 8D:
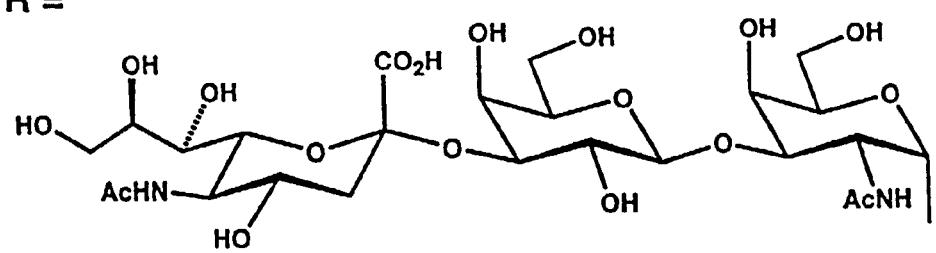
Figure 8E:
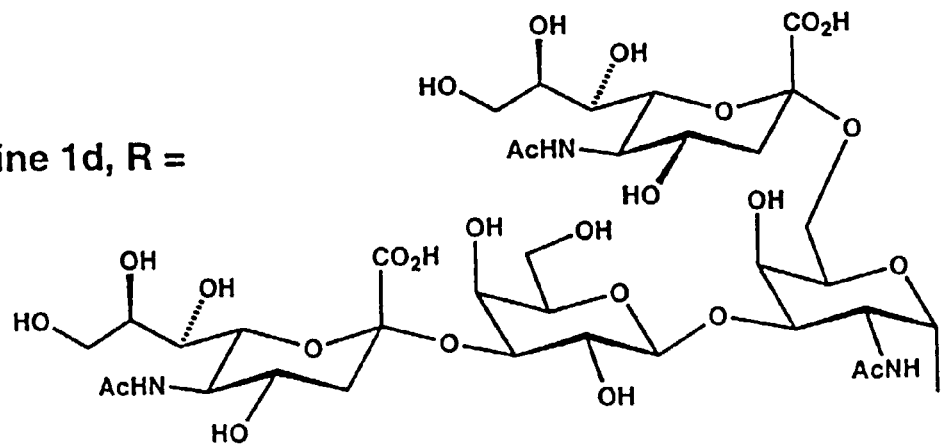
Figure 9A:
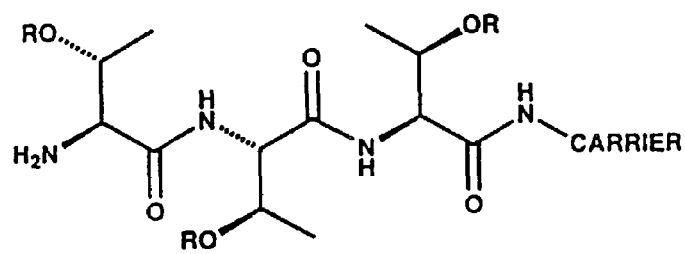
Figure 9B:
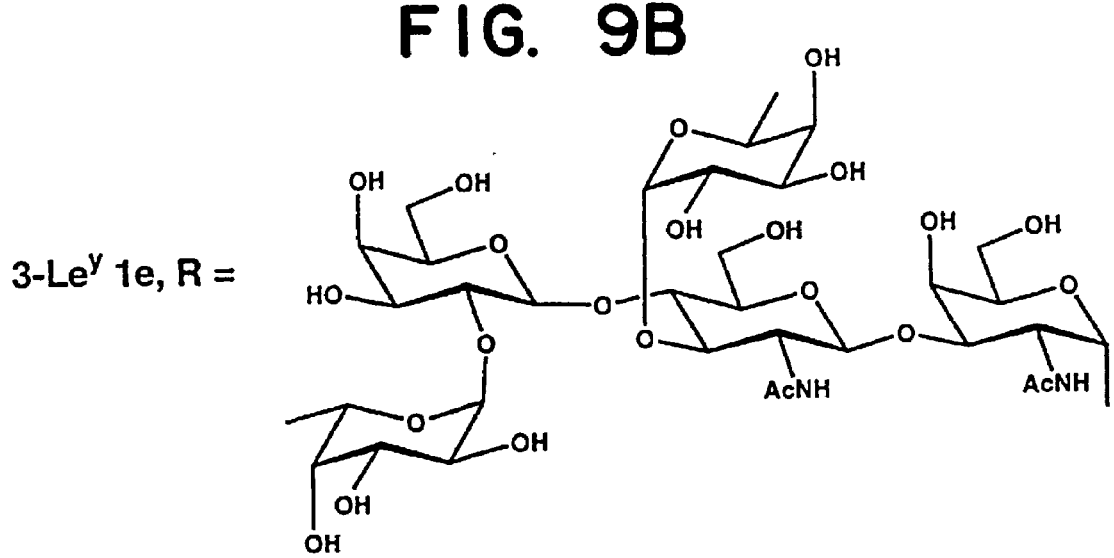
Figure 9C:
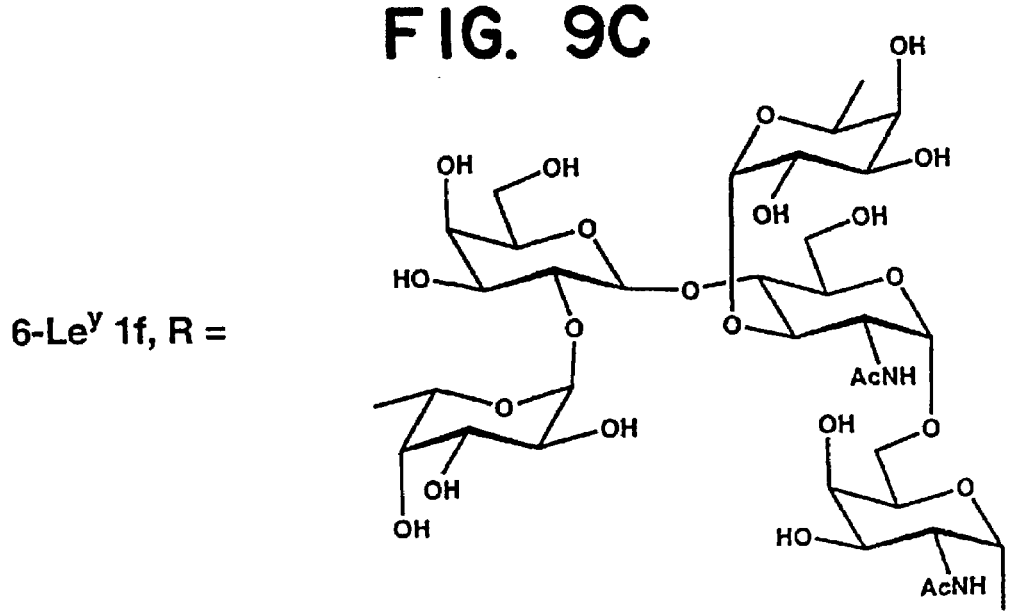
Figure 10A:
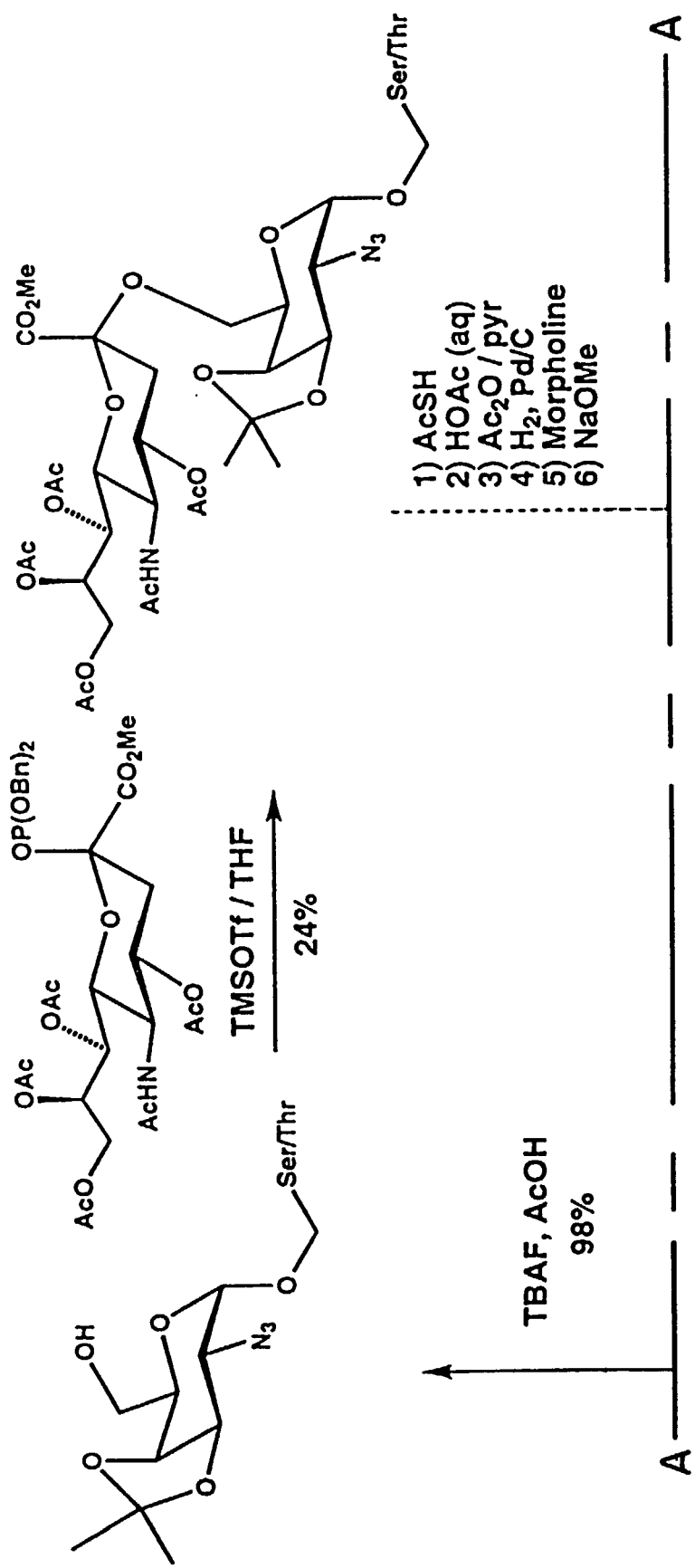
FIG. 10 illustrates a synthetic pathway to prepare glycopeptides $ST_N$ and T(TF).
Figure 10B:
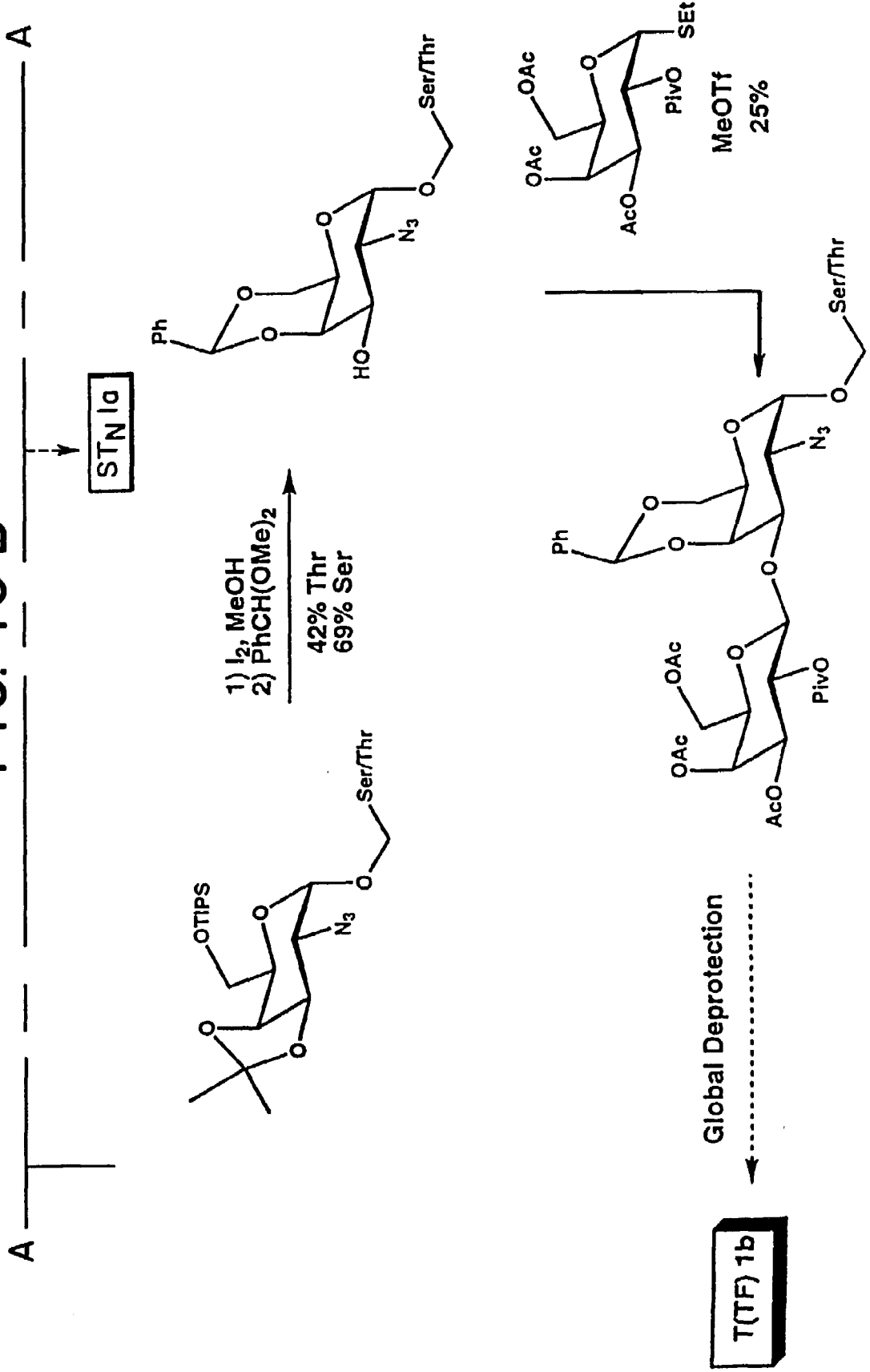
Figure 11A:
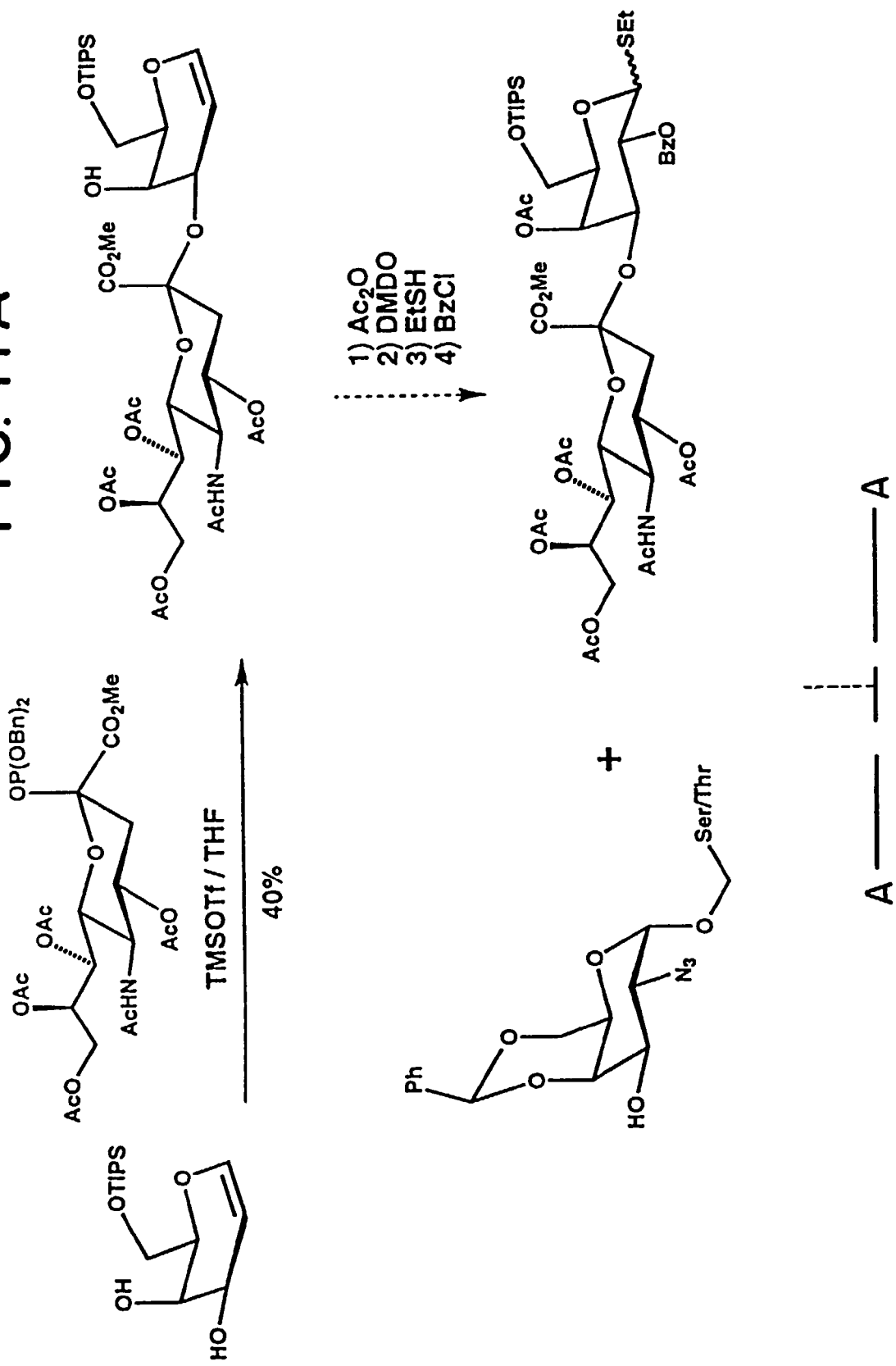
FIG. 11 shows a synthetic pathway to prepare glycopeptide (2,3)ST.
Figure 11B:
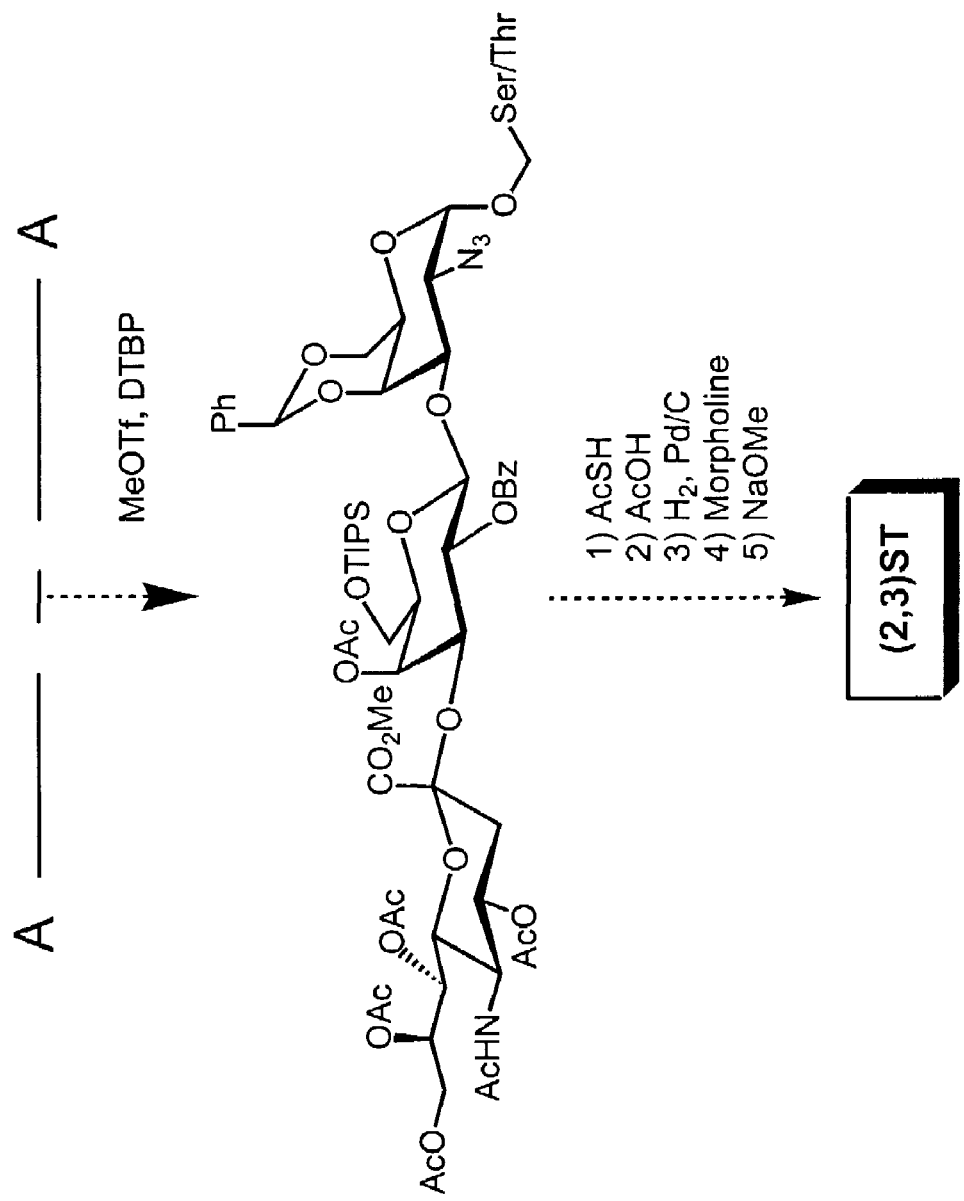
Figure 12A:
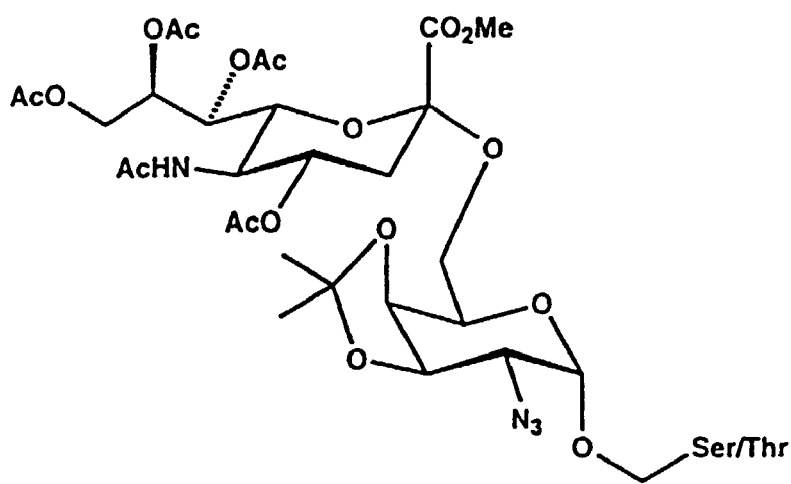
FIG. 12 shows a synthetic pathway to prepare the glycopeptide glycophorine.
Figure 12A:
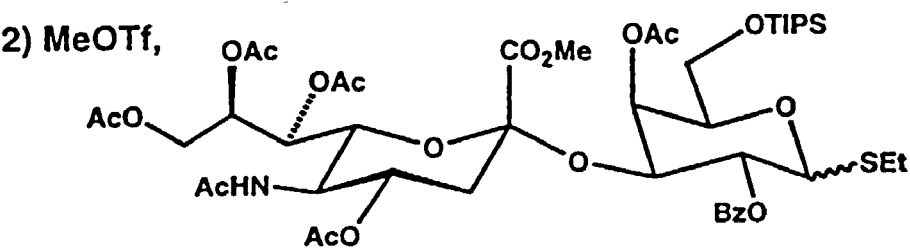
Figure 12:
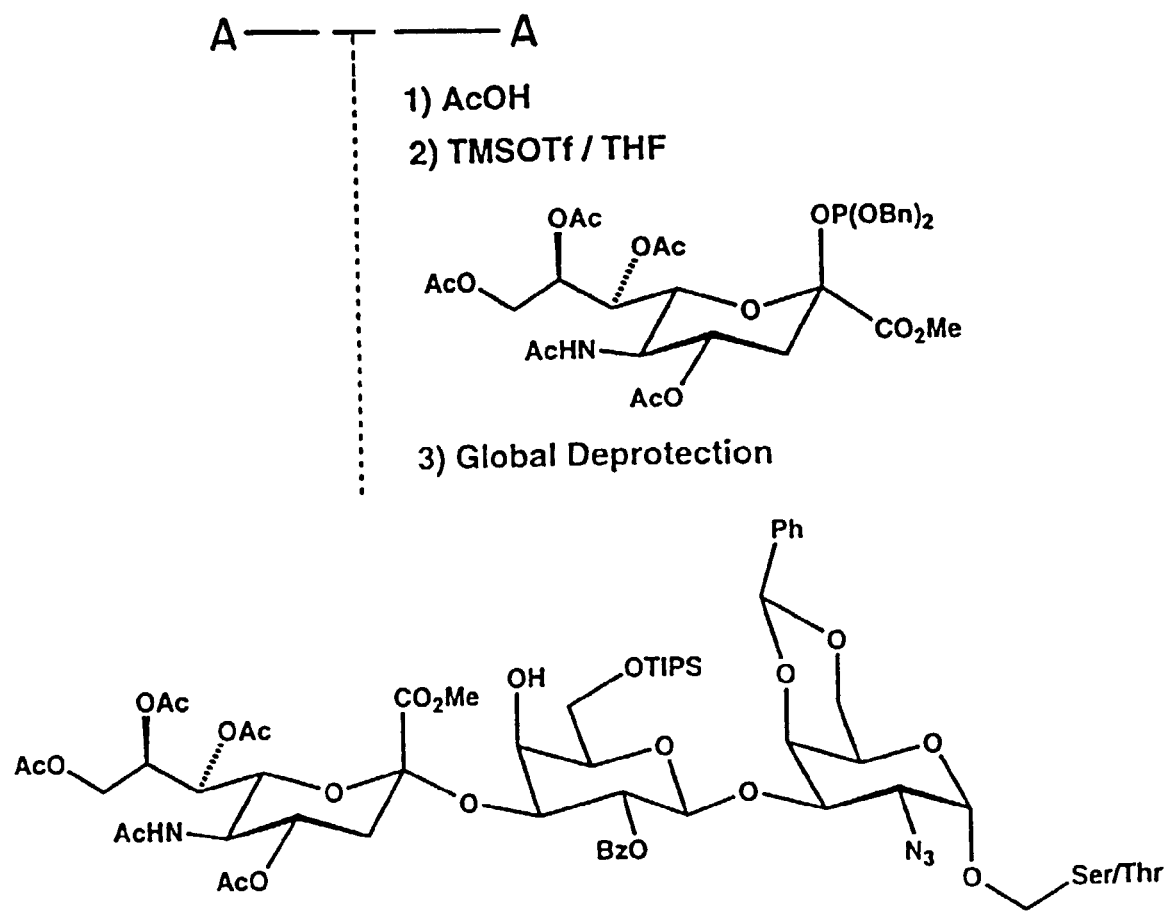
Figure 13A:
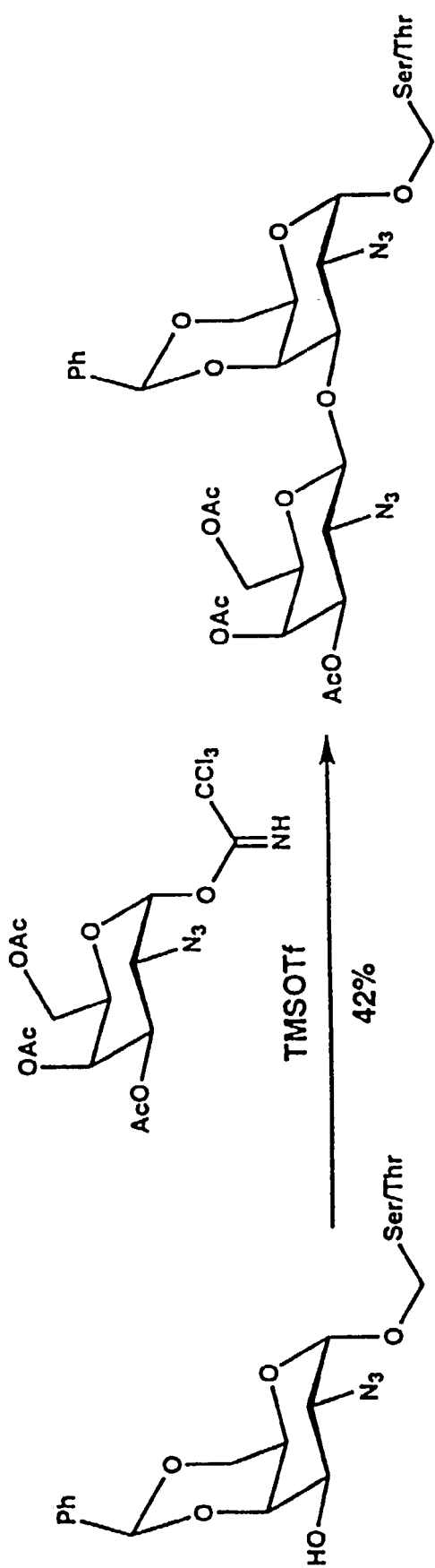
FIG. 13 presents a synthetic pathway to prepare glycopeptides 3-$Le^y$ and 6-$Le^y$.
Figure 13B:
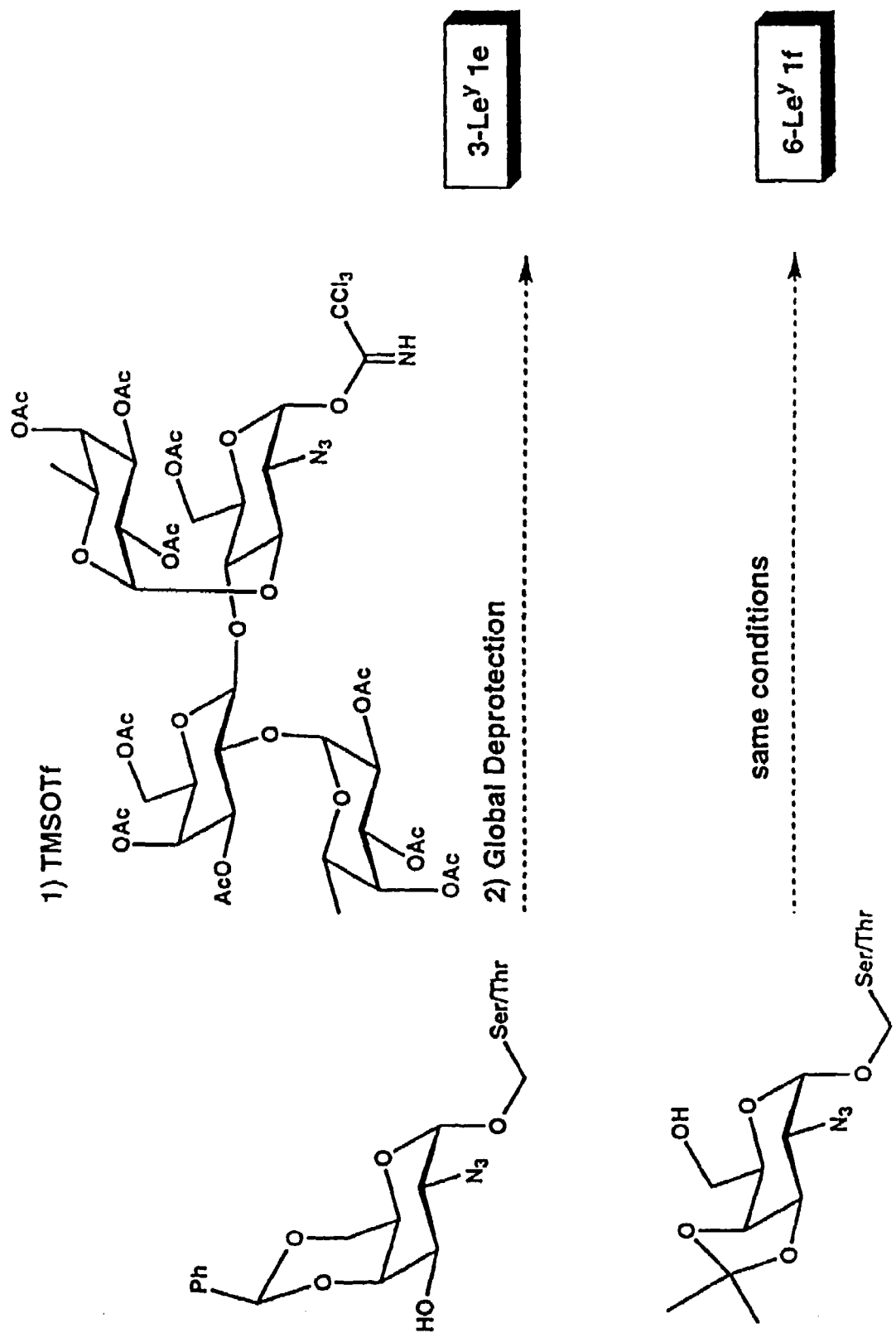
Figure 14A:
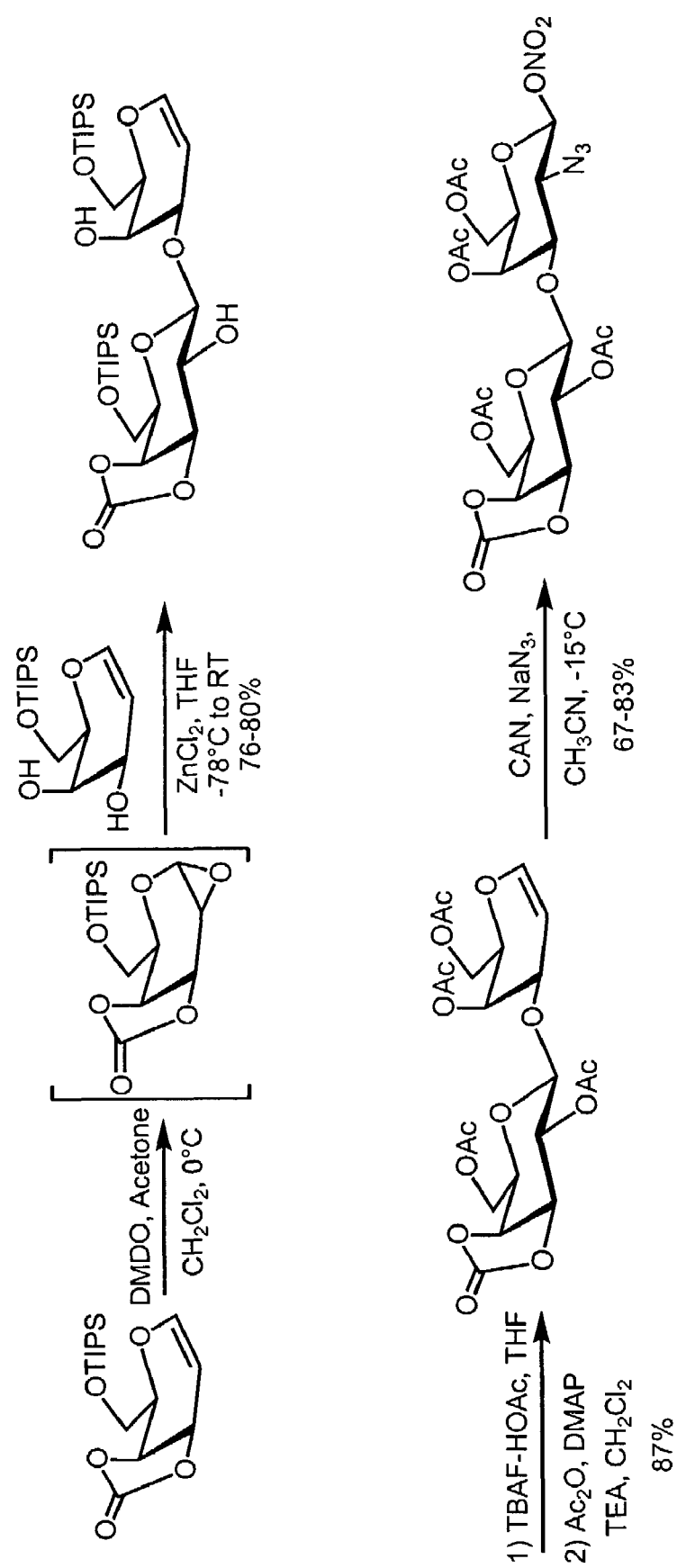
FIG. 14 provides a synthetic pathway to prepare T-antigen.
Figure 14B:
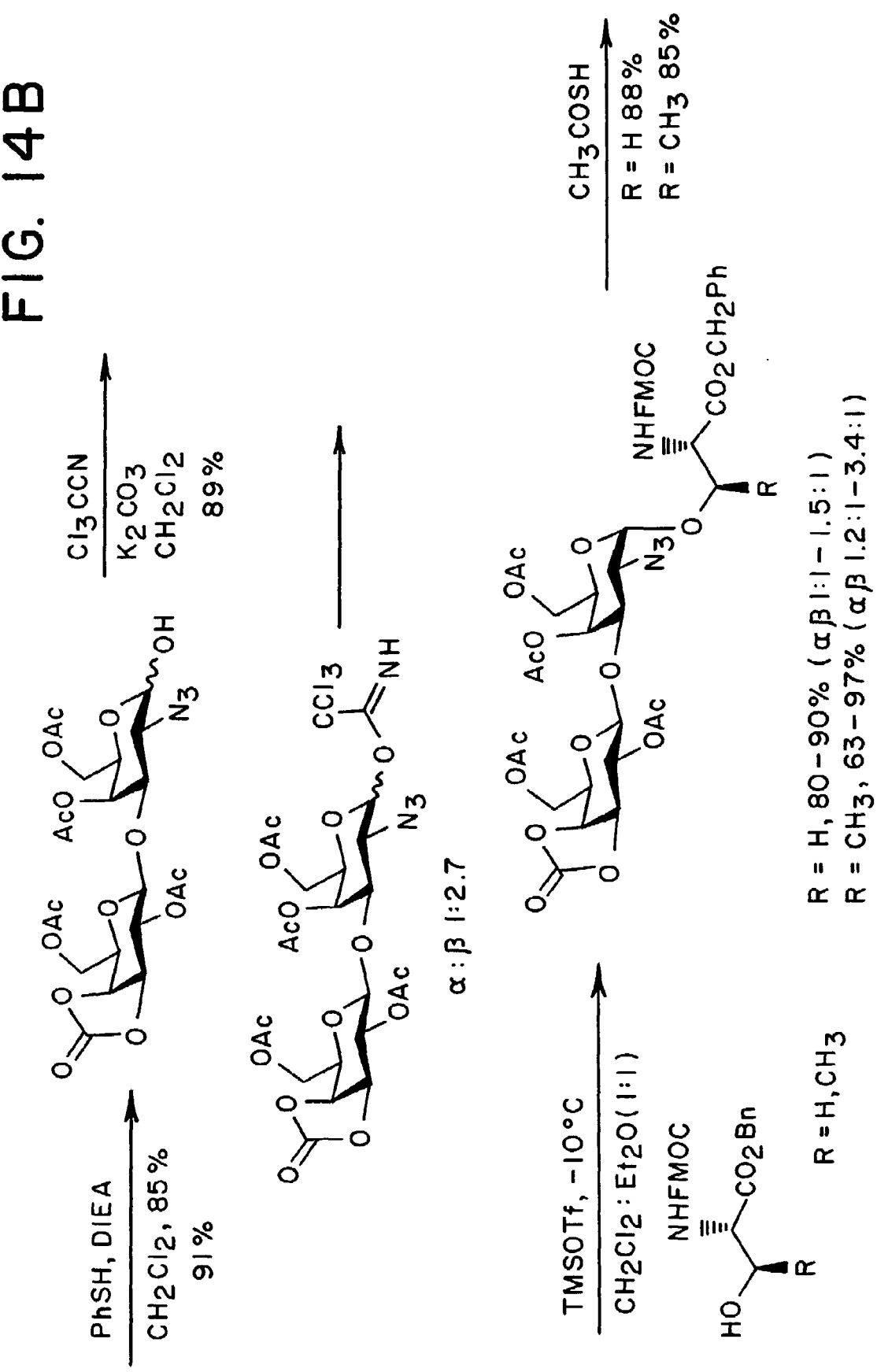
Figure 14C:
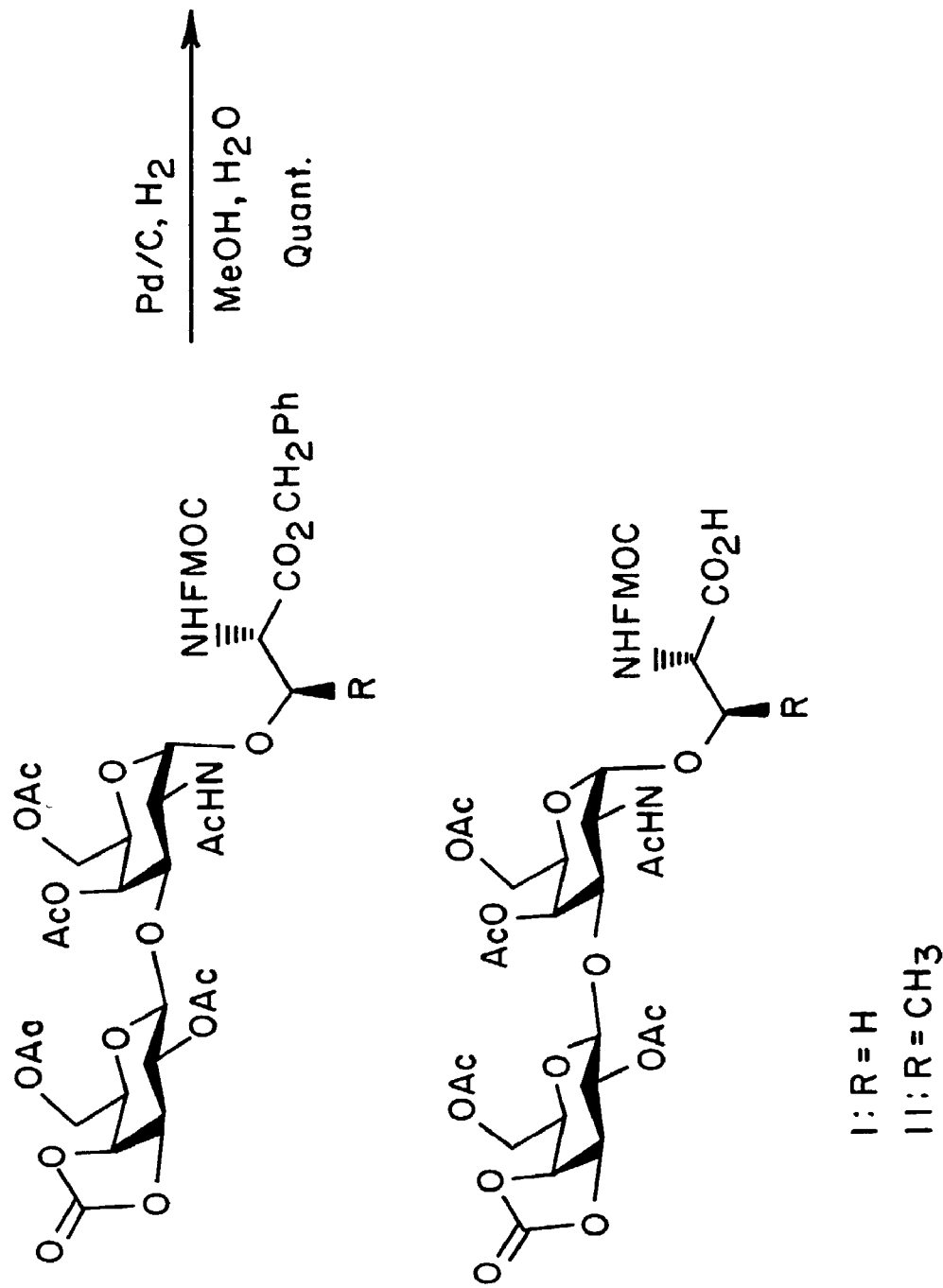
Figure 15A:
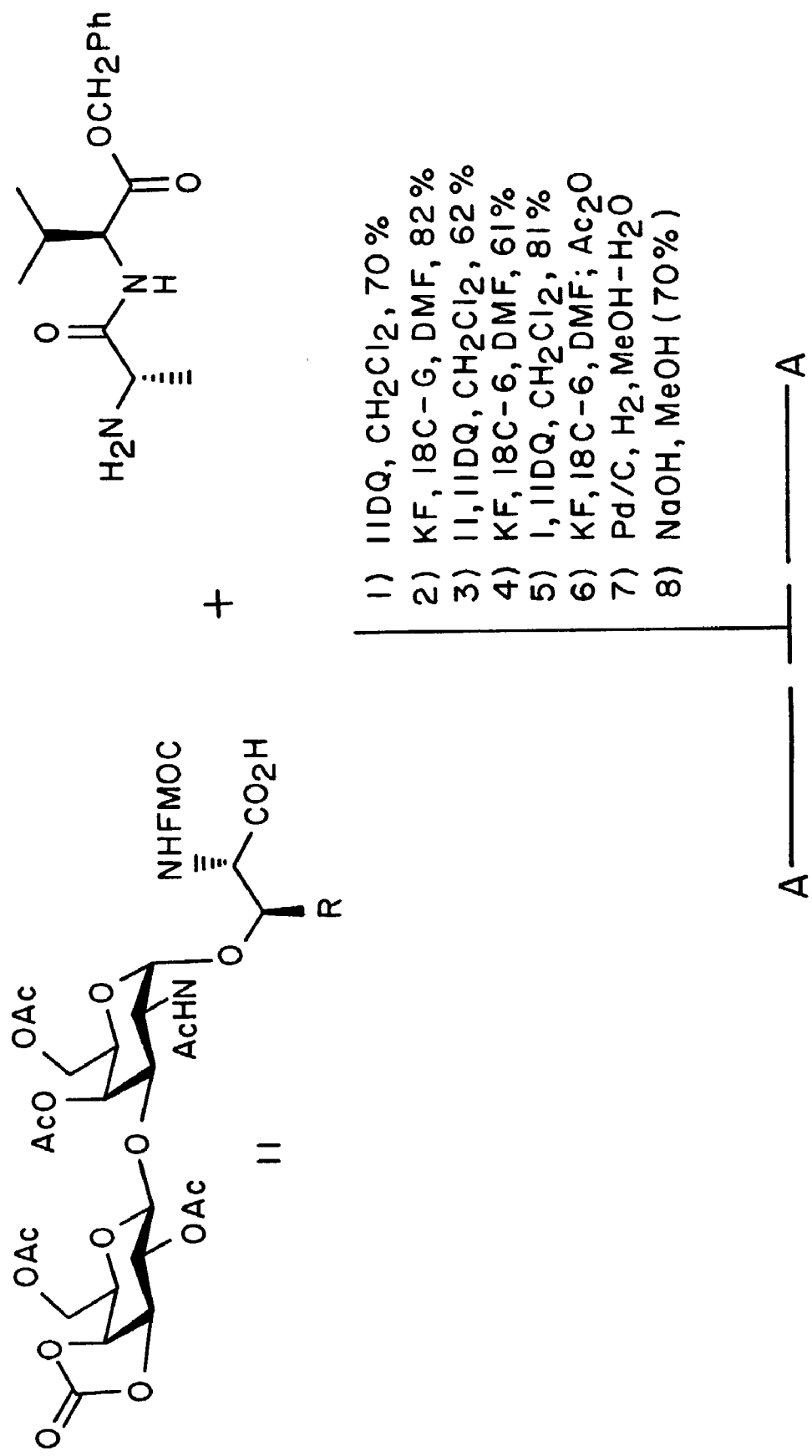
FIG. 15 shows a synthetic pathway to prepare the alpha cluster of the T-antigen.
Figure 15B:
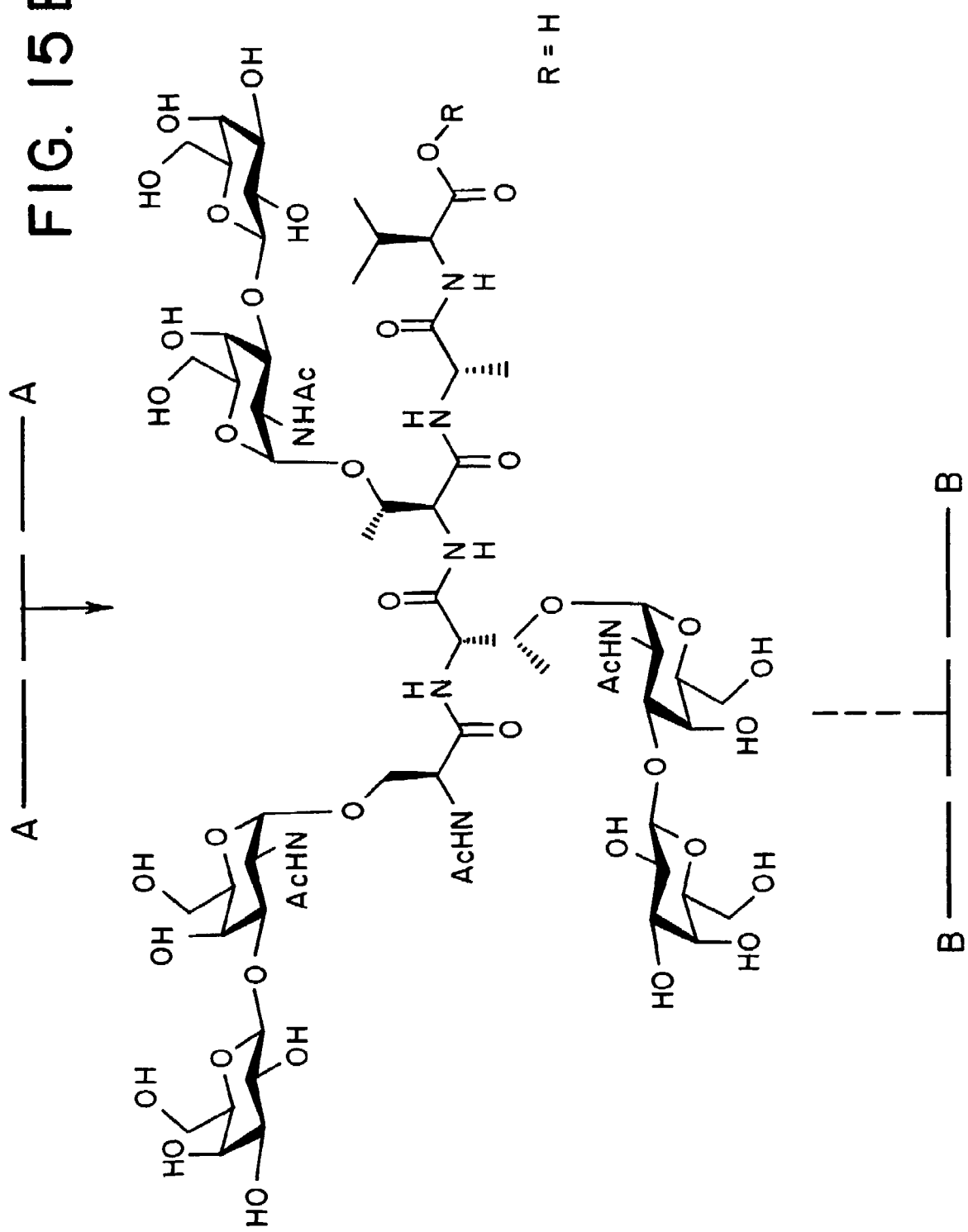
Figure 16:
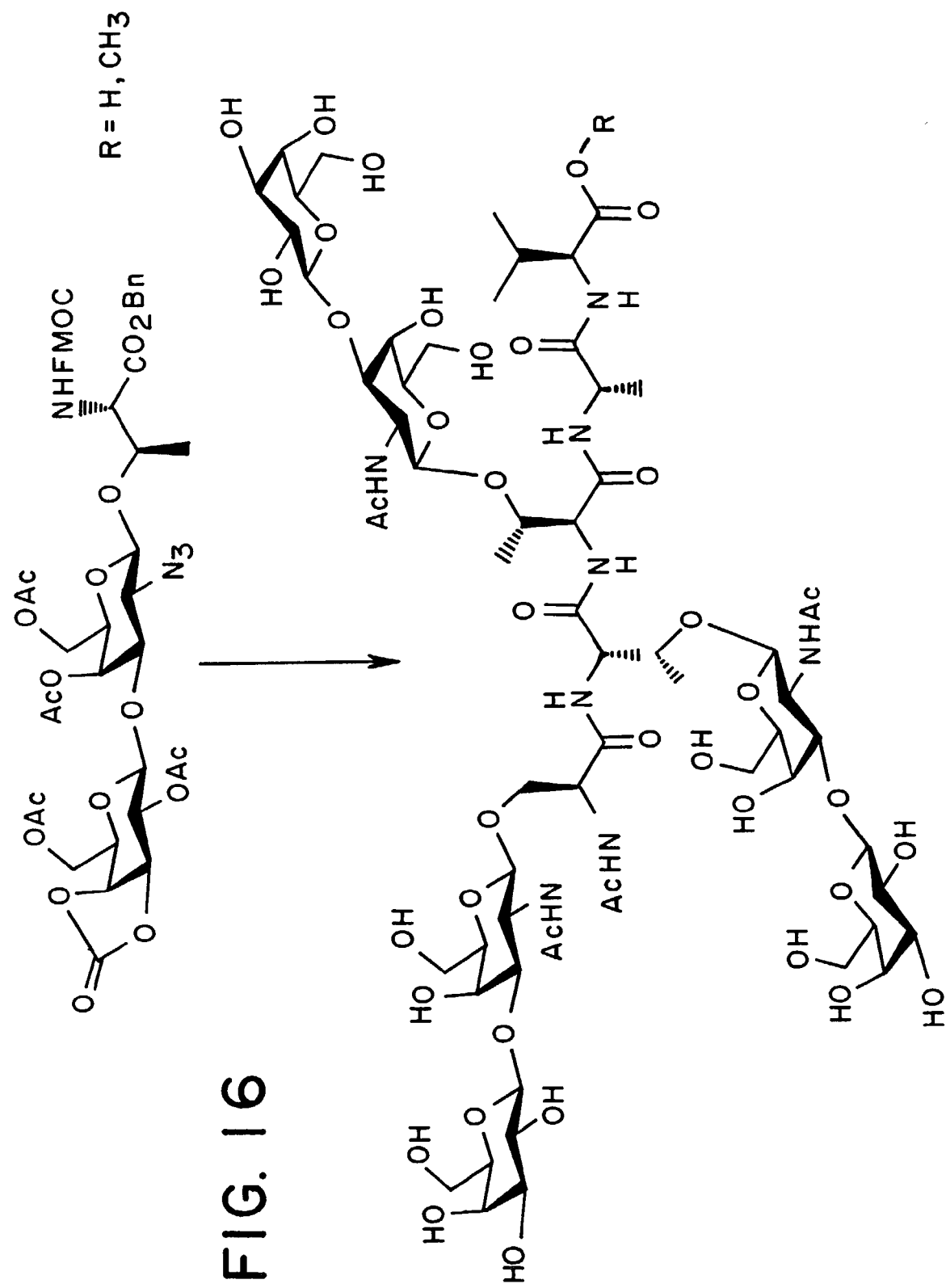
FIG. 16 shows a synthetic pathway to prepare the beta cluster of the T-antigen. The sequence of reactions are as represented in FIG. 15.
Figure 17A:
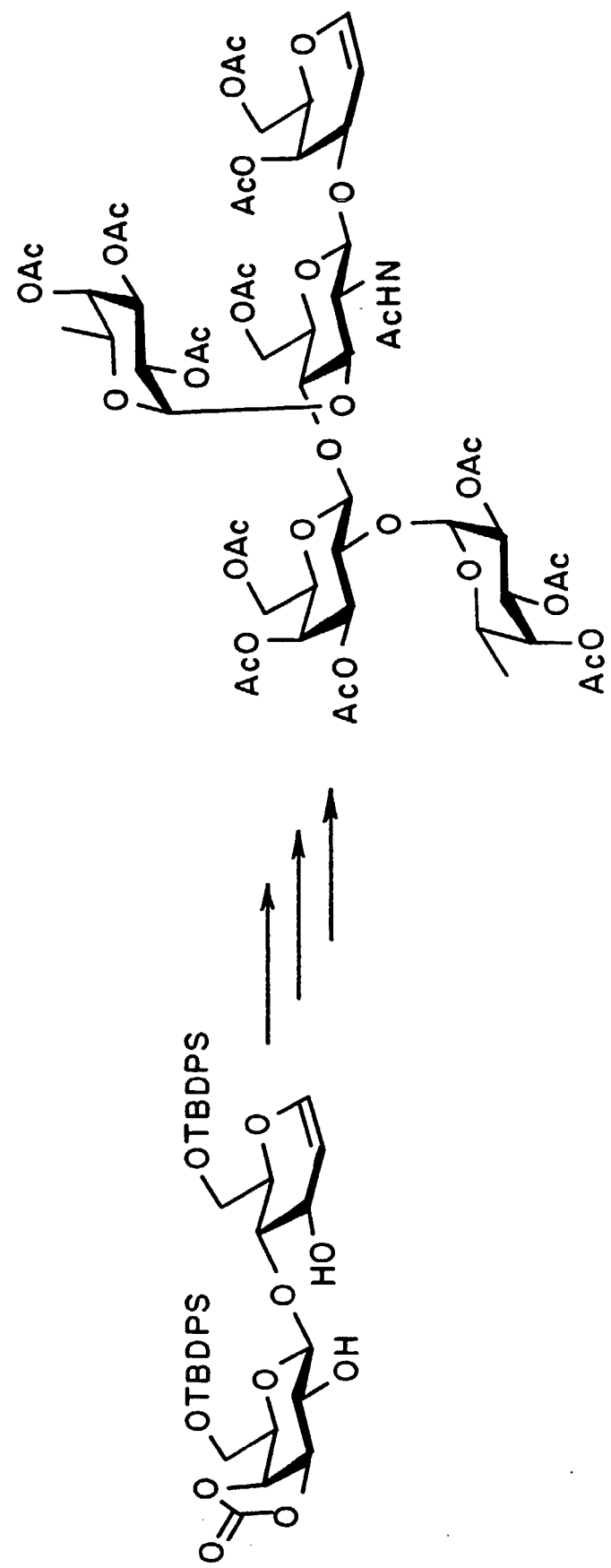
FIGS. 17, 18 and 19 presents a synthesis of α-O-linked glycopeptide conjugates of the $Le^y$ epitope. R is defined in FIG. 18.
Figure 17B:
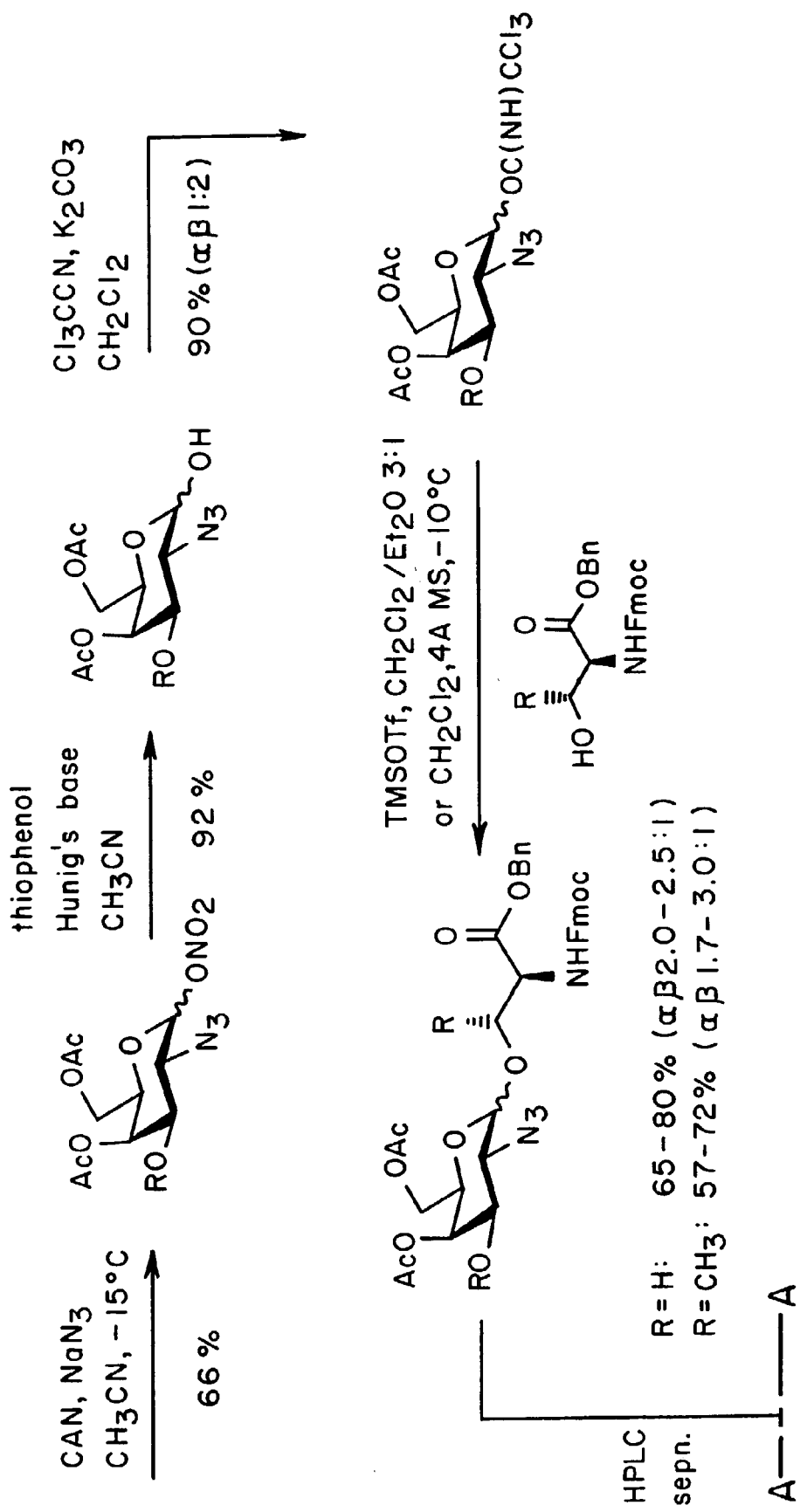
Figure 17C:
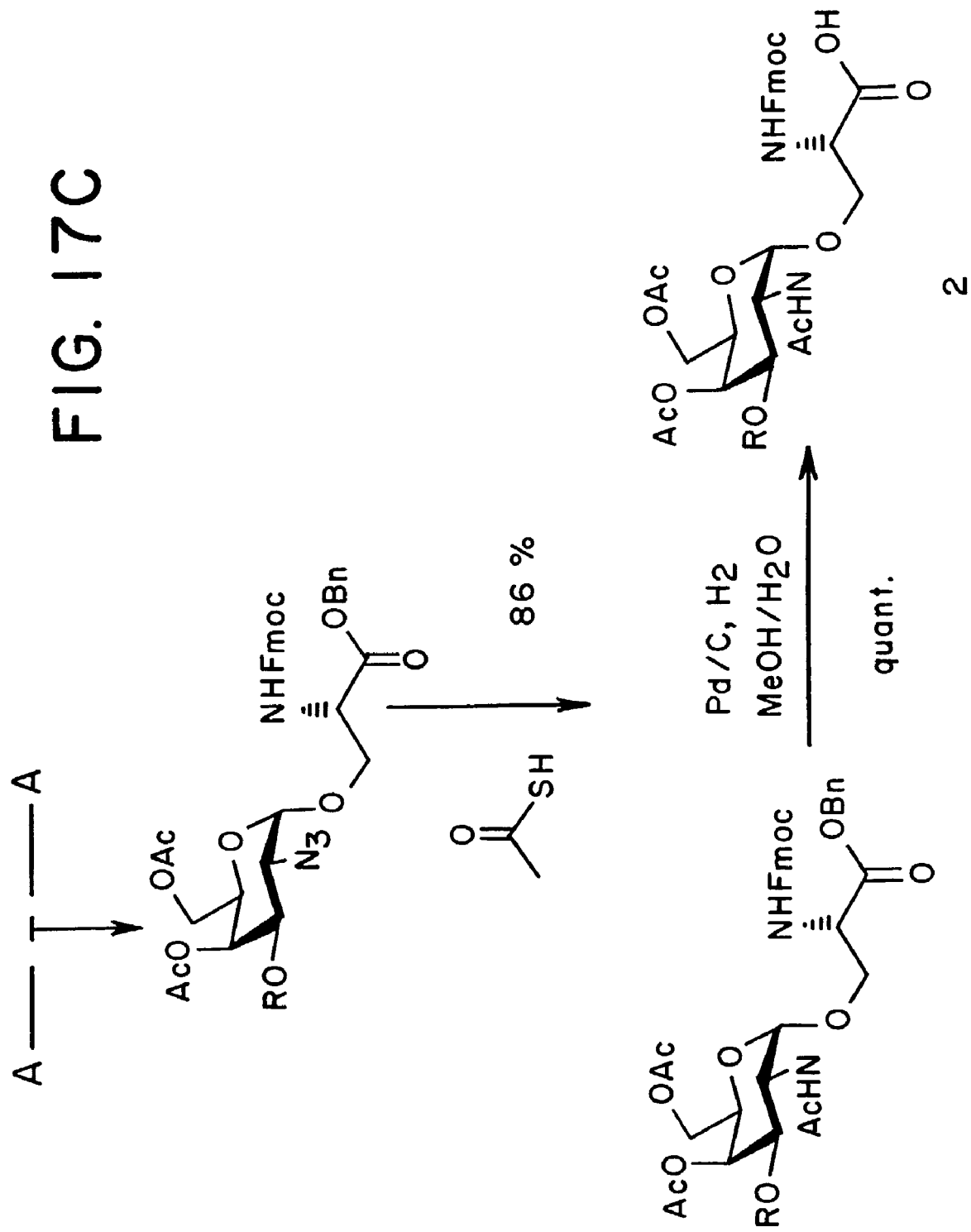
Figure 18A:
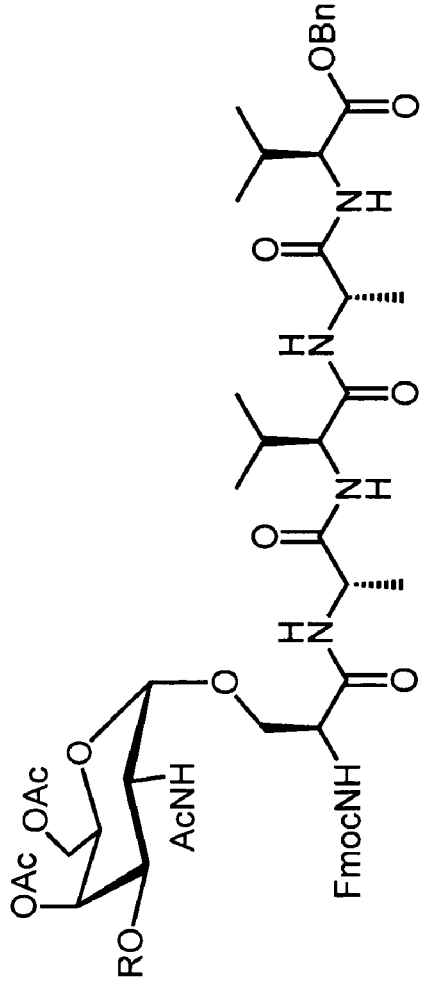
Figure 18B:
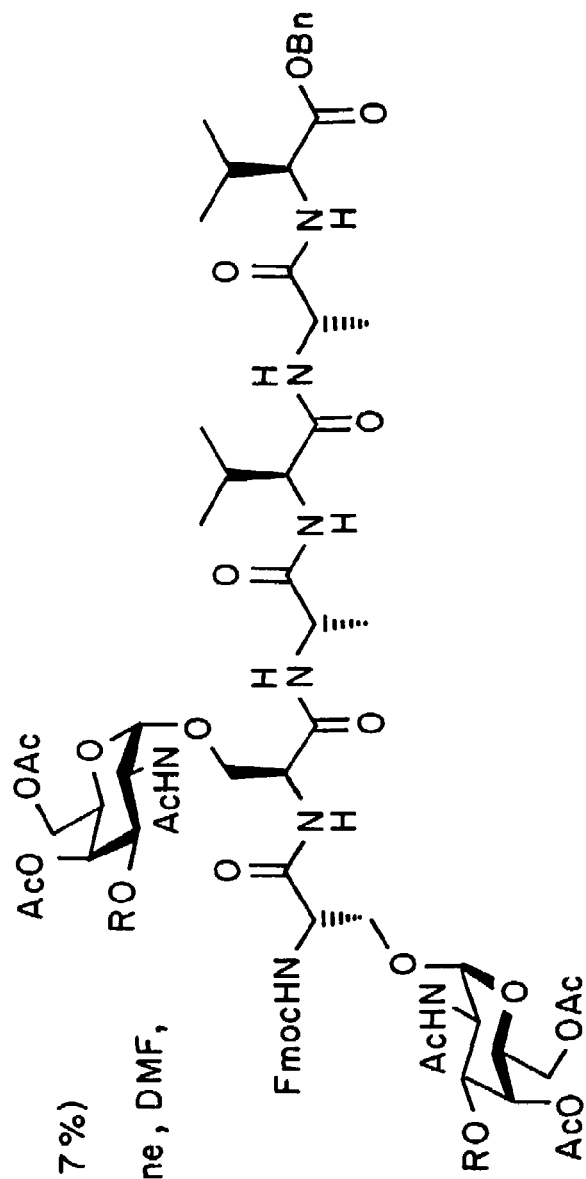
Figure 18C:
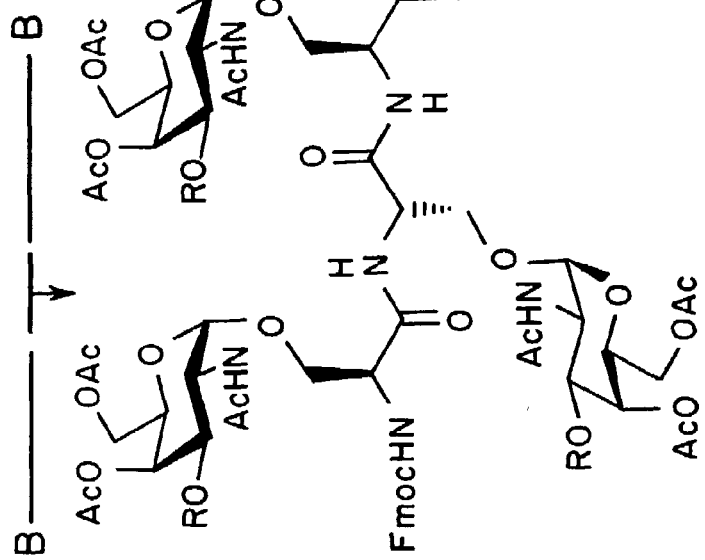
Figure 18C:
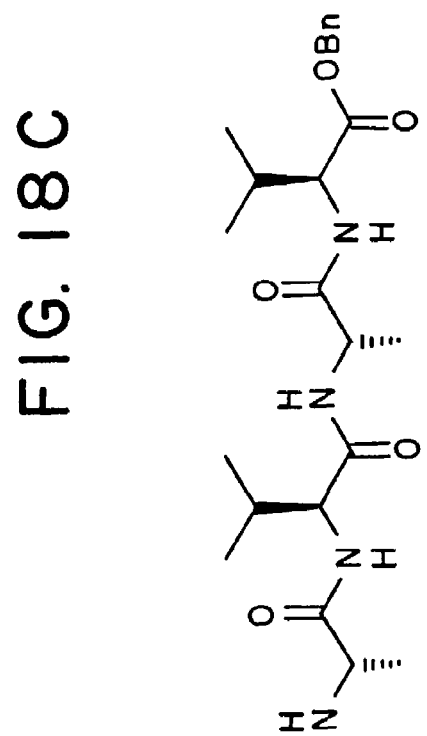
Figure 18C:
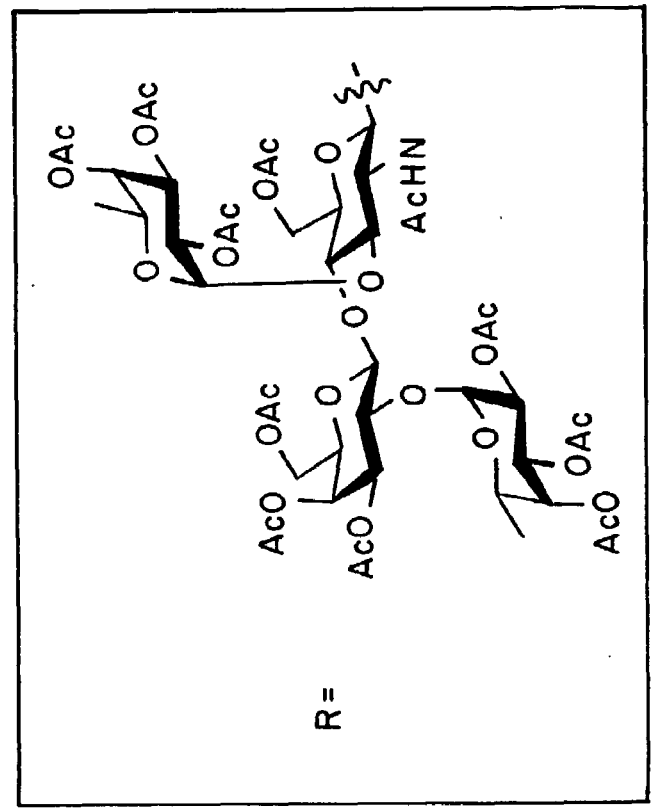
Figure 19A:
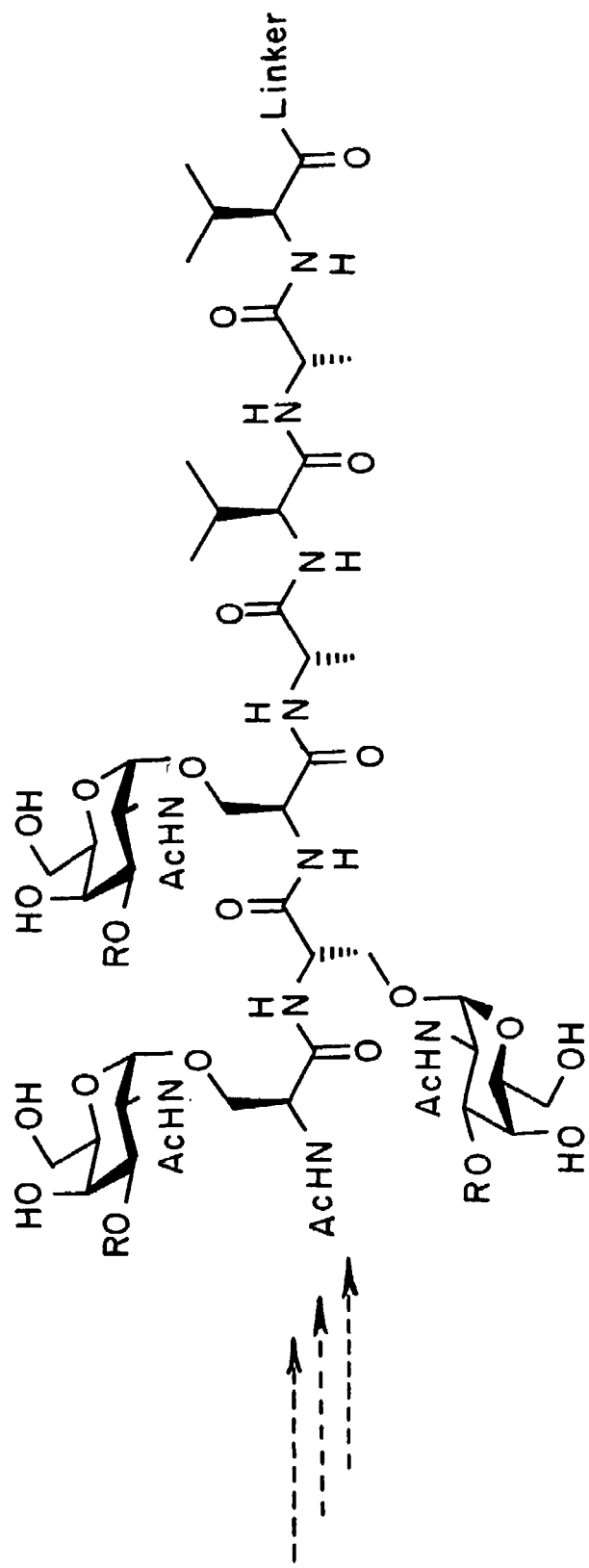
Figure 19B:
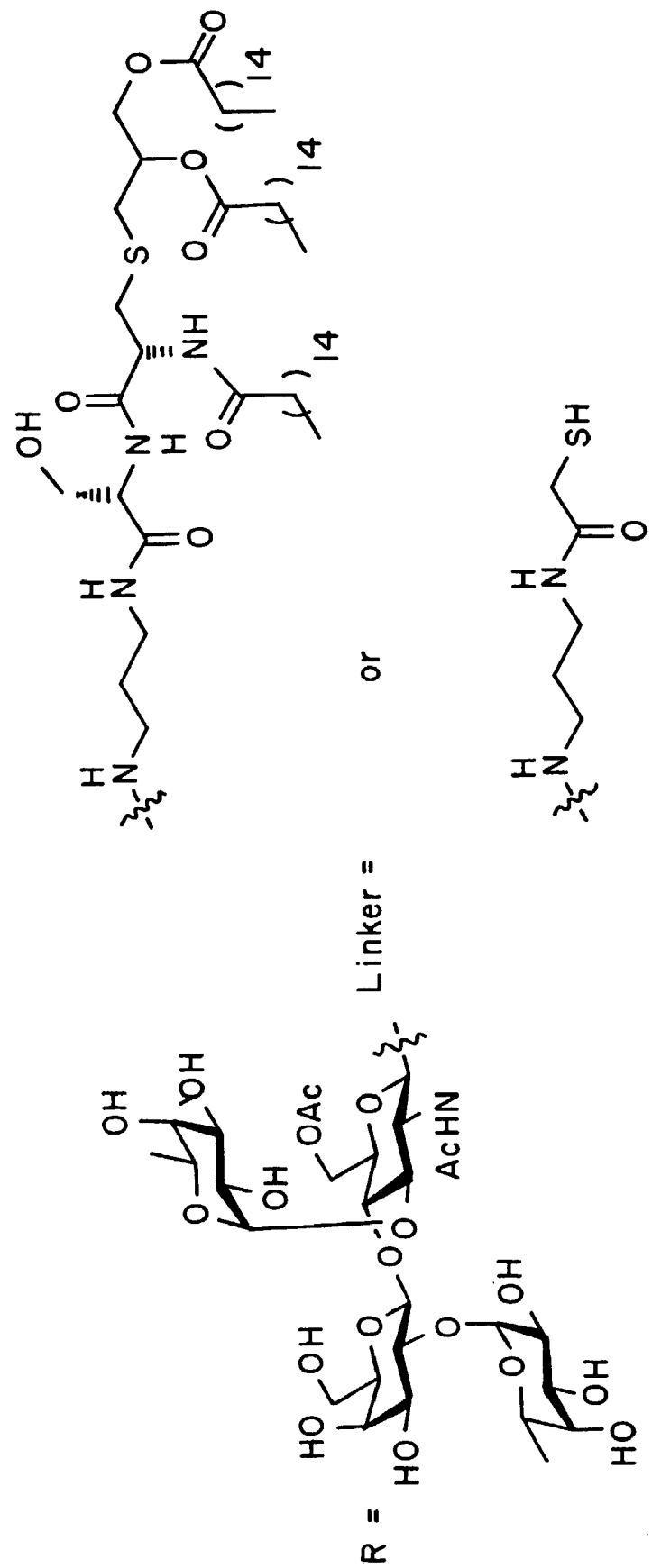
Figure 20A:
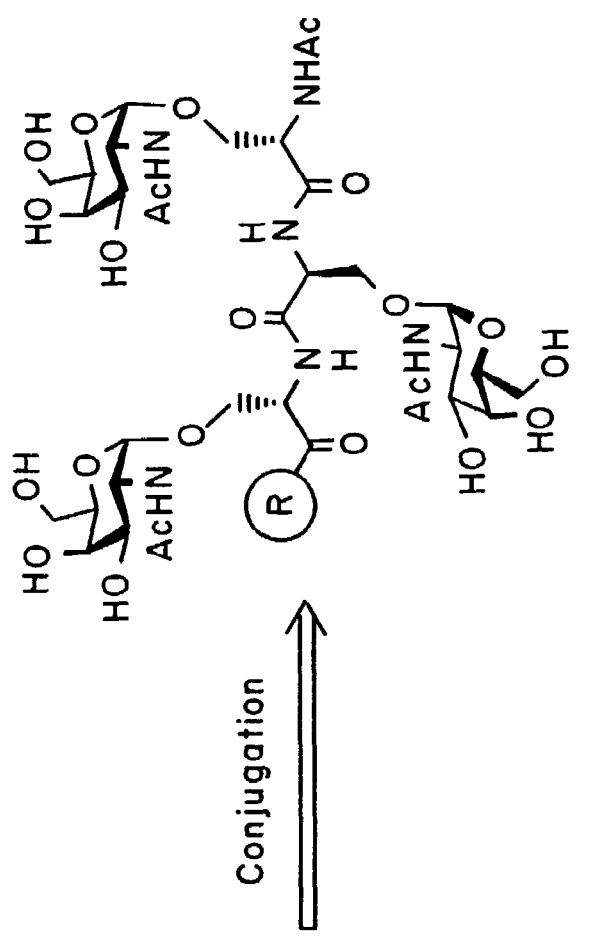
FIG. 20 shows (A) the conjugation of Tn-trimer glycopeptide to PamCys lipopeptide; (B) a general representation of a novel vaccine construct; and (C) a PamCys Tn Trimer.
Figure 20A:
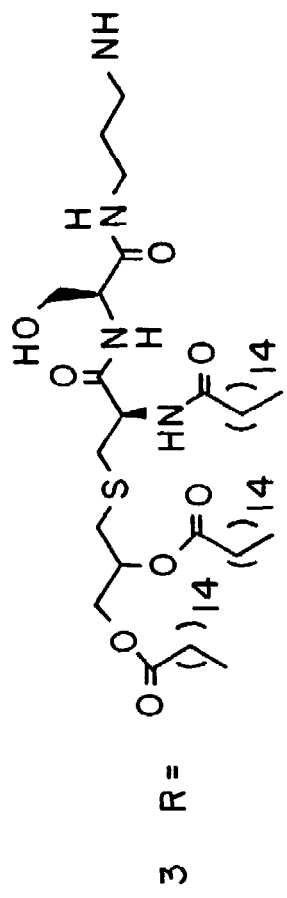
Figure 20A:
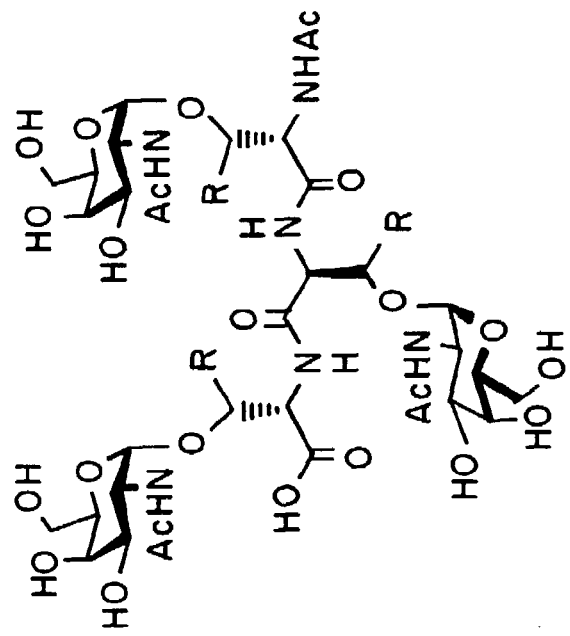
Figure 20B:
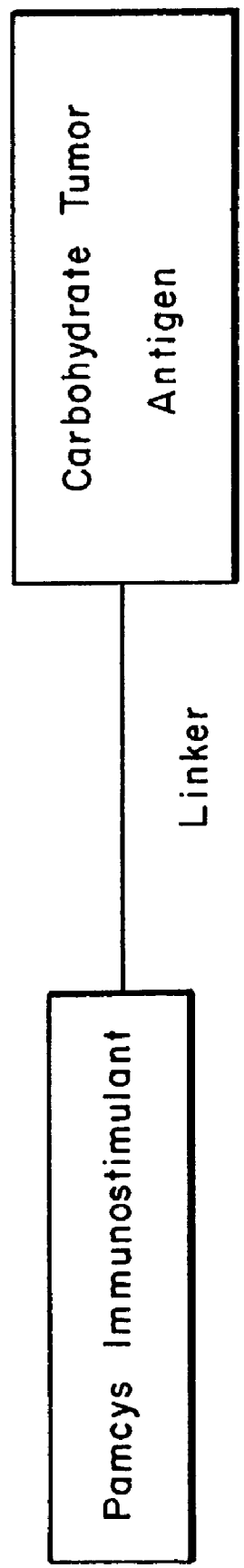
Figure 20C:
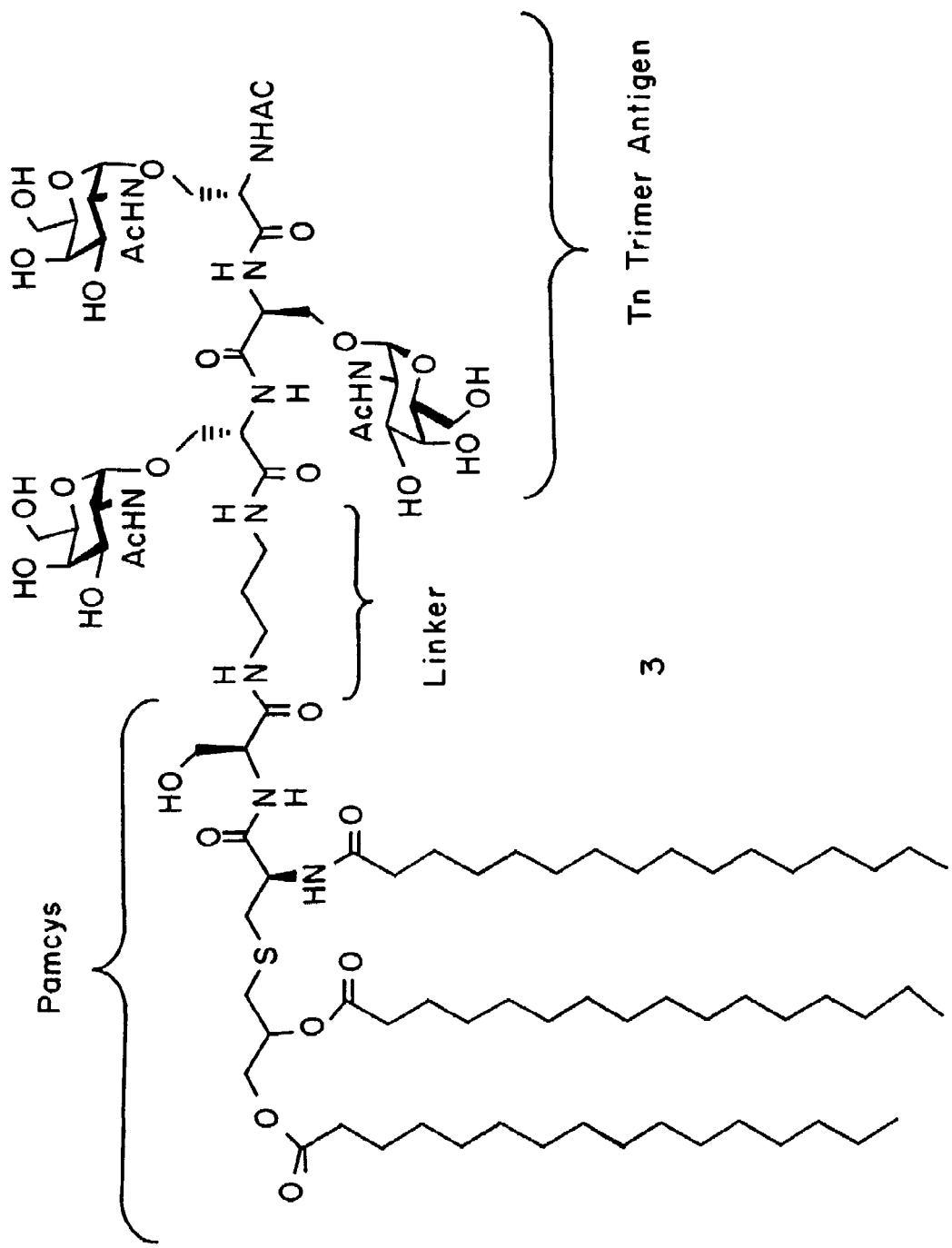
Figure 21A:
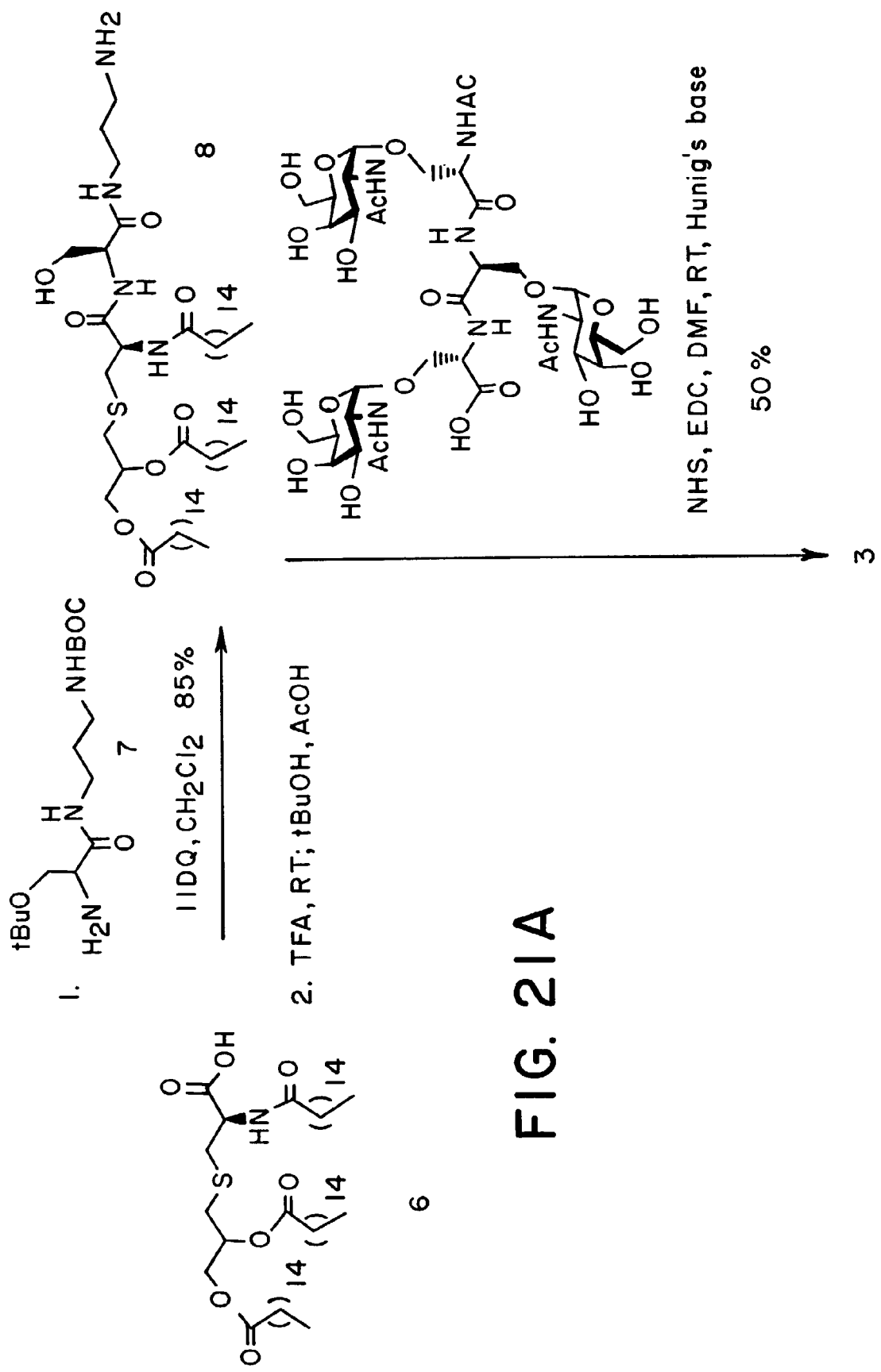
FIG. 21 illustrates (A) a method of synthesis of a Pam-Cys-Tn-trimer 3; and (B) a method of preparation of KLH and BSA conjugates (12, 13) via cross-linker conjugation.
Figure 21B:
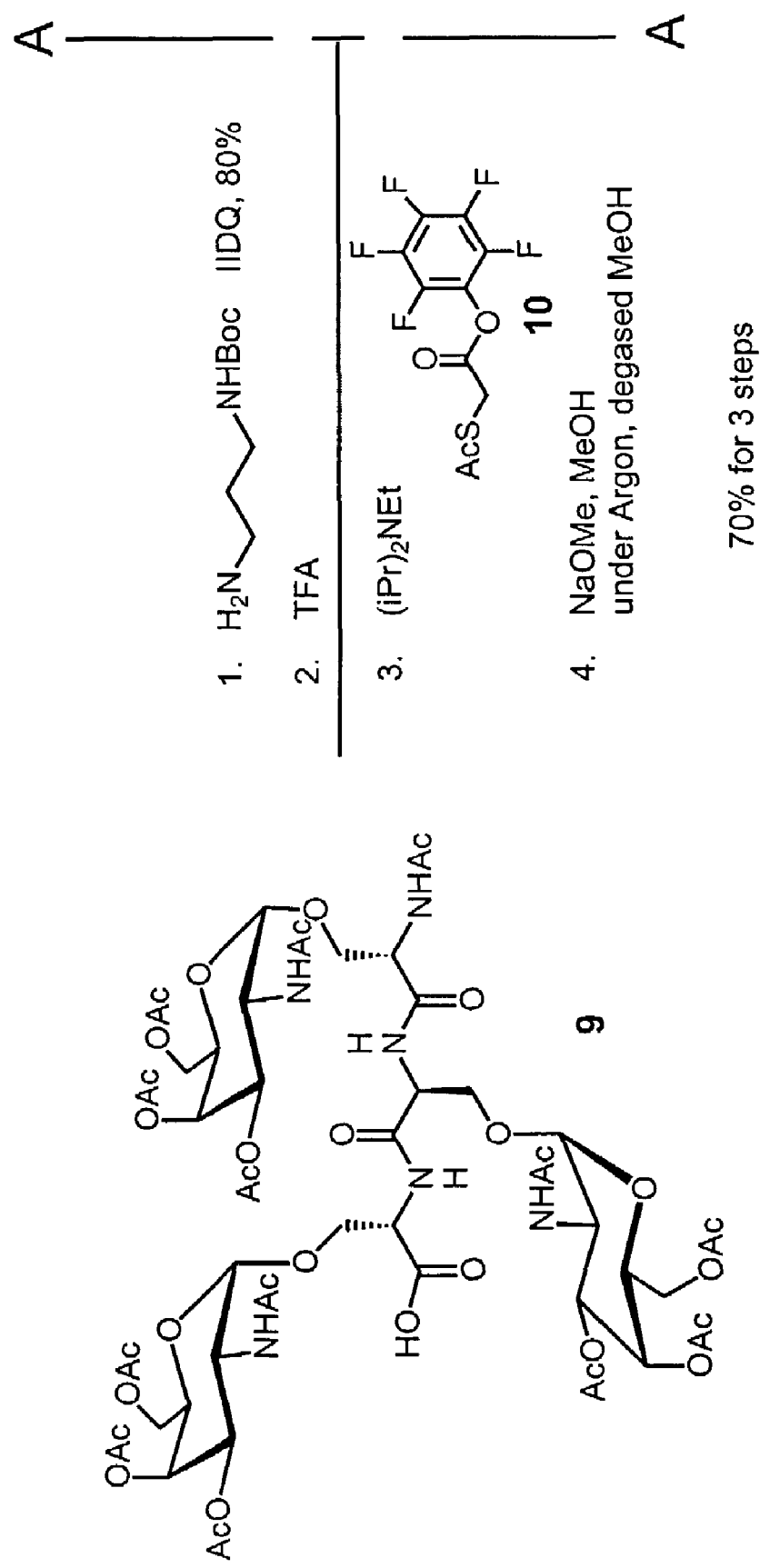
Figure 21C:
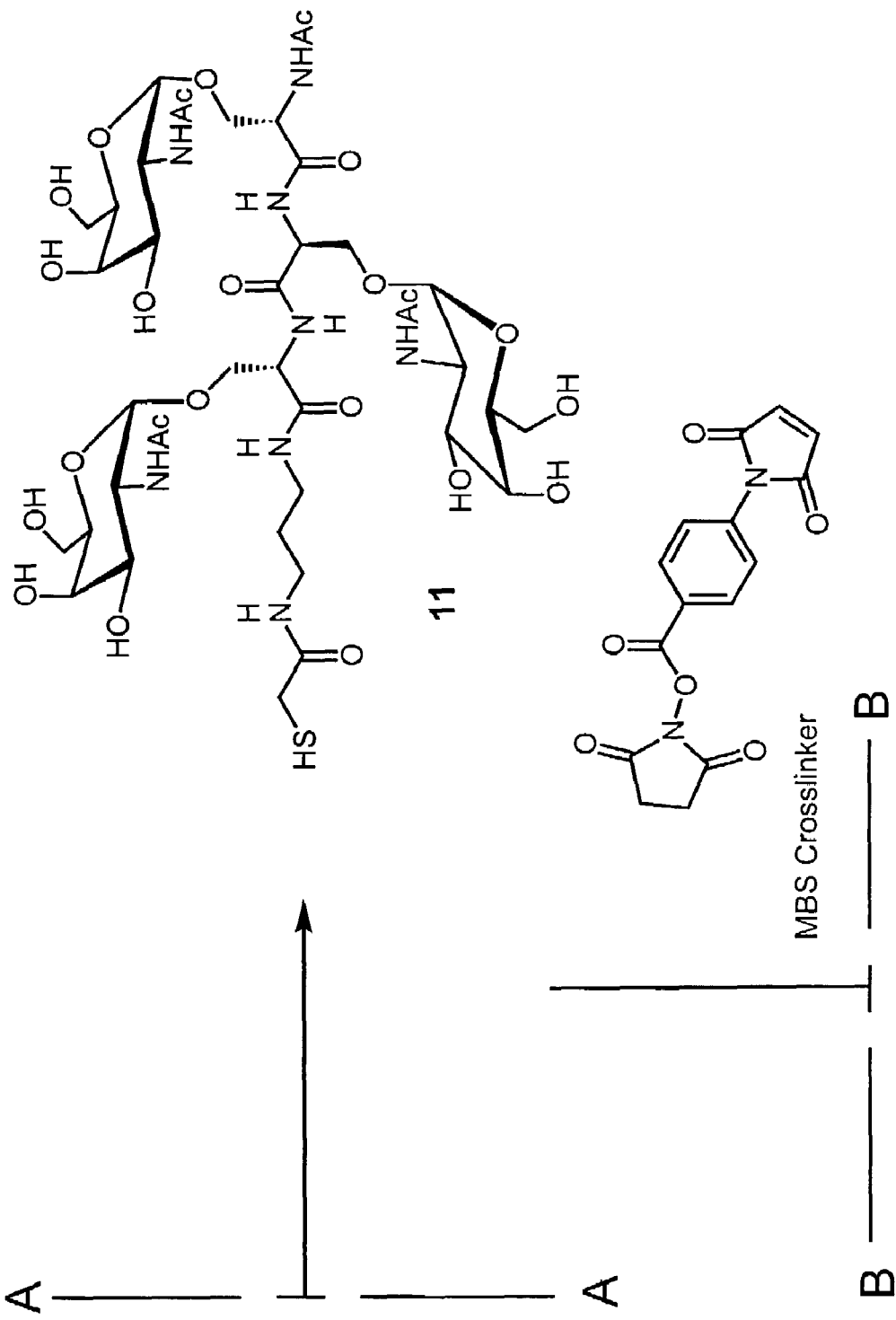
Figure 21D:
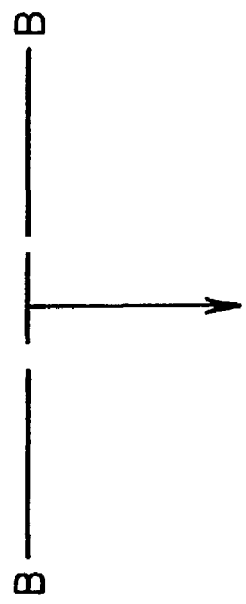
Figure 21D:
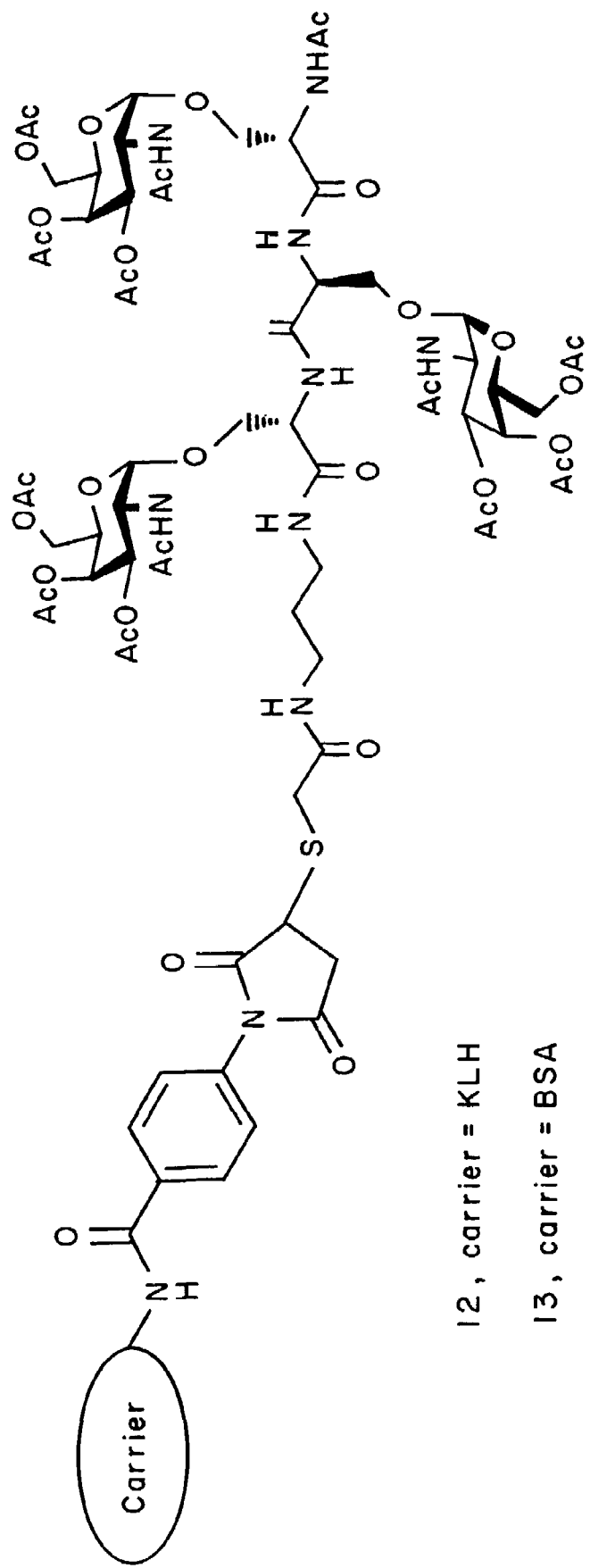

The orthogonal exposure of both N- and C-termini provided an opportunity for further extension of the glycopeptide constructs via fragment joining. In order to demonstrate the viability of such claims, a nonapeptide with ST triad 19 was made by means of coupling tripeptide 18 to hexapeptide 17 (see FIG. 5). The previous deprotection protocol provided nonapeptide mucin model 20, wherein the o-glycosylated serine-threonine triad had been incorporated in the middle of the peptide.

Vaccination with Tn Cluster Constructs in Mice

The present invention provides anti-tumor vaccines wherein the glycopeptide antigen disclosed herein is attached to the lipopeptide carrier PamCys. The conjugation of the antigen to the new carrier represents a major simplification in comparison to traditional protein carriers. Tables 2 and 3 compare the immunogenicity of the new constructs with the protein carrier vaccines in mice. These novel constructs proved immunogenic in mice. As shown in the Tables, the Tn-PamCys constructs elicit high titers of both IgM and IgG after the third vaccination of mice. Even higher titers are induced after the fifth vaccination. The Tn-KLH vaccine yields stronger overall response. However, the relative ratio of IgM/IgG differs between the two vaccines. Tn-KLH gives higher IgM/IgG ratio than the Tn Pamcys. In a relative sense, the novel Tn-PamCys vaccine elicits a stronger IgG response. In contrast to protein carrier vaccines, the adjuvant QS-21 does not provide any additional enhancement of immunogenicity. Accordingly, the PamCys lipopeptide carrier may be considered as a "built-in" immunostimulant/adjuvant. Furthermore, it should be noted that QS-21 enhances the IgM response to Tn-PamCys at the expense of IgG titers. A vaccine based on PamCys carriers is targeted against prostate tumors.

TABLE 2

Antibody Titers by Elisa against Tn-Cluster: 10 μg Tn cluster-Pam

| | Pre-serum | | 10 days post 3rd | |
|---|---|---|---|---|
| Group | IgM | IgG | IgM | IgG |
| 1.1 | 50 | 0 | 450 | 450 |
| 1.2 | 50 | 0 | 1350 | 50 |
| 1.3 | 50 | 0 | 4050 | 150 |
| 1.4 | 0 | 0 | 4050 | 150 |
| 1.5 | 0 | 0 | 450 | 1350 |
| 10 μg Tn cluster-pam + QS-21 | | | | |
| 2.1 | 50 | 0 | 1250 | 50 |
| 2.2 | 0 | 0 | 1350 | 0 |
| 2.3 | 0 | 0 | 1350 | 50 |
| 2.4 | 0 | 0 | 1350 | 150 |
| 2.5 | 50 | 0 | 1350 | 150 |
| 3 μg Tn cluster KLH + QS-21 | | | | |
| 3.1 | 0 | 0 | 12150 | 450 |
| 3.2 | 0 | 0 | 12150 | 4050 |
| 3.3 | 0 | 0 | 36450 | 450 |
| 3.4 | 0 | 0 | 36450 | 450 |
| 3.5 | 0 | 0 | 36450 | 1350 |

TABLE 2-continued

Antibody Titers by Elisa against Tn-Cluster: 10 µg Tn cluster-Pam

| Group | Pre-serum IgM | Pre-serum IgG | 10 days post 3rd IgM | 10 days post 3rd IgG |
|---|---|---|---|---|
| 3 ug Tn cluster BSA + QS-21 | | | | |
| 4.1 | 0 | 0 | 450 | 1350 |
| 4.2 | 0 | 0 | 150 | 4050 |
| 4.3 | 0 | 50 | 450 | 450 |
| 4.4 | 0 | 0 | 450 | 150 |
| 4.5 | 0 | 0 | 1350 | 150 |

0.3 µg/well antigen plated in alcohol; serum drawn 11 days post 3rd vaccine.

TABLE 3

Antibody Titers by Elisa against Tn-Cluster: Tn Cluster-Pam

| Group | Pre-serum (before 5th Vaccination) IgM | Pre-serum IgG | Post Serum (10 days after 5th Vaccination) IgM | Post Serum IgG |
|---|---|---|---|---|
| 1.1 | 2560 | 200 | 640 | 5120 |
| 1.2 | 25.600 | 800 | 1280 | 320 |
| 1.3 | 640 | 160 | 640 | 1280 |
| 1.4 | 2560 | 1280 | 25.600 | 5120 |
| 1.5 | 640 | 5120 | 2560 | 5120 |
| Tn Cluster-Pam + QS-21 | | | | |
| 2.1 | 6400 | 1280 | 128.000 | 0 |
| 2.2 | 3200 | 160 | 5120 | 200 |
| 2.3 | 3200 | 1280 | 16.000 | 640 |
| 2.4 | 6400 | 640 | 8000 | 200 |
| 2.5 | 5120 | 80 | 64.000 | 2560 |
| Tn Cluster-KLH | | | | |
| 3.1 | 6400 | 1600 | 25.600 | 25.600 |
| 3.2 | 2560 | 3200 | 128.000 | 25.600 |
| 3.3 | 16.000 | 8000 | 128.000 | 25.600 |
| 3.4 | 640 | 12.800 | 5120 | 25.600 |
| 3.5 | 5120 | 12.800 | 25.600 | 3200 |
| Tn-Cluster-BSA | | | | |
| 4.1 | 2560 | 12.800 | 2560 | * |
| 4.2 | 800 | 200 | 128.000 | 400 |
| 4.3 | 400 | 2560 | 6400 | 400 |
| 4.4 | 800 | 2560 | 12800 | 2560 |
| 4.5 | 1280 | 200 | 3200 | 3200 |

0.2 µg/well plated in ethanol.
*ND

TABLE 4

Tn-Cluster FACS Analysis; Serum Tested 11 Days Post 3rd Vaccination. FACS analysis using LSC cell line (Colon Cancer Cell line).

| Group | IgG (% Gated) | IgM (% Gated) |
|---|---|---|
| Tn Cluster Pam | | |
| 1-1 | 93.95 | 16.59 |
| 1-2 | 19.00 | 66.15 |
| 1-3 | 54.45 | 40.51 |
| 1-4 | 46.99 | 39.98 |
| 1-5 | 3.07 | 32.83 |
| Tn Cluster-Pam + QS-21 | | |
| 2-1 | 12.00 | 76.78 |
| 2-2 | 2.48 | 36.76 |
| 2-3 | 20.27 | 46.41 |
| 2-4 | 10.64 | 55.29 |
| 2-5 | 3.37 | 38.95 |
| Tn-Cluster-KLH | | |
| 3-1 | 96.36 | 66.72 |
| 3-2 | 93.12 | 45.50 |
| 3-3 | 97.55 | 32.96 |
| 3-4 | 94.72 | 49.54 |
| 3-5 | 83.93 | 64.33 |
| Tn-Cluster-BSA | | |
| 4-1 | 80.65 | 41.43 |
| 4-2 | 90.07 | 31.68 |
| 4-3 | 42.86 | 54.03 |
| 4-4 | 95.70 | 63.76 |
| 4-5 | 92.14 | 51.89 |

TABLE 5

Results of Tn-trimer-Cys-KLH and Tn-trimer-Cys-BSA (MBS cross-linked) Conjugates

| Conjugate | Amt of Carbohydrate & KLH used for Conjugation Carbo. | KLH | Final Conjugation Volume | Amt of Carbohydrate Recovered Carbohydrate | KLH | % Recovered Carbohydrate | KLH | µg of carbohydrate/100 µl | µg of KLH/100 µl |
|---|---|---|---|---|---|---|---|---|---|
| Tn-trimer-Cys-KLH | 2.0 mg | 5.0 mg | 4.25 ml 2.5* | 141.174 µg | 3612.5 µg | 7% | 72.25% | 3.321 5.65 | 85 (3 µg/mouse; 300 µl/vial¶) |
| Tn-trimer-Cys-BSA | 2.0 | 2.0 | 3.25 1* | 108.9 | 2762.5 | 5.445 | 100 | 3.35 10.89 | 85 (3 µg/mouse; 170 µl/vial¶) |

*After concentration.
¶Approximate amount.

A Total Synthesis of the Mucin Related F1α Antigen

Figure 22A:
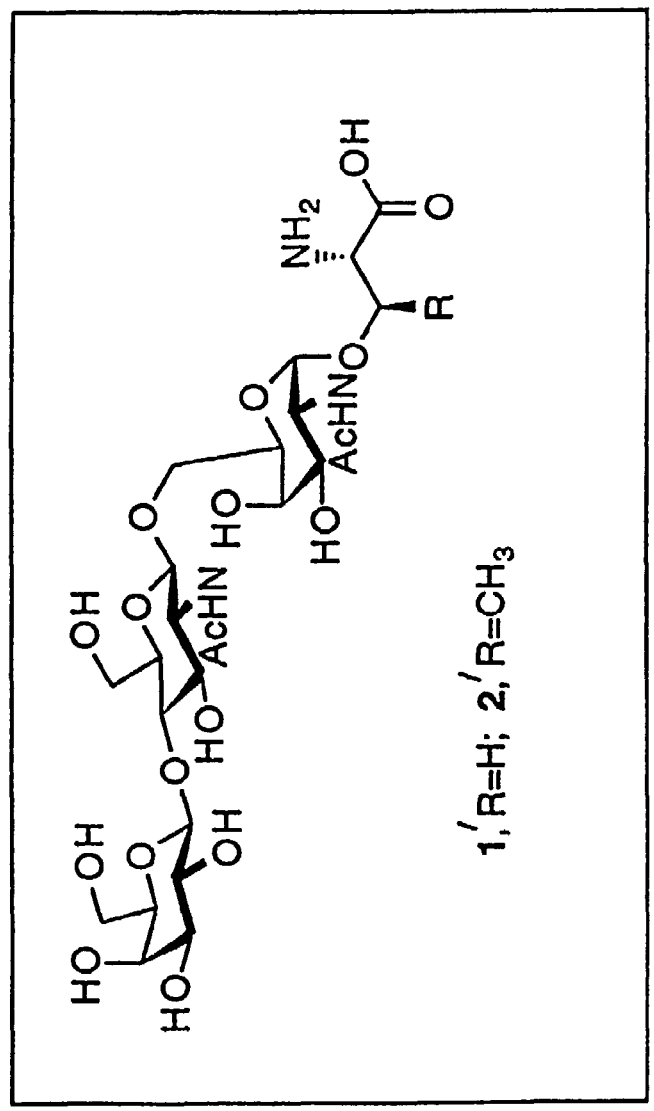
FIG. 22 shows (A) a mucin related F1α antigen and a retrosynthetic approach to its preparation; and (B) a method of preparing intermediates 5' and 6'. conditions: i) $NaN_3$, CAN, $CH_3$, CN, −20° C., overnight, 40%, α (4a'):β (4b') 1:1; ii) PhSH, EtN(i-Pr)$_2$, $CH_3$,CN, 0° C., 1h, 99.8%, iii) $K_2CO_3$, $CCl_3$,CN, $CH_2Cl_2$, rt, 5 h, 84%, 5a':5b' 1:5; iv) DAST, $CH_2Cl_2$, 0° C., 1 h, 93%, 6a':6b' 1:1.
Figure 22A:
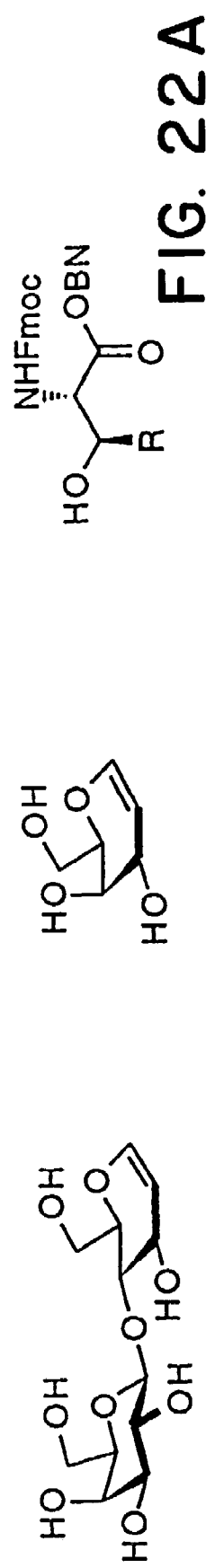

The present invention provides derived mimics of surfaces of tumor tissues, based mainly on the mucin family of glycoproteins. Ragupathi, G., et al., *Angew. Chem. Int. Ed. Engl.* 1997, 36, 125. (For a review of this area see Toyokuni, T.; Singhal, A. K. *Chem. Soc. Rev.* 1995, 24, 231; Dwek, R. A. *Chem. Rev.* 1996, 96, 683.) Due to their high expression on epithelial cell surfaces and the high content of clustered O-linked carbohydrates, mucins constitute important targets for antitumor immunological studies. Mucins on epithelial tumors often carry aberrant α-O-linked carbohydrates. Finn, O. J., et al., *Immunol. Rev.* 1995, 145, 61; Saitoh, O. et al., *Cancer Res.* 1991, 51, 2854; Carlstedt, I.; Davies, J. R. *Biochem. Soc. Trans.* 1997, 25, 214. The identified F1α antigens 1' and 2' represent examples of aberrant carbohydrate epitopes found on mucins associated with gastric adenocarcinomas (FIG. 22A). Yamashita, Y., et al., *J. Nat. Cancer Inst.* 1995, 87, 441; Yamashita, Y., et al., *Int. J. Cancer* 1994, 58, 349. Accordingly, the present invention provides a method of constructing the F1α epitope through synthesis. A previous synthesis of F1α is by Qui, D.; Koganty, R. R. *Tetrahedron Lett.* 1997, 38, 45. Other prior approaches to α-O-linked glycopeptides include Nakahara, Y., et al., in *Synthetic Oligasaccharides, Indispensable Probes for the Life Sciences* ACS Symp. Ser. 560, pp 249–266 (1994); Garg, H. G., et al., *Adv. Carb. Chem. Biochem.* 1994, 50, 277; Paulsen, H., et al., *J. Chem. Soc., Perkin Trans.* 1, 1997, 281; Liebe, B.; Kunz, H. *Angew. Chem. Int. Ed. Engl.* 1997, 36, 618; Elofsson, M., et al., *Tetrahedron* 1997, 53, 369; Meinjohanns, E., et al., *J. Chem. Soc., Perkin Trans.* 1, 1996, 985; Wang, Z.-G., et al., *Carbohydr. Res.* 1996, 295, 25; Szabo, L., et al., *Carbohydr. Res.* 1995, 274, 11.

Tthe F1α structure could be constructed from the three principal building units I–III (FIG. 22A). Such a general plan permits two alternative modes of implementation. (For a comprehensive overview of glycal assembly, see: Bilodeau, M. T.; Danishefsky, S. J. *Angew. Chem. Int. Ed. Engl.* 1996, 35, 1381. For applications toward the synthesis of carbohydrate tumor antigen based vaccines, see Sames, D., et al., *Nature* 1997, 389, 587; Park, T. K., et al., *J. Am. Chem. Soc.* 1996, 118, 11488; and Deshpande, P. P.; Danishefsky, S. J. *Nature* 1997, 387, 164.) First, a GalNAc-serine/threonine construct might be assembled in the initial phase. This would be followed by the extension at the "non-reducing end" (II+III, then I). Alternatively, the entire glycodomain could be assembled first in a form of trisaccharide glycal (I+II). This step would be followed by coupling of the resultant trisaccharide donor to a serine or threonine amino acid residue (cf. II). Both strategies are disclosed herein.

Figure 22B:
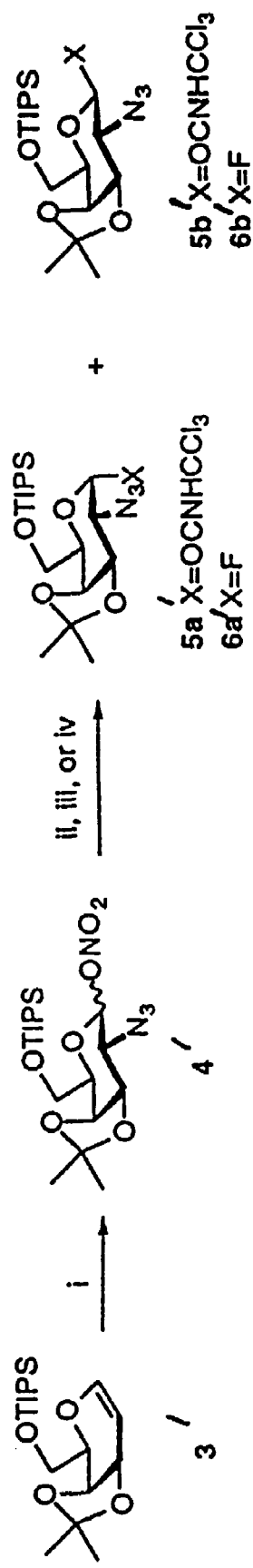

The first synthetic approach commenced with preparation of monosaccharide donors 5a'/b' and 6a'/b' (FIG. 22B). The protecting groups of galactal (cf. II) were carefully chosen to fulfill several requirements. They must be stable to reagents and conditions in the azidonitration protocol (vide infra). Also, the protecting functions must not undermine the coupling step leading to the glycosyl amino acid. After some initial experimentation, galactal 3' became the starting material of choice. The azidonitration protocol ($NaN_3$, CAN $CH_3CN$, –20° C.) provided a 40% yield of 1:1 mixture of 4a' and 4b'. Lemieux, R. U.; Ratcliffe, R. M. *Can. J. Chem.* 1979, 57, 1244. Both anomers were hydrolyzed and then converted to a 1:5 mixture of trichloroacetimidates 5a' and 5b' in good yield (84%). Schmidt, R. R.; Kinzy, W. *Adv. Carbohydr. Chem. Biochem.* 1994, 50, 84. Alternatively, hydrolysis of nitrate 4' followed by use of the DAST reagent (Rosenbrook, Jr. W., et al., *Tetrahedron Lett.* 1985, 26, 3; Posner, G. H.; Haines, S. R. *Tetrahedron Lett.* 1985, 26, 5) yielded a 1:1 mixture of fluoride donors 6a' and 6b'. In both cases the α/β anomers were separable, thus allowing the subsequent investigation of their behavior in the coupling event. The best results obtained from the coupling of donors 5'–6' to serine or threonine acceptors bearing the free side chain alcohol, with protected carboxy and amino moieties are summarized in Table 5a.

The trichloroacetimidate donor type 5' provided excellent yields in coupling reactions with the serine derived alcohol 7'. After optimization, donor 5b' in the presence of TMSOTf in THF (entry 2, Table 5a) provided 86% yield of pure α-product 9'. Interestingly, the donor 5a' also provided α-glycoside 9' exclusively. The coupling of donor 5b' to threonine, though stereoselective, was low yielding. In this instance the fluoride donors 6a' and 6b', promoted by $Cp_2ZrCl_2$/$AgClO_4$ provided desired glycosyl threonine 10' in excellent yield (82–87%) though with somewhat reduced selectivity (6:1, α:β). Ogawa, T. *Carbohydrate Res.* 1996, 295, 25. Thus, both sets of donors proved complementary to one another and glycosyl serine 9' as well as glycosyl threonine 10' were in hand in high yield and with excellent margins of stereoselectivity. It was found that the configurations at the anomeric centers of these donors had no practical effect on the stereochemical outcome of their coupling steps. This result differs from the finding with commonly used 2-deoxy-2-azido-tri-O-acetylgalactose-1-O-trichloroacetimidate. See Schmidt, R. R.; Kinzy, W., id. In that case each anomer yields a different ratio of α/β products (see below).

TABLE 5a

| x | Catalyst/promotor | R = H (9')<br>α::β (%) | R = $CH_3$ (10')<br>α::β (%) |
|---|---|---|---|
| —O(CNH)$CCl_3$(5b') | TMSOTf (0.1 eq), $CH_2Cl_2$/Hex | 7:3 (100%) | 7:1(33%) |
| —O(CNH)$CCl_3$(5b') | TMSOTf (0.5 eq), THF | 1:0 (86%) | 1:0 (15%) |
| —O(CNH)$CCl_3$(5a') | TMSOTf (0.1 eq), THF | 1:0 (66%) | — |
| —F (6a') | $Cp_2ZrCl_2$/$AgClO_4$ (2 eq), $CH_2Cl_2$ | 2:1 (89%) | 6:1 (87%) |
| —F(6b') | $Cp_2ZrCl_2$/$AgClO_4$ (2 eq), $CH_2Cl_2$ | 2:1 (91%) | 6:1 (82%) |

Figure 23:
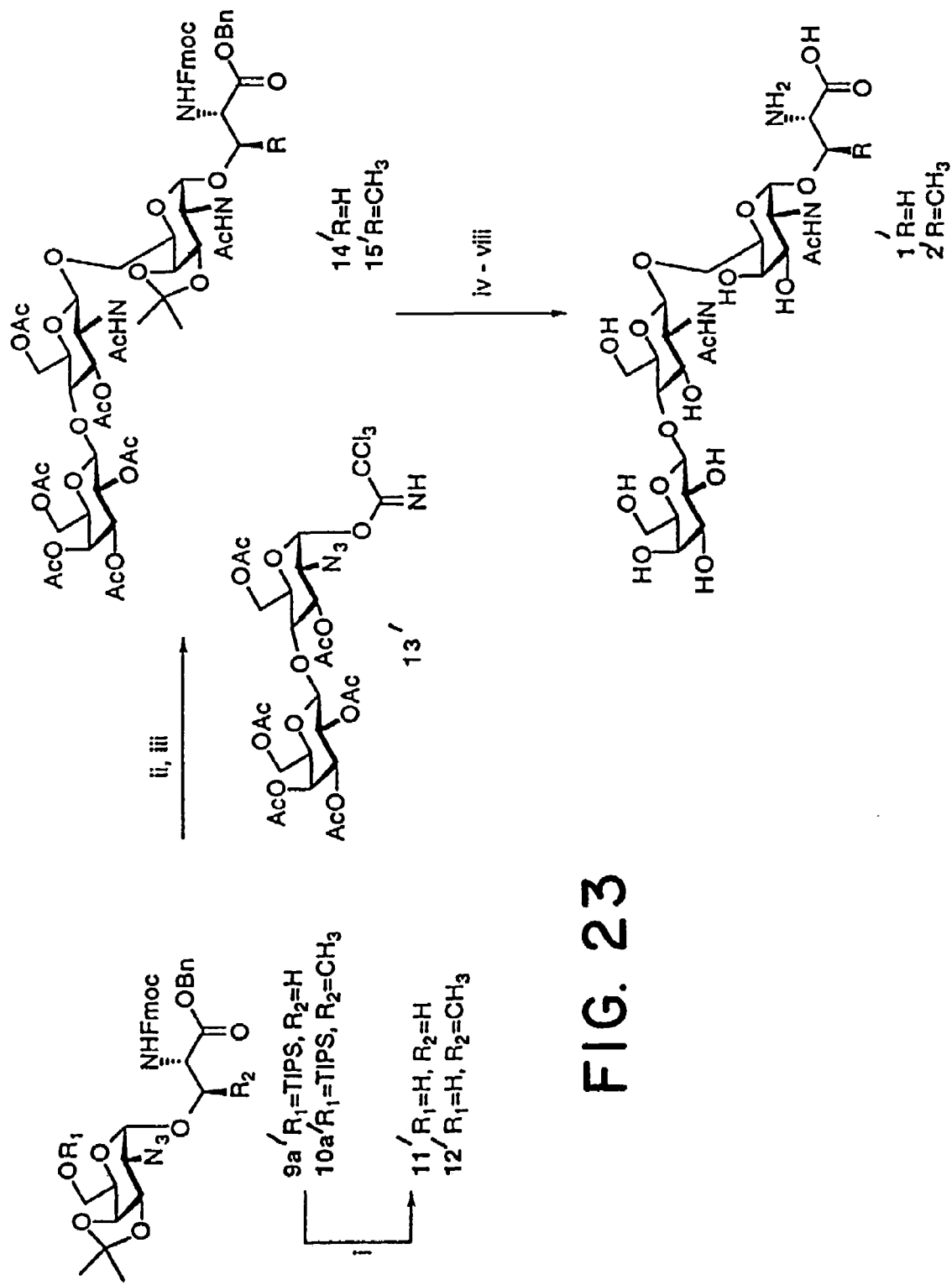
FIG. 23 shows a method of preparing intermediates 1' and 2'. Conditions: i) TBAF, HOAc, THF, rt, 3d, 100% yield for 9', 94% yield for 10'; ii) 11', $BF_3$,$Et_2O$, −30° C., overnight; iii) AcSH, pyridine, rt, overnight, 72% yield yield based on 50% conversion of 11', 58% yield based on 48% conversion of 12' (two steps); iv) 80% aq. HOAc, overnight, rt–40° C.; v) $Ac_2O$, pyridine, rt., overnight; vi) 10% Pd/C, $H_2$, MeOH—$H_2O$, rt, 4h; vii) Morpholine, DMF, rt, overnight; viii) NaOMe, MeOH-THF, rt, overnight, 64% yield for 1', 72% yield for 2' (five steps).

The TIPS group at position 6 was quantitatively removed with TBAF and AcOH to give acceptors 11' and 12' (FIG. 23). The final coupling to lactosamine donor 13' was performed in the presence of $BF_3$ $OEt_2$ in THF. The crude products from this apparently stereoselective coupling step were converted to compounds 14' and 15', respectively with thioacetic acid. Paulsen, H., et al., *Liebigs Ann. Chem.* 1994, 381. These glycosyl amino acids represent suitable units for the glycopeptide assembly. In order to confirm their structure, we executed global deprotection. This was accomplished in five steps yielding free F1α antigen 1' and 2' in 70% and 73% yield, respectively (FIG. 23). The glycosidic linkages were not compromised under the conditions of the acidic and basic deprotection protocols.

Figure 24:
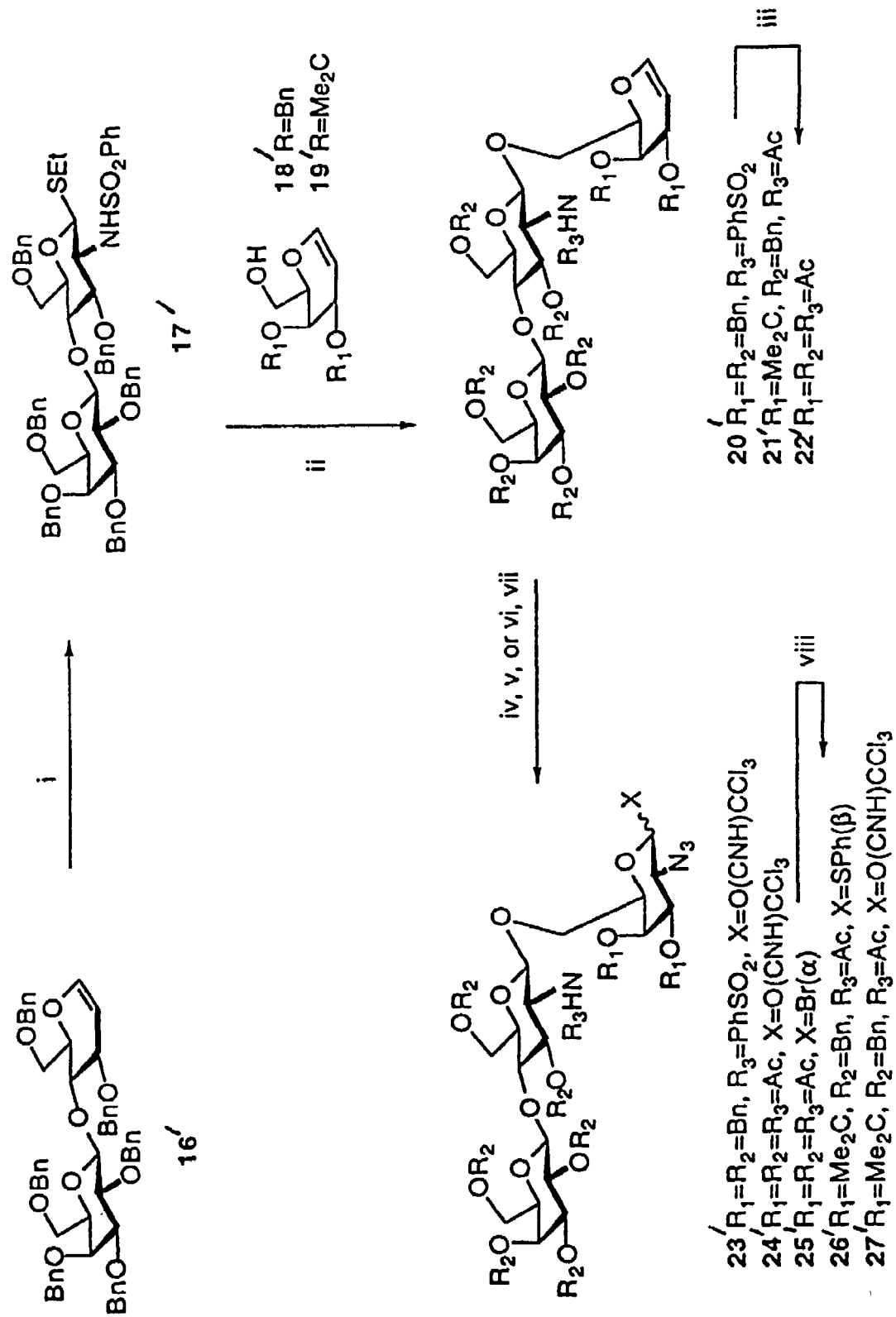
FIG. 24 shows a method of preparing intermediates in the synthesis of F1α antigen. Conditions: i) (sym-collidine)$_2$ $ClO_4$, $PhSO_2NH_2$, 0° C.; LiHMDS<EtSH, −40° C.-rt, 88% yield in two steps; ii) MeOTf, DTBP, 0° C., 86% yield for 20' plus 8% yield of α isomer; 85% yield for 21' plus 6% yield of α isomer; iii) Na, $NH_3$, 78° C.; $Ac_2O2$, Py, rt, for 22', 59% yield in two steps; iv) $NaN_3$, CAN, $CH_3CN$, −20° C.; v) PhSH, EtN(i-Pr)$_2$; $Ccl_3CN$, $K_2CO_3$; for 23', 17% yield of 2:7, α/β in three steps; for 24' 30% yield of 3; 1, α/β in three steps; vi) LiBr, $CH_3CN$, for 25', 46% yield, α only; vii) $Ac_2O$, Py; Na—Hg, $Na_2HPO_4$, 94% yield in two steps, $NaN_3$, CAN, 26% yield, PhSH, EtN(i-Pr)$_2$; $K_2CO_3$, $Ccl_3CN$, 53% yield in two steps (27'); viii) LiSph, THF, 60% yield, β only (26').

A direct coupling Is provided of trisaccharide donors which are synthesized through glycal assembly (Bilodeau, M. T.; Danishefsky, S. J. *Angew. Chem. Int. Ed. Engl.* 1996, 35, 1381) using suitably protected serine or threonine amino acids. This logic was discussed earlier under the formalism I+II followed by coupling with Ill. The trisaccharide donors 23'–27' were prepared as outlined in FIG. 24. Readily available lactal 16' (Kinzy, W.; Schmidt, R. R. *Carbohydrate Res.* 1987, 164, 265) was converted to the thio-donor 17' via a sequence of the iodo-sulfonamidation and subsequent rearrangements with ethanethiol in the presence of LiH-MDS. Park, T. K., et al., *J. Amer. Chem. Soc.,* 1996, 118, 11488. The MeOTf-promoted coupling to galactals 18' and 19' provided the trisaccharide glycals 20' and 21' in excellent yield and stereoselectivity. Reductive deprotection of the benzyl groups and the sulfonamide in 20' and subsequent uniform acetylation of the crude product yielded glycal 22'. The azidonitration of glycal 20'–22' provided intermediate azidonitrates, which were converted to the corresponding donors 23'–27'.

The results of couplings of these trisaccharide donors with suitable serine/threonine derived acceptors are summarized in Table 6. The protection pattern again had a profound effect on the reactivity and stereoselectivity of the coupling. Despite the seemingly large distance between the hydroxyl and other functional groups of the lactose domain from the anomeric center, these substituents strongly affects the stereochemical outcome. Qualitatively, uniform protection of functionality with electron donating groups (cf. benzyl) leads to a very reactive donor by stabilizing the presumed oxonium cation. By contrast, electron withdrawing protecting groups tend to deactivate the donor in the coupling step. Andrews, C. W., et al., *J. Org. Chem.* 1996, 61, 5280; Halcomb, R. L.; Danishefsky, S. J. *J. Am. Chem. Soc.* 1989, 111, 6656. Such deactivation may also confer upon a donor some stereochemical memory in terms of sensitivity of coupling to the original stereochemistry of the donor function at the anomeric center. As shown in Table 6, per-O-benzyl-protected donor 23' was highly reactive at −78° C. providing product 28' in 90% yield and high stereoselectivity (10:1, first entry, Table 6). A dramatic difference was seen upon changing the overall protection from per-O-benzyl to per-O-acetyl groups as demonstrated in the case of donor 24'. The yield and stereoselectivity of the coupling step were diminished. Comparable results were obtained with donors 25' and 26'.

In the case of compounds 27' and 28', where the galactosamine ring was conformationally restricted by engaging the 3- and 4-positions in the cyclic acetonide, an even more surprising finding was registered. donor 27α' with a per-O-benzyl protected lactosamine disaccharide afforded only the desired α-anomer 31'. However, a mixture of trichloroacetimidates as well as the pure β anomer of 28' yielded undesired β anomer 32' exclusively. Thus, a modification of the protection pattern at a relatively distant site on the second and third carbohydrate units (from the ring containing the donor function) exerted a profound reversing effect on the stereoselectivity of glycosidation. Conformational limitations imposed on a ring within the donor ensemble by cyclic protecting groups can influence donor reactivity, as judged by rates of hydrolysis. Wilson, B. G.; Fraser-Reid, B. *J. Org. Chem.* 1995, 60, 317; Fraser-Reid, B., et al., *J.Am. .Chem.Soc,.* 1991, 113, 1434. Protecting groups, via their electronic, steric and conformational influences, coupled with solvation effects, can strongly modulate the characteristics of glycosyl donors. Thus, longer range effects cannot be accurately predicted in advance in the glycosidation of serine and threonine side chain hydroxyls.

Accordingly, the present invention demonstrates unexpected advantages for the cassette approach wherein prebuilt stereospecifically synthesized α-O-linked serine or threonine glycosides (e.g., 9' and 10') are employed to complete the saccharide assembly.

TABLE 6

| $R_1$ | $R_2$ | $R_3$ | X | $R_4$ | Catalyst/Promotor | α:β(%) |
|---|---|---|---|---|---|---|
| Bn | Bn | PhSO$_2$HN | O(CNH)CCl$_3$ (23'α) | Me | TMSOTf (0.5 eq), THF | 10:1 (90%) 29' |
| Ac | Ac | AcHN | O(CNH)CCl$_3$ (24'α/β 3:1) | Bn | TMSOTf (1.0 eq), THF | 2:1 (22%) 30' |
| Ac | Ac | AcHN | Br (25'α) | Bn | AgClO$_4$ (1.5 eq), CH$_2$Cl$_2$ | 3.5:1 (56%) 30' |
| Ac | Ac | AcHN | SPh (26'β) | Bn | NIS/TfOH, CH$_2$Cl$_2$ | 2:1 (40%) 30' |
| Me$_2$C | Bn | AcHN | O(CNH)CCl$_3$ (27'α) | Bn | TMSOTf (0.3 eq), THF | 1:0 (50%) 31' |
| Me$_2$C | Ac | N$_3$ | O(CNH)CCl$_3$ (28'α/β 1:1) | Bn | BF$_3$Et$_2$O (0.5 eq), THF | 0:1 (67%) 32' |
| Me$_2$C | Ac | N$_3$ | O(CNH)CCl$_3$ (28'β) | Bn | BF$_3$Et$_2$O (1.5 eq), THF | 0:1 (35%) 32' |

What is claimed is:

1. A glycoconjugate having the structure:

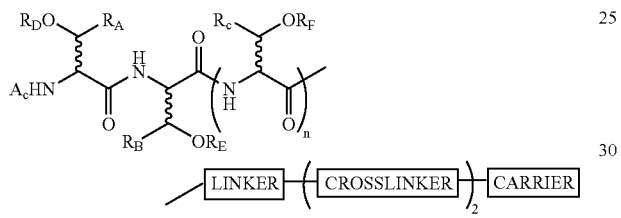

wherein the linker is —O—, —NR$_G$—, —NR$_G$(CR$_H$R$_J$)$_k$NR$_K$—, NR$_G$(CR$_H$R$_J$)$_K$NR$_K$(C=O)(CR$_H$R$_J$)$_K$S—, —(CR$_H$R$_J$)$_K$NR$_K$—, —O(CR$_H$R$_J$)$_k$NR$_k$—, an oligoester fragment comprising from 2 to about 20 hydroxy acyl residues, a peptidic fragment comprising from 2 to about 20 amino acyl residues, or a linear or branched chain alkyl or aryl carboxylic ester, wherein each occurrence of k is independently 1–8;

wherein each occurrence of R$_G$, R$_H$, R$_J$ or R$_K$ is independently hydrogen, a linear or branched, substituted or unsubstituted, cyclic or acyclic alkyl moiety, or a substituted or unsubstituted aryl moiety;

wherein the crosslinker is a moiety derived from a crosslinking reagent capable of conjugating a surface amine of the carrier with a terminal thiol of the linker;

wherein the carrier is a protein or lipid;

wherein n is 1, 2, 3 or 4;

wherein q is 0 or 1;

wherein each occurrence of R$_A$, R$_B$ and R$_C$ is independently H or methyl; and wherein each occurrence of R$_D$, R$_E$ and R$_F$ independently comprises a carbohydrate domain having the structure:

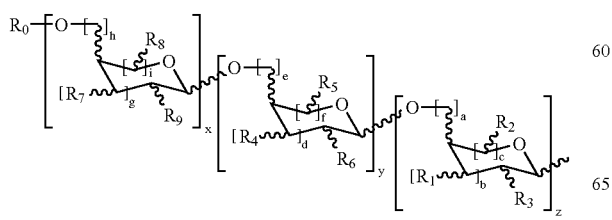

wherein a, b, c, d, e, f, g, h, i, x, y and z are each independently 0, 1, 2 or 3, with the proviso that R$_D$, R$_E$, and R$_F$ are carbohydrates independently comprised of furanose or pyranose moieties, whereby the sum of b and c is 1 or 2, the sum of d and f is 1 or 2, and the sum of g and i is 1 or 2, and with the proviso that x, y and z are not simultaneously 0; wherein R$_0$ is a hydrogen, linear or branched chain alkyl, acyl, arylalkyl or aryl group; wherein each occurence of R$_1$, R$_2$, R$_3$, R$_4$, R$_5$, R$_6$, R$_7$, R$_8$, and R$_9$ is independently hydrogen, OH, OR$^i$, NH$_2$, NHCOR$^i$, F, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl, or aryl group; wherein each occurrence of R$^i$ is independently hydrogen, CHO, CO$_2$R$^{ii}$, a substituted or unsubstituted linear or branched chain alkyl, acyl, arylalkyl, or aryl group, or a saccharide moiety having the structure:

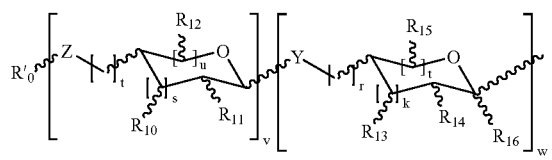

wherein Y and Z are independently NH or O; wherein k, l, r, s, t, u, v and w are each independently 0, 1 or 2, with the proviso tat the v and w bracketed structures represent furanose or pyranose moieties and the sum of l and k is 1 or 2, and the sum of s and u is 1 or 2, and with the proviso that v and w are not simultaneously 0; wherein R'$_0$ is hydrogen, a linear or branched chain alkyl, acyl, arylalkyl or aryl group; wherein each occurrence of R$_{10}$, R$_{11}$, R$_{12}$, R$_{13}$, R$_{14}$ and R$_{15}$ is independently hydrogen, OH, OR$^{iii}$, NH$_2$, NHCOR$^{iii}$, F, CH$_2$OH, CH$_2$OR$^{iii}$, or a substituted or unsubstituted linear or branched chain alkyl, (mono-, di- or tri)hydroxyalkyl, (mono- di- or tri-)acyloxyalkyl, arylalkyl or aryl group; wherein R$_{16}$ is hydrogen, CO$_2$H, CO$_2$R$^{ii}$, CONHR$^{ii}$, a substituted or unsubstituted linear or branched chain alkyl or aryl group; wherein each occurrence of R$^{iii}$ is independently hydrogen, CHO, CO$_2$R$^{iv}$, or a substituted or unsubstituted linear or branched chain alkyl, acyl, arylalkyl or aryl group; and wherein each occurrence of $R^{ii}$ and $R^{iv}$ is independently hydrogen, or a substituted or unsubstituted linear or branched chain alkyl, acyl, arylalkyl or aryl group, with the limitation that each of $R_D$, $R_E$, and $R_F$ comprise a carbohydrate domain, or truncated or elongated version thereof, that is present on tumor cells, and with the further limitation that (i) when q is 0, the linker is —NH(CH$_2$)$_2$—O—(CH$_2$)$_2$NH—, and the carrier is KLH or human serum albumin, then $R_D$, $R_E$ and $R_F$ are not simultaneously STn, and (ii) when q is 0, the linker is —NH(CH$_2$)$_3$(C=O)—, and the carrier is ovine serum albumin, then $R_D$, $R_E$ and $R_F$ are not simultaneously Tn.

2. The glycoconjugate of claim 1, wherein n is 1, q is 0, the linker is —NH(CH$_2$)$_j$NH—, the carrier is a lipid, and the glycoconjugate has the structure:

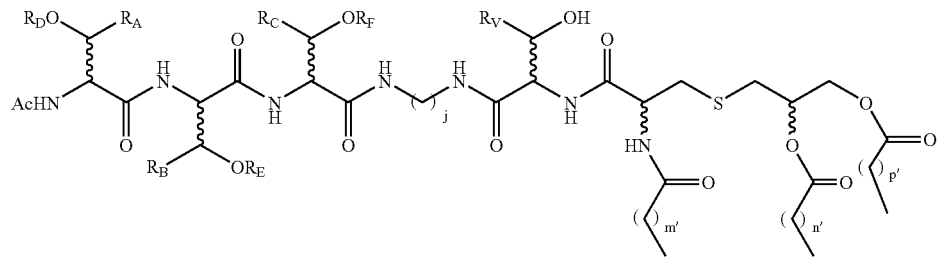

wherein m', n' and p' are independently integers between about 8 and 20;

j is an integer between 1 and about 8;

$R_V$, $R_A$, $R_B$ and $R_C$ are independently hydrogen, substituted or unsubstituted linear or branched chain lower alkyl or substituted or unsubstituted phenyl;

$R_D$, $R_E$ and $R_F$ are independently a carbohydrate domain having the structure:

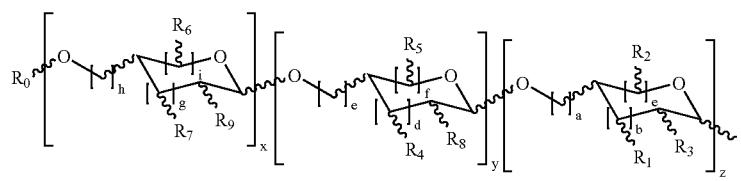

wherein a, b, c, d, e, f, g, h, i, x, y and z are each independently 0, 1, 2 or 3, with the proviso that $R_D$, $R_E$, and $R_F$ are carbohydrates independently comprised of furanose or pyranose moieties, whereby the sum of b and c is 1 or 2, the sum of d and f is 1 or 2, and the sum of g and i is 1 or 2, and with the proviso that x, y and Z are not simultaneously 0; wherein $R_0$ is a hydrogen, linear or branched chain alkyl, acyl, arylalkyl or aryl group; wherein each occurrence of $R_1$, $R_2$, $R_3$, $R_4$, $R_5$, $R_6$, $R_7$, $R_8$, and $R_9$ is independently hydrogen, OH, OR$^i$, NH$_2$, NHCOR$^i$, F, CH$_2$OH, CH$_2$OR$^i$, a substituted or unsubstituted linear or branched chain alkyl, (mono-, di- or tri)hydroxyalkyl, (mono-. di- or tri)acyloxyalkyl, arylalkyl, or aryl group; wherein each occurrence of R$^i$ is independently hydrogen, CHO, CO$_2$R$^i$, a substituted or unsubstituted linear or branched chain alkyl, acyl, arylalkyl, or aryl group, or a saccharide moiety having the stxucture:

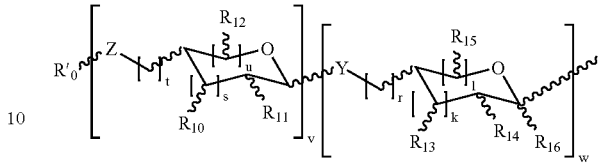

wherein Y and Z are independently NH or O; wherein k, l, r, s, t, u, v and w are each independently 0, 1 or 2, with the proviso tat the v and w bracketed structures represent furanose or pyranose moieties and the sum of l and k is 1 or 2, and the sum of s and u is 1 or 2, and with the proviso that v and w arc not simultaneously 0; wherein R'$_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, OR$^{iii}$, NH$_2$, NHCOR$^{iii}$, F, CH$_2$OH, CH$_2$OR$^{iii}$, or a substituted or unsubstitated linear or branched chain alkyl, (mono-, di- or tri) hydroxyalkyl, (mono- di- or tri-)acyloxyalkyl, arylalkyl or aryl group; wherein RH$_{16}$ is hydrogen, CO$_2$H, CO$_2$R$^{ii}$, CONHR$^{ii}$, a substituted or unsubstituted linear or branched chain alkyl or aryl group; wherein each occurrence of R$^{ii}$ is independently hydrogen, CHO, CO$_2$R$^{iv}$, or a substituted or unsubstituted linear or brandied chain alkyl, acyl, arylalkyl or aryl group; and wherein each occurrence of R$^{ii}$ and R$^{iv}$ is independently hydrogen, or a substituted or unsubstituted linear or branched chain alkyl, acyl, arylalkyl or aryl group;

with the limitation that each of $R_D$, $R_E$, and $R_F$ comprise a carbohydrate domain, or truncated or elongated version thereof, that is present on tumor cells.

3. The glycoconjugate of claim 1 having the structure:

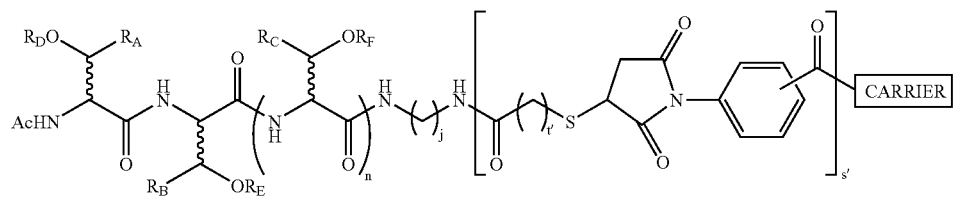

wherein each occurrence of $R_A$, $R_B$ and $R_C$ is independently H or methyl;

n is 1, 2, 3 or 4;

j is an integer from 1–8;

t' is an integer from 1–8;

s' is 0 or 1, wherein when s'=0, the carrier is a lipid, and when s'=1, the carrier is a protein; and each occurrence of $R_D$, $R_E$ and $R_F$ is independently a carbohydrate domain selected from the group consisting of Tn, TF, 2,6-STF, 2,6STh, 3-Le$^y$, 6-Lep$^y$, 3,6-STn, 2,3-ST, a carbohydrate having the structure:

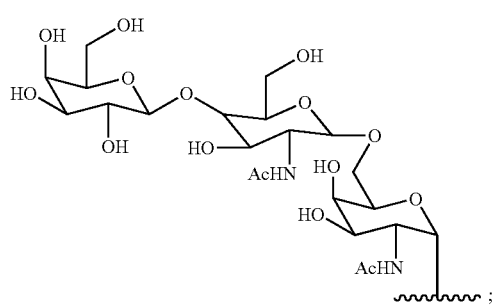

a carbohydrate having the structure:

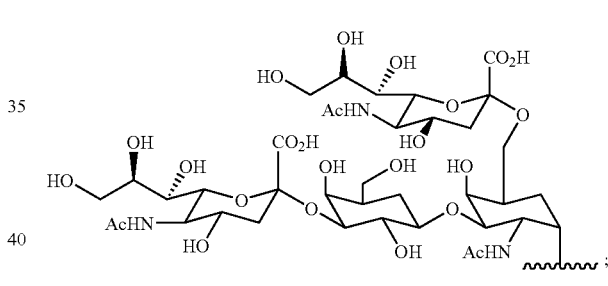

a carbohydrate having the structure:

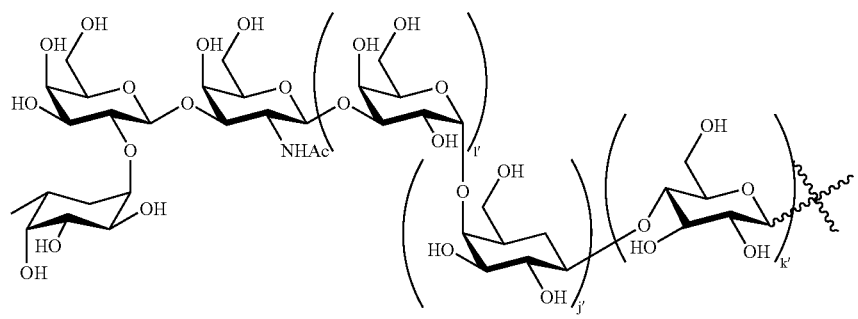

wherein j', k' and l' are each independently 0, 1 or 2; and
a Le$^y$ hexasaccharide having the structure:

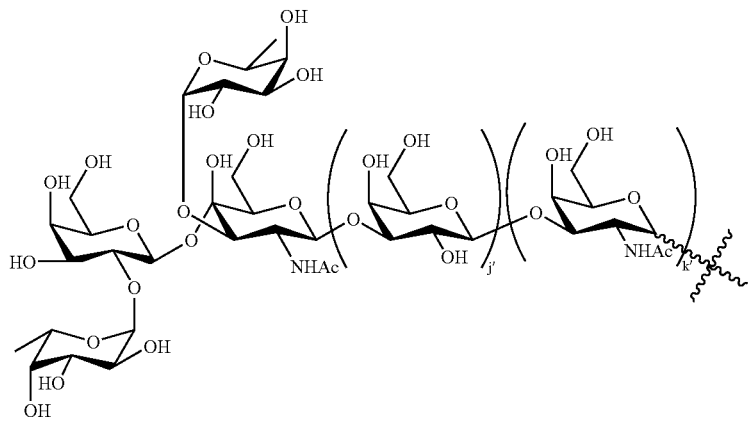

wherein j' and k' are each independently 0, 1 or 2.

4. The glycoconjugate of claim 1 wherein n is 1, q is 1, the linker is —NH(CH$_2$)$_j$NH(C=O)(CH$_2$)$_t$'S—, and the glycoconjugate has the structure:

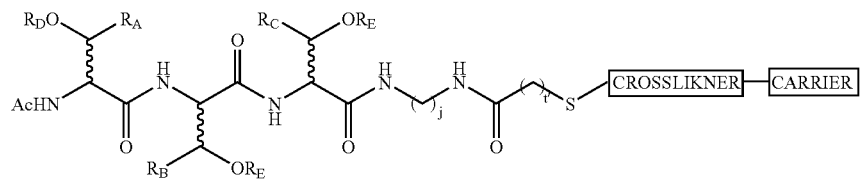

wherein j and t' are independently integers between 1 and about 8.

5. The glycoconjugate of claim 3 wherein n is 1, j is 3 and t' is 1.

6. The glycoconjugate of claim 2 wherein R$_V$, R$_A$, R$_B$ and R$_C$ are each independently methyl.

7. The glycoconjugate of claim 2 wherein R$_V$, R$_A$, R$_B$ and R$_C$ are each independently hydrogen.

8. The glycoconjugate of claim 2 wherein the carbohydrate domains are independently monosaccharides or disaccharides.

9. The glycoconjugate of claim 2 wherein x and y are 0; wherein z is 1; and wherein R$_3$ is NHAc.

10. The glycoconjugate of claim 2 wherein h is 0; wherein g and i are 1; wherein R$_7$ is OH; wherein R$_0$ is hydrogen; and wherein R$_8$ is hydroxymethyl.

11. The glycoconjugate of claim 2 wherein m', n' and p' are each 14; and j is 3.

12. The glycoconjugate of claim 2 wherein each ammo acyl residue therein has an L-configuration.

13. The glycoconjugate of claim 1 or 2, wherein each occurrence of R$_D$, R$_E$ and R$_F$ is independently a carbohydrate domain selected from the group consisting of TE, 2,6-STr, 3-Le$^y$, 6-Le$^y$, 2,3-ST, a carbohydrate having the structure:

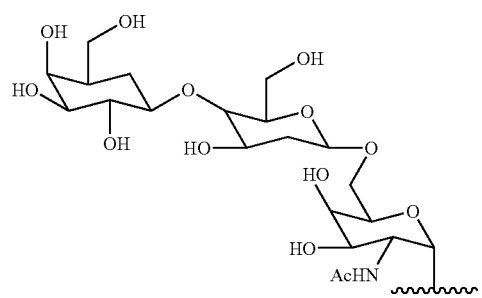

a carbohydrate having the structure:

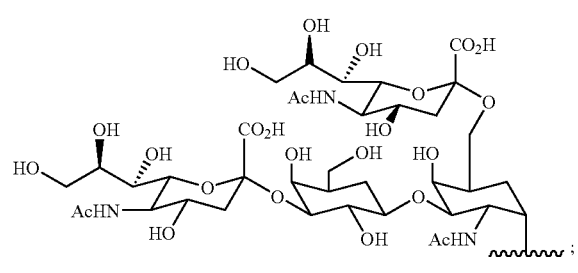

a carbohydrate having the structure:

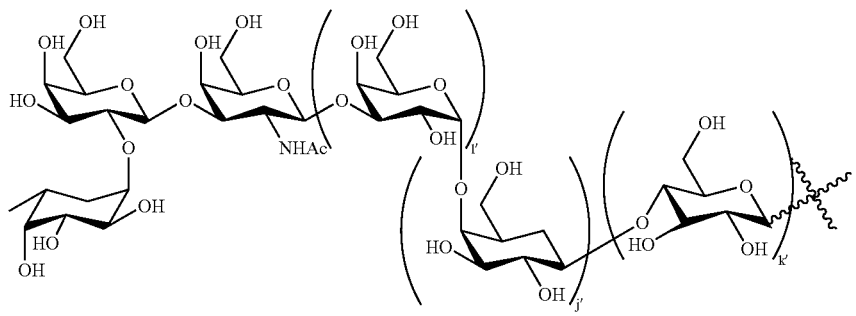

wherein j', k' and l' are each independently 0, 1 or 2; and
a Le$^y$ hexasaccharide having the structure:

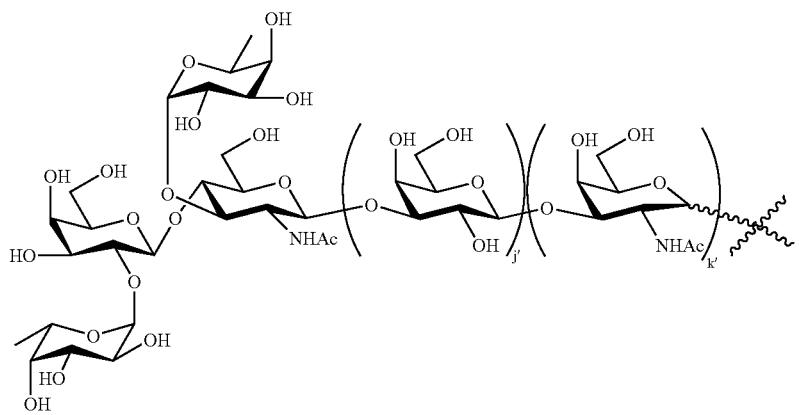

wherein j' and k' are each independently 0, 1 or 2.

14. The glycoconjugate of claim 1 or 3, wherein $R_A$, $R_B$ and $R_C$ are each independently H.

15. The glycoconjugate of claim 1 or 3, wherein $R_A$, $R_B$ and $R_C$ are each independently Me.

16. The glycoconjugate of claim 2 or 3, wherein $R_D$, $R_E$, and $R_F$ are each independently Tn.

17. The glycoconjugate of claim 1, 2 or 3, wherein $R_D$, $R_E$, and $R_F$ are each independently TF.

18. The glycoconjugate of claim 1, 2 or 3, wherein $R_D$, $R_E$, and $R_F$ are each independently 2,6-STF.

19. The glycoconjugate of claim 2 or 3, wherein $R_D$, $R_E$, and $_F$ are each independently 2,6-STn.

20. The glycoconjugate of claim 1, 2 or 3, wherein $R_D$, $R_E$, and $R_F$ are each independently 3-Le$^y$ or 6-Le$^y$.

21. The glycoconjugate of claim 2 or 3, wherein $R_D$, $R_E$, and $R_F$ are each independently 3,6-STn.

22. The glycoconjugate of claim 1, 2 or 3, wherein $R_D$, $R_E$ and $R_F$ are each independently 2,3-ST.

23. The glycoconjugate of claim 1, 2 or 3, wherein $R_D$, $R_E$ and $R_F$ are each independently a carbohydrate having the structure:

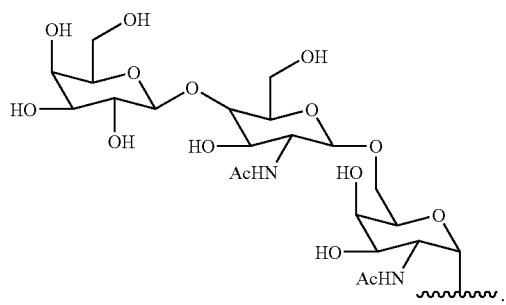

24. The glycoconjugate of claim 1, 2 or 3, wherein $R_D$, $R_E$ and $R_F$ are each independently a carbohydrate having the structure:

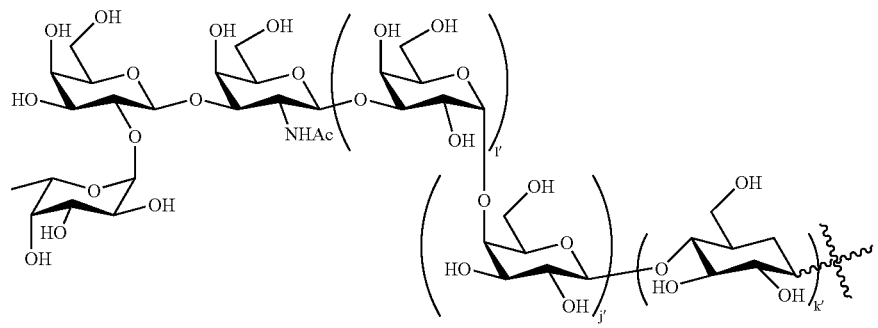

wherein j', k' and l' are each independently 0, 1 or 2.

25. The glycoconjugate of claim 1, 2 or 3, wherein $R_D$, $R_E$ and $R_F$ are each independently a glycophorine antigen having the structure:

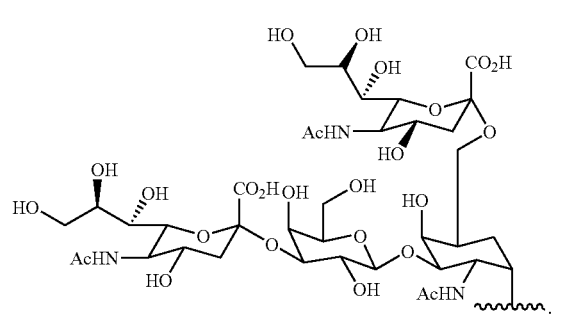

26. The glycoconjugate of claim 1, 2 or 3, wherein $R_D$, $R_E$ and $R_F$ are each independently an $Le^Y$ hexasaccharide having the structure:

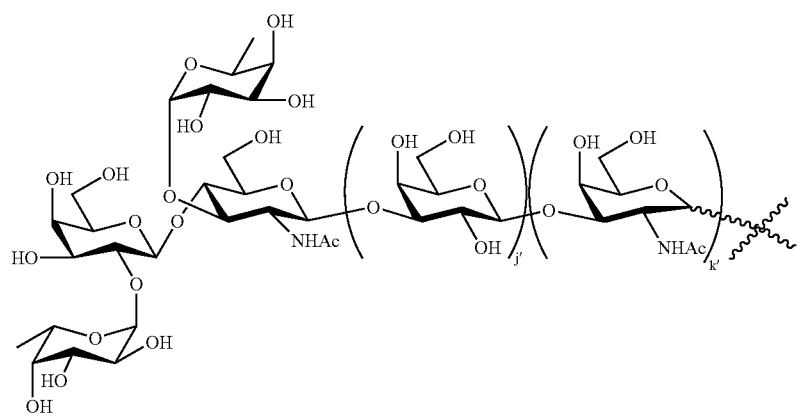

wherein j' and k' are each independently 0, 1 or 2.

27. The glycoconjugate of claim 1, wherein the crosslinker is a fragment having the structure:

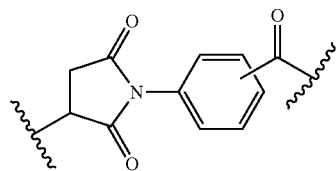

whereby said structure is generated upon conjugation of a maleimidobenzoic acid N-hydroxy succinimide ester with a linker.

28. The glycoconjugate of claim 1, wherein $R_D$, $R_E$ and $R_F$ are not simultaneously each Tn or STn.

29. A glycoconjugate having the structure:
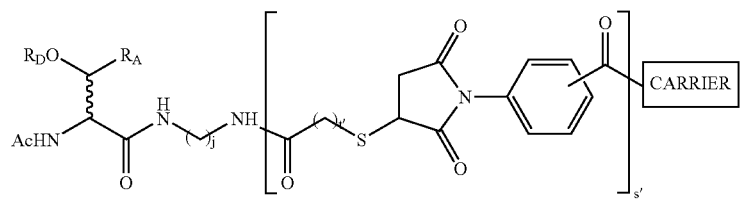
wherein j is 1–8;
t' is 1–8;
s' is 0 or 1, wherein when s'=0, the carrier is a lipid and when s'=1, the carrier is a protein;
$R_A$, is hydrogen or methyl; and
$R_D$ is selected from the group consisting of Tn, TF, 2,6-STF, 2,6-STn, 3-Le$^y$, 6-Le$^y$, 3,6-STn, 2,3-ST, a carbohydrate having the structure:
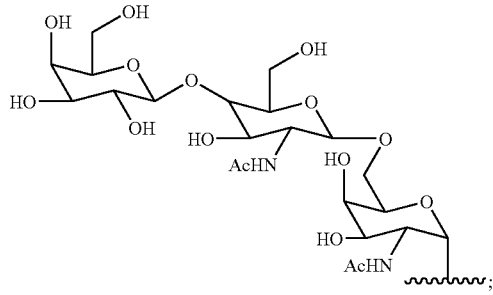
a carbohydrate having the structure:
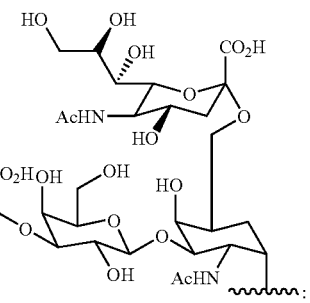
a carbohydrate having the structure:
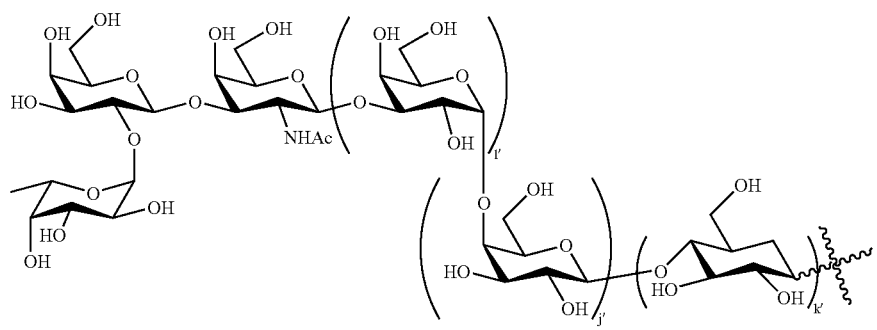

wherein j', k' and l' are each independently 0, 1 or 2; and
a Le$^y$ hexasaccharide having the structure:

[structure]

wherein J' and k' are each independently 0, 1 or 2.

30. The glycoconjugate of claim 29, wherein j is 3 and T' is 1.
31. The glycoconjugate of claim 29, wherein $R_D$ is Tn.
32. The glycoconjugate of claim 29, wherein $R_D$ is TF.
33. The glycoconjugate of claim 29, wherein $R_D$ is 2,6-STE.
34. The glycoconjugate of claim 29, wherein $R_D$ is 2,6-STn.
35. The glycoconjugate of claim 29, wherein $R_D$ is 3-Le$^y$ or 6-Le$^y$.
36. The glycoconjugate of claim 29, wherein $R_D$ is 3,6-STn.
37. The glycoconjugate of claim 29, wherein $R_D$ is 2,3-ST.
38. The glycoconjugate of claim 29, wherein $R_D$, $R_E$ and $R_F$ ere each independently a

[structure]

39. The glycoconjugate of claim 29, wherein $R_D$ is a carbohydrate having the structure:

[structure]

wherein j', k' and l' are each independently 0, 1 or 2.

40. The glycoconjugate of claim 29, wherein $R_D$ is a glycophorine antigen having the structure:

[structure]

41. The glycoconjugate of claim 29, wherein $R_D$ is an Le$^y$ hexasaccharide having the structure:

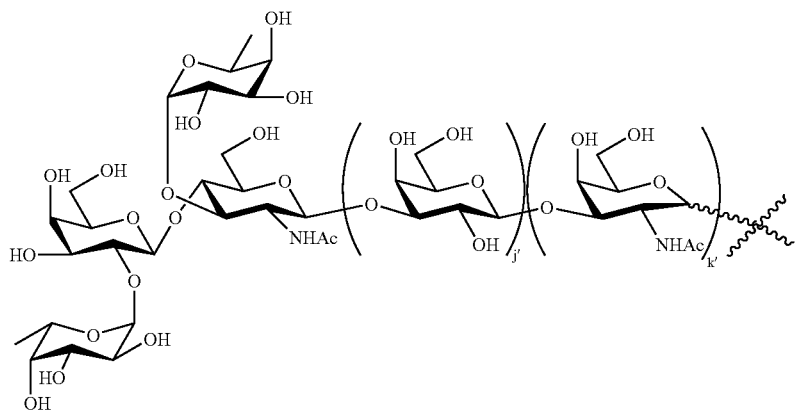

wherein j' and k' are each independently 0, 1 or 2.

42. The glycoconjugate of claim 1, 3, 4 or 29, wherein the carrier is a protein, and the protein is bovine serum albumin, polylysine or KLH.

43. The glycoconjugate of claim 1, 3, 4 or 29, wherein the carrier is a lipid, and the lipid is tripalmitoyl-S-glycerylcysteinylserine.

44. A pharmaceutical composition comprising a compound of claim 1, 2, 3 or 29, and a pharmaceutically acceptable carrier or diluent.

45. The pharmaceutical composition of claim 44 further comprising an immunological adjuvant.

46. The pharmaceutical composition of claim 45, wherein the adjuvant is bacteria or liposomes.

47. The pharmaceutical composition of claim 46, wherein the adjuvant is *Salmonella minnesota* cells; bacille Calmette-Guerin, or QS21.

* * * * *

UNITED STATES PATENT AND TRADEMARK OFFICE
CERTIFICATE OF CORRECTION

PATENT NO. : 7,160,856 B2  Page 1 of 1
APPLICATION NO. : 10/205021
DATED : January 9, 2007
INVENTOR(S) : Danishefsky et al.

It is certified that error appears in the above-identified patent and that said Letters Patent is hereby corrected as shown below:

The exact page and line number where the error occurs in the issued patent is as follows:

In column 59, beginning at 25 and ending at line 33, please delete the structure:

"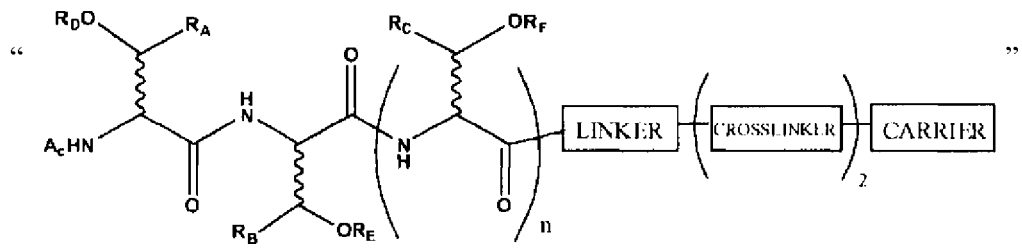"

and insert the structure:

-- 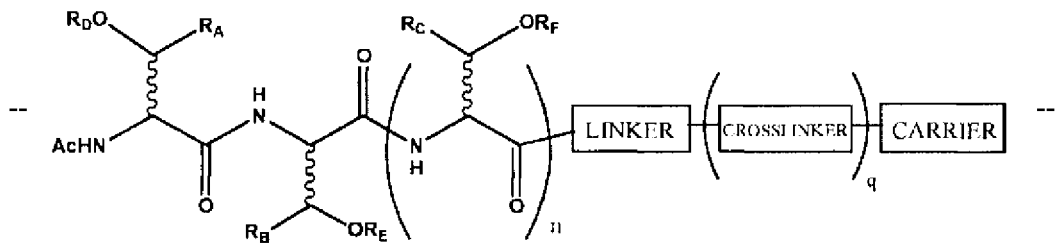 --

Signed and Sealed this

Fourteenth Day of April, 2009

JOHN DOLL
*Acting Director of the United States Patent and Trademark Office*